US009050012B2

(12) United States Patent
Matsumoto

(10) Patent No.: US 9,050,012 B2
(45) Date of Patent: Jun. 9, 2015

(54) FLUORESCENCE-ENDOSCOPE APPARATUS

(71) Applicant: OLYMPUS CORPORATION, Tokyo (JP)

(72) Inventor: Shinya Matsumoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 206 days.

(21) Appl. No.: 13/920,136

(22) Filed: Jun. 18, 2013

(65) Prior Publication Data

US 2014/0005476 A1    Jan. 2, 2014

Related U.S. Application Data

(63) Continuation-in-part of application No. PCT/JP2011/080158, filed on Dec. 27, 2011.

(30) Foreign Application Priority Data

Dec. 27, 2010    (JP) .................................. 2010-290927

(51) Int. Cl.
| | | |
|---|---|---|
| *A61B 1/04* | (2006.01) | |
| *A61B 1/06* | (2006.01) | |
| *A61B 6/00* | (2006.01) | |
| *A61B 1/00* | (2006.01) | |
| *A61B 5/00* | (2006.01) | |

(52) U.S. Cl.
CPC .............. *A61B 1/043* (2013.01); *A61B 1/00009* (2013.01); *A61B 1/0005* (2013.01); *A61B 5/0071* (2013.01); *A61B 5/0075* (2013.01); *A61B 5/0084* (2013.01); *A61B 5/7425* (2013.01)

(58) Field of Classification Search
CPC .... A61B 1/043; A61B 1/00009; A61B 1/045; A61B 1/0638; A61B 5/0071; A61B 5/0075; A61B 5/7425; G01N 2021/6421
USPC .................. 600/109, 160, 181, 473, 476, 477
See application file for complete search history.

(56) References Cited

U.S. PATENT DOCUMENTS 6,473,637 B1 *  10/2002  Hayashi ......................... 600/477
8,214,025 B2 *   7/2012  Takaoka et al. ............... 600/478
(Continued)

FOREIGN PATENT DOCUMENTS

| JP | 2006-043002 A | 2/2006 |
|---|---|---|
| JP | 2008-43396 A | 2/2008 |
| JP | 2009-0542415 A | 12/2009 |

OTHER PUBLICATIONS

International Search Report dated Feb. 21, 2012 issued in PCT/JP2011/080158.

*Primary Examiner* — Thomas J Sweet
*Assistant Examiner* — William Chou
(74) *Attorney, Agent, or Firm* — Scully, Scott, Murphy & Presser, P.C.

(57) ABSTRACT

An endoscope apparatus includes an excitation-light radiation unit; a fluorescence-image acquisition unit; a fluorescence-spectrum storage unit; a density computation unit, an image combining portion; and an image display portion; wherein when coefficients at wavelengths of fluorescent components obtained from the fluorescence spectra in the storage unit, and when intensities of fluorescence images at the wavelengths acquired by the acquisition unit, the density computation unit calculates the densities of the fluorescent components from an equation, and when the densities are calculated, in accordance with a change in the value of an exposure condition item during acquisition of the fluorescence image at a wavelength, the density computation unit changes the coefficients at the wavelength using the ratio of the value after the change to the value of the exposure condition items under the reference exposure conditions has been made.

9 Claims, 26 Drawing Sheets

(56) References Cited

U.S. PATENT DOCUMENTS

| | | | |
|---|---|---|---|
| 8,300,093 B2 * | 10/2012 | Ayame et al. | 348/71 |
| 8,606,350 B2 * | 12/2013 | Ishihara | 600/476 |
| 2002/0138008 A1 * | 9/2002 | Tsujita et al. | 600/473 |
| 2008/0015446 A1 | 1/2008 | Mahmood et al. | |
| 2008/0039697 A1 | 2/2008 | Morishita | |
| 2013/0041267 A1 * | 2/2013 | Ntziachristos et al. | 600/476 |

* cited by examiner

DISTRIBUTION IMAGE OF
FLUORESCENT COMPONENT 1

FLUORESCENT COMPONENT 1

DISTRIBUTION IMAGE OF
FLUORESCENT COMPONENT 2

DISTRIBUTION IMAGE OF
FLUORESCENT COMPONENT 3

FLUORESCENT COMPONENT 3

WHEN BRIGHTNESSES OF INDIVIDUAL FLUORESCENT COMPONENTS ARE THE SAME

WHEN BRIGHTNESSES OF INDIVIDUAL FLUORESCENT COMPONENTS ARE DIFFERENT CONSIDERABLY

FIG. 7C
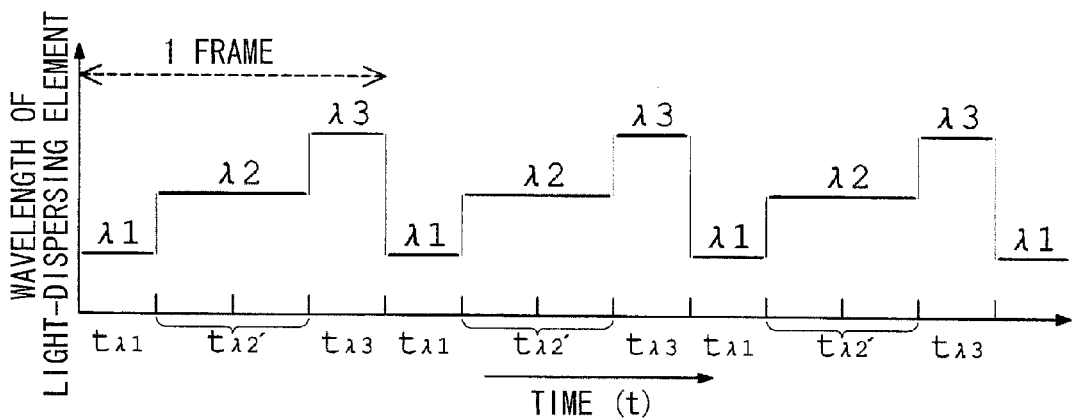
FIG. 7D
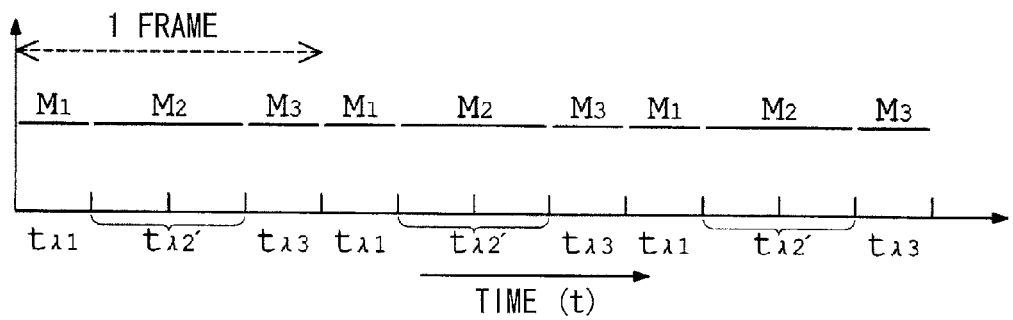
FIG. 7E
$$\begin{pmatrix} a_1(\lambda 1) & a_2(\lambda 1) & a_3(\lambda 1) \\ a_1(\lambda 2) \times \alpha_{21} & a_2(\lambda 2) \times \alpha_{21} & a_3(\lambda 2) \times \alpha_{21} \\ a_1(\lambda 3) & a_2(\lambda 3) & a_3(\lambda 3) \end{pmatrix} \begin{pmatrix} D_1 \\ D_2 \\ D_3 \end{pmatrix} = \begin{pmatrix} I_{all}(\lambda 1) \\ I_{all}(\lambda 2) \\ I_{all}(\lambda 3) \end{pmatrix} \cdots (1a')$$
WHERE, $\alpha_{21} = t_{\lambda 2'} / t_{\lambda 2}$

FIG. 8A

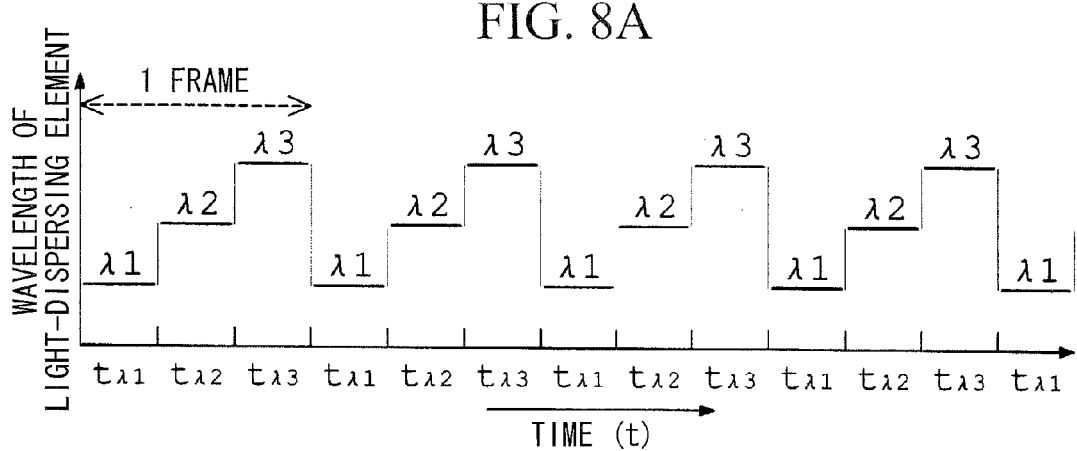

FIG. 8B

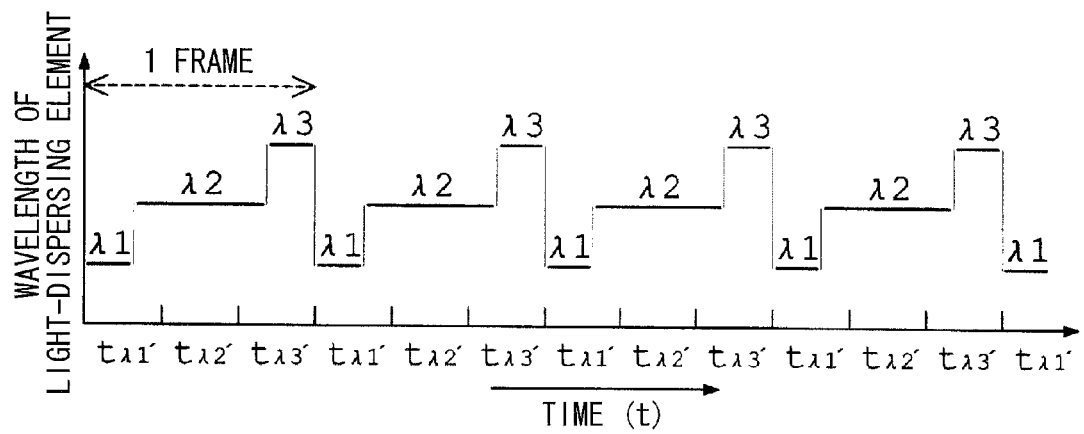

FIG. 8C $$\begin{pmatrix} a_1(\lambda 1) \times \alpha_{12} & a_2(\lambda 1) \times \alpha_{12} & a_3(\lambda 1) \times \alpha_{12} \\ a_1(\lambda 2) \times \alpha_{22} & a_2(\lambda 2) \times \alpha_{22} & a_3(\lambda 2) \times \alpha_{22} \\ a_1(\lambda 3) \times \alpha_{32} & a_2(\lambda 3) \times \alpha_{32} & a_3(\lambda 3) \times \alpha_{32} \end{pmatrix} \begin{pmatrix} D_1 \\ D_2 \\ D_3 \end{pmatrix} = \begin{pmatrix} I_{all}(\lambda 1) \\ I_{all}(\lambda 2) \\ I_{all}(\lambda 3) \end{pmatrix} \cdots (1b')$$

WHERE, $\alpha_{12} = t_{\lambda 1'}/t_{\lambda 1}$
$\alpha_{22} = t_{\lambda 2'}/t_{\lambda 2}$
$\alpha_{32} = t_{\lambda 3'}/t_{\lambda 3}$ FIG. 9A
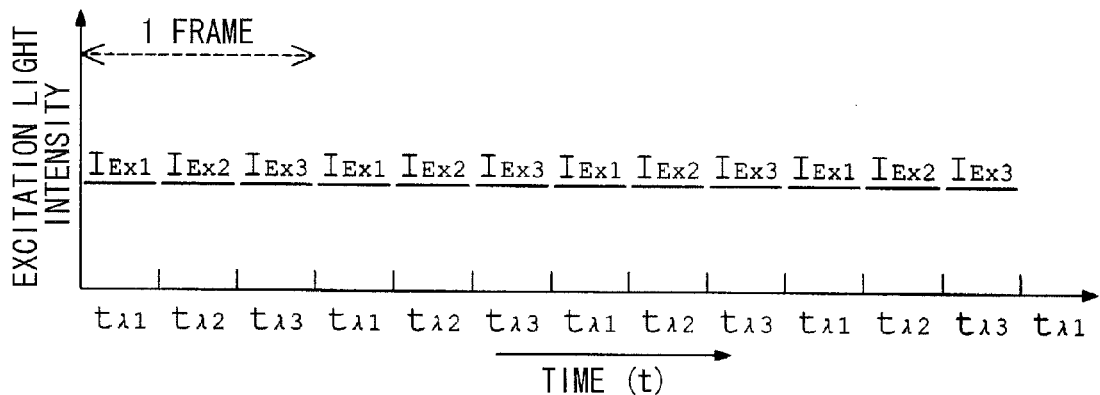
FIG. 9B
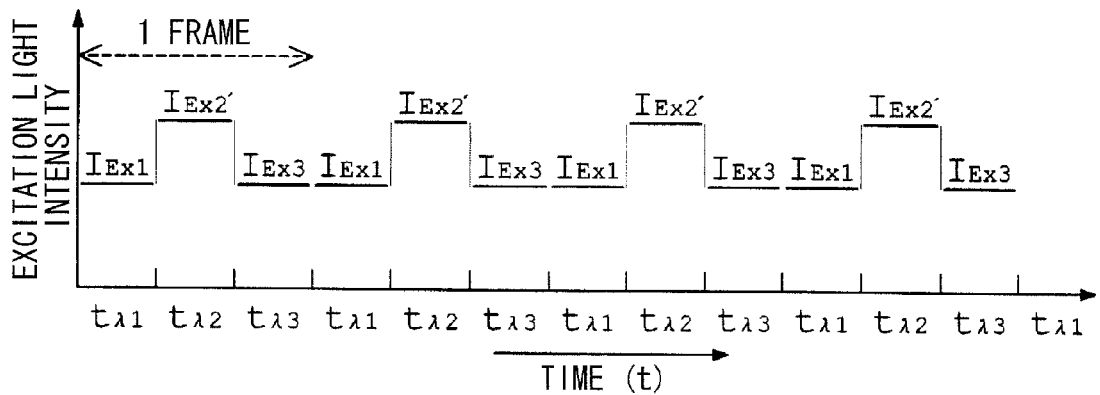
FIG. 9C
$$\begin{pmatrix} a_1(\lambda 1) & a_2(\lambda 1) & a_3(\lambda 1) \\ a_1(\lambda 2) \times \alpha_{23} & a_2(\lambda 2) \times \alpha_{23} & a_3(\lambda 2) \times \alpha_{23} \\ a_1(\lambda 3) & a_2(\lambda 3) & a_3(\lambda 3) \end{pmatrix} \begin{pmatrix} D1 \\ D2 \\ D3 \end{pmatrix} = \begin{pmatrix} I_{all}(\lambda 1) \\ I_{all}(\lambda 2) \\ I_{all}(\lambda 3) \end{pmatrix} \cdots (1c')$$
WHERE, $\alpha_{23} = I_{Ex2'} / I_{Ex2}$

FIG. 10A

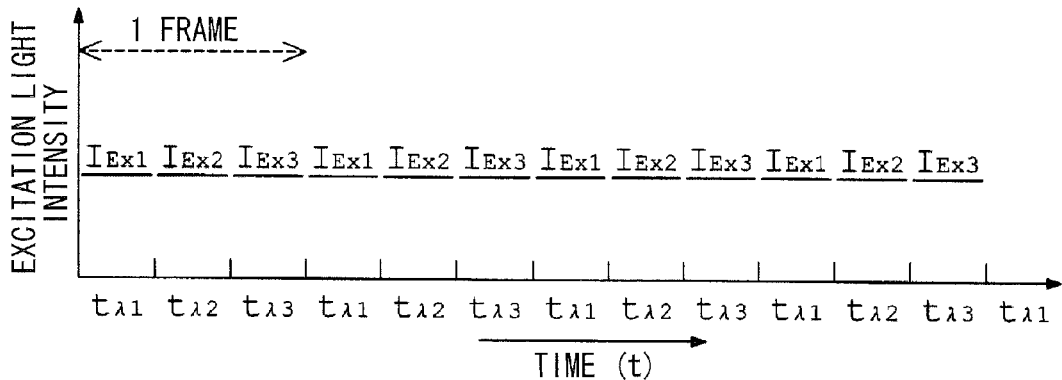

FIG. 10B

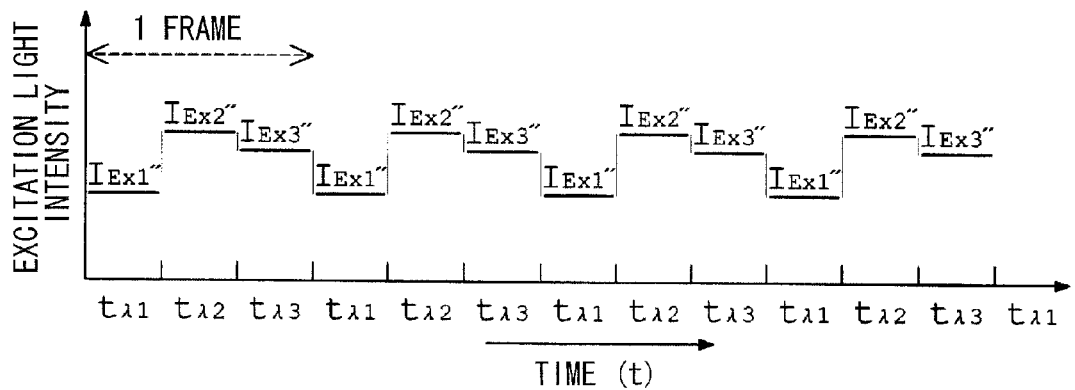

FIG. 10C $$\begin{pmatrix} a_1(\lambda 1) \times \alpha_{14} & a_2(\lambda 1) \times \alpha_{14} & a_3(\lambda 1) \times \alpha_{14} \\ a_1(\lambda 2) \times \alpha_{24} & a_2(\lambda 2) \times \alpha_{24} & a_3(\lambda 2) \times \alpha_{24} \\ a_1(\lambda 3) \times \alpha_{34} & a_2(\lambda 3) \times \alpha_{34} & a_3(\lambda 3) \times \alpha_{34} \end{pmatrix} \begin{pmatrix} D1 \\ D2 \\ D3 \end{pmatrix} = \begin{pmatrix} I_{all}(\lambda 1) \\ I_{all}(\lambda 2) \\ I_{all}(\lambda 3) \end{pmatrix} \cdots (1d')$$

WHERE, $\alpha_{14} = I_{Ex1}'' / I_{Ex1}$
$\alpha_{24} = I_{Ex2}'' / I_{Ex2}$
$\alpha_{34} = I_{Ex3}'' / I_{Ex3}$ FIG. 11A
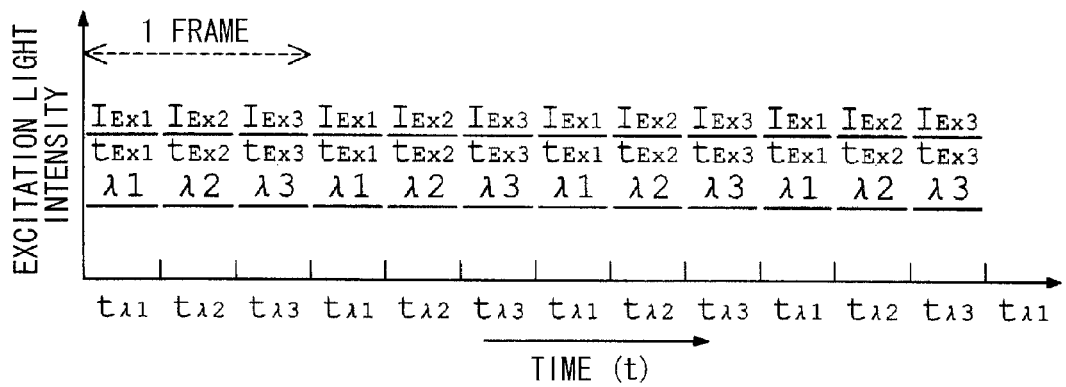
FIG. 11B
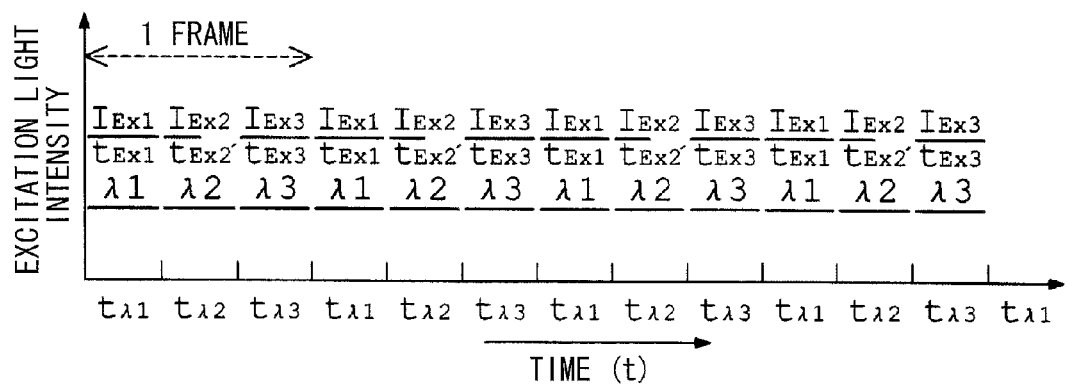
FIG. 11C
$$\begin{pmatrix} a_1(\lambda 1) & a_2(\lambda 1) & a_3(\lambda 1) \\ a_1(\lambda 2) \times \alpha_{25} & a_2(\lambda 2) \times \alpha_{25} & a_3(\lambda 2) \times \alpha_{25} \\ a_1(\lambda 3) & a_2(\lambda 3) & a_3(\lambda 3) \end{pmatrix} \begin{pmatrix} D1 \\ D2 \\ D3 \end{pmatrix} = \begin{pmatrix} I_{all}(\lambda 1) \\ I_{all}(\lambda 2) \\ I_{all}(\lambda 3) \end{pmatrix} \cdots (1e')$$
WHERE, $\alpha_{25} = t_{Ex2'} / t_{Ex2}$ FIG. 12A
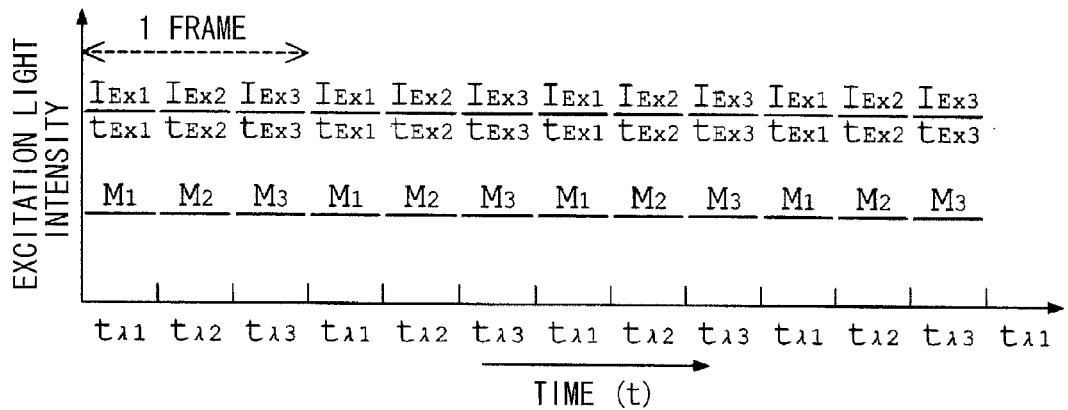
FIG. 12B
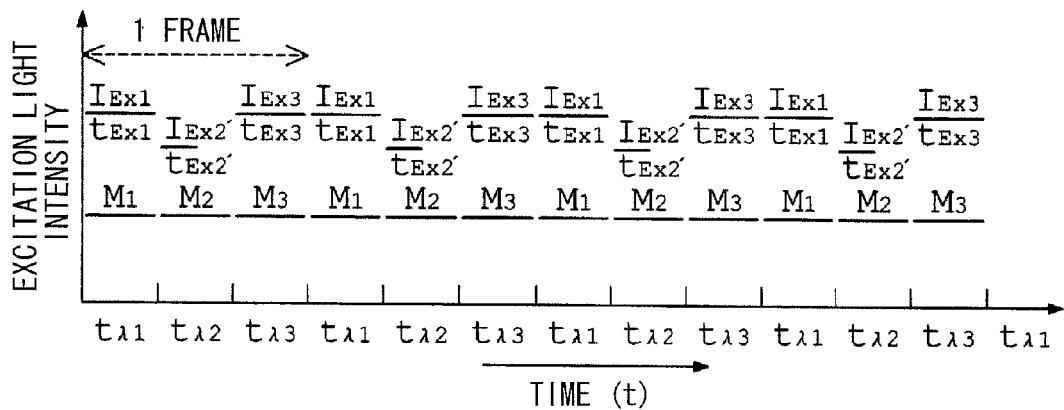
FIG. 12C
$$\begin{pmatrix} a_1(\lambda 1) & a_2(\lambda 1) & a_3(\lambda 1) \\ a_1(\lambda 2) \times \alpha_{26} & a_2(\lambda 2) \times \alpha_{26} & a_3(\lambda 2) \times \alpha_{26} \\ a_1(\lambda 3) & a_2(\lambda 3) & a_3(\lambda 3) \end{pmatrix} \begin{pmatrix} D_1 \\ D_2 \\ D_3 \end{pmatrix} = \begin{pmatrix} I_{all}(\lambda 1) \\ I_{all}(\lambda 2) \\ I_{all}(\lambda 3) \end{pmatrix} \cdots (1f')$$
WHERE, $\alpha_{26} = (I_{Ex2'}/I_{Ex2}) \times (t_{Ex2'}/t_{Ex2})$ FIG. 13A
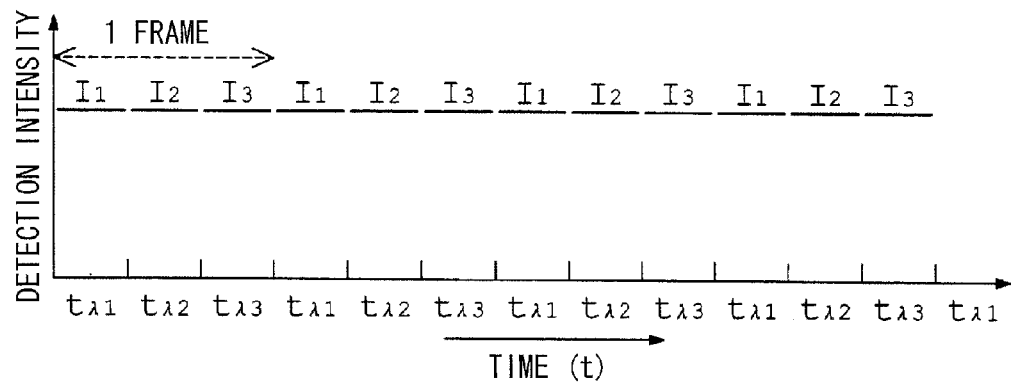
FIG. 13B
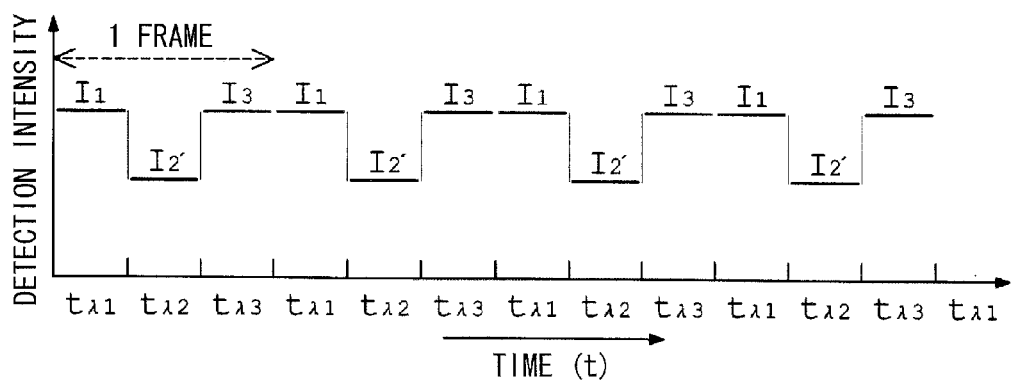
FIG. 13C
$$\begin{pmatrix} a_1(\lambda 1) & a_2(\lambda 1) & a_3(\lambda 1) \\ a_1(\lambda 2) \times \alpha_{27} & a_2(\lambda 2) \times \alpha_{27} & a_3(\lambda 2) \times \alpha_{27} \\ a_1(\lambda 3) & a_2(\lambda 3) & a_3(\lambda 3) \end{pmatrix} \begin{pmatrix} D_1 \\ D_2 \\ D_3 \end{pmatrix} = \begin{pmatrix} I_{a11}(\lambda 1) \\ I_{a11}(\lambda 2) \\ I_{a11}(\lambda 3) \end{pmatrix} \cdots (1g')$$
WHERE, $\alpha_{27} = I_2'/I_2$ FIG. 14A
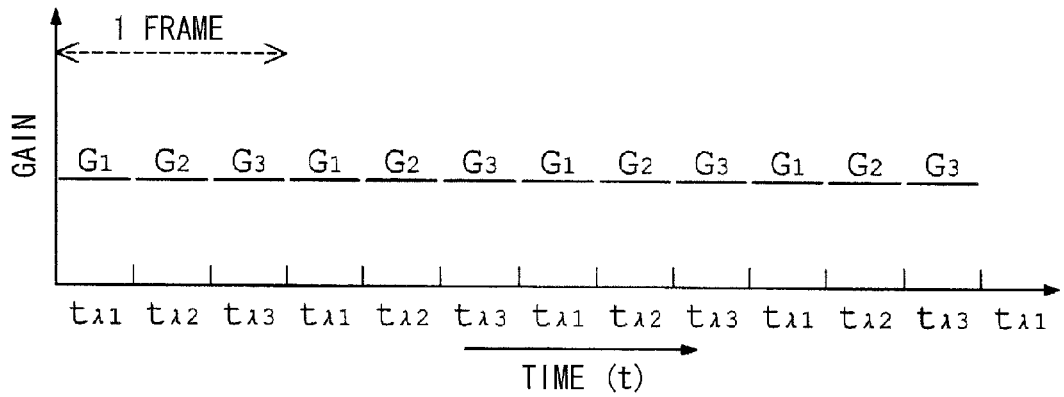
FIG. 14B
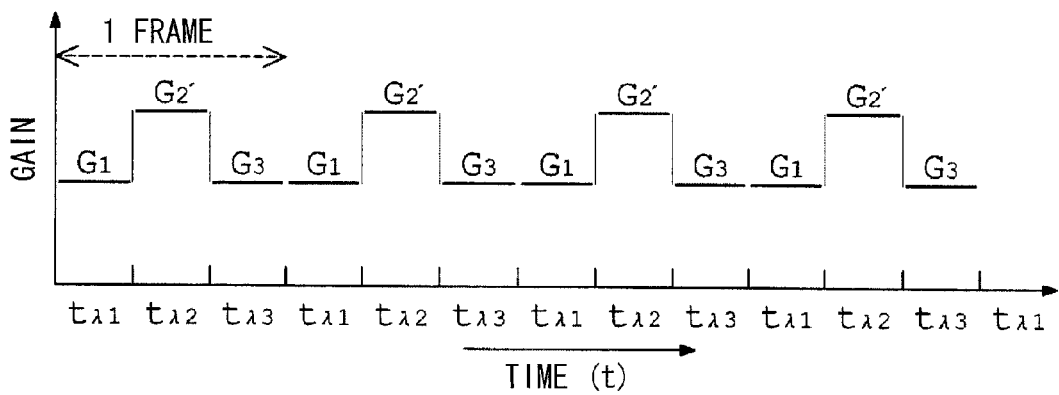
FIG. 14C
$$\begin{pmatrix} a_1(\lambda 1) & a_2(\lambda 1) & a_3(\lambda 1) \\ a_1(\lambda 2) \times \alpha_{28} & a_2(\lambda 2) \times \alpha_{28} & a_3(\lambda 2) \times \alpha_{28} \\ a_1(\lambda 3) & a_2(\lambda 3) & a_3(\lambda 3) \end{pmatrix} \begin{pmatrix} D_1 \\ D_2 \\ D_3 \end{pmatrix} = \begin{pmatrix} I_{all}(\lambda 1) \\ I_{all}(\lambda 2) \\ I_{all}(\lambda 3) \end{pmatrix} \cdots (1h')$$
WHERE, $\alpha_{28} = G_2' / G_2$ FIG. 17A
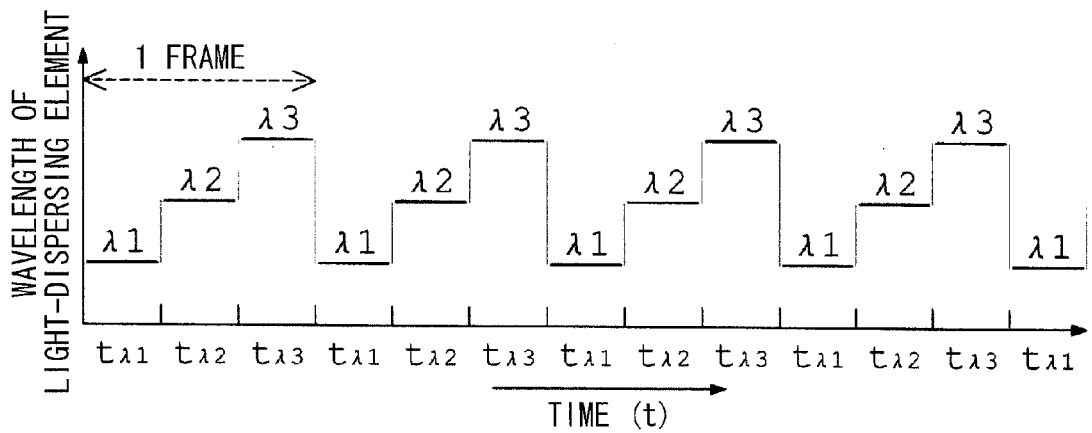
FIG. 17B
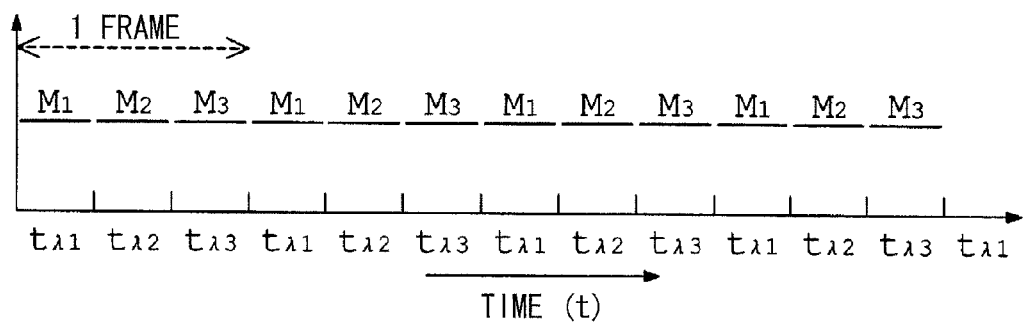
FIG. 17C
$$\begin{pmatrix} a_1(\lambda 1) & a_2(\lambda 1) & a_3(\lambda 1) \\ a_1(\lambda 2) & a_2(\lambda 2) & a_3(\lambda 2) \\ a_1(\lambda 3) & a_2(\lambda 3) & a_3(\lambda 3) \end{pmatrix} \begin{pmatrix} D1 \\ D2 \\ D3 \end{pmatrix} = \begin{pmatrix} I_{all}(\lambda 1) \\ I_{all}(\lambda 2) \\ I_{all}(\lambda 3) \end{pmatrix}$$

DISTRIBUTION IMAGE OF
FLUORESCENT COMPONENT 1

DISTRIBUTION IMAGE OF
FLUORESCENT COMPONENT 2

A: ACQUIRED SPECTRAL IMAGE

DISTRIBUTION IMAGE OF
FLUORESCENT COMPONENT 1

DISTRIBUTION IMAGE OF
FLUORESCENT COMPONENT 2

B: IMAGE AFTER UNMIXING PROCESSING

FLUORESCENCE-ENDOSCOPE APPARATUS

CROSS REFERENCE TO RELATED APPLICATIONS

This is a continuation-in-part of International Application PCT/JP2011/080158, with an international filing date of Dec. 27, 2011, which is hereby incorporated by reference herein in its entirety.

BACKGROUND OF THE INVENTION

1. Field of the Invention

The present invention relates to a fluorescence-endoscope apparatus that acquires a plurality of types of images of fluorescence generated by biological tissue containing a plurality of types of fluorescent components, whose maximum-fluorescence wavelengths are different and whose fluorescence wavelengths overlap in at least parts of the wavelength ranges, and that separately displays the plurality of types of fluorescent components present in the biological tissue using the acquired fluorescence images.

2. Description of Related Art

In molecular imaging diagnosis using fluorescence-endoscope apparatuses, it is effective to perform fluorescence-extraction processing using a so-called UNMIXING technique that removes autofluorescence noise originating from biological subjects (tissue, residues, and so forth), to extract fluorescence coming from fluorescent probes. In order to improve the image quality S/N of the fluorescence image with low light intensity in the fluorescence-extraction processing using the UNMIXING technique, it is effective to allow the exposure time to be changed arbitrarily via a spectral image-acquisition unit provided with an etalon-type tunable light-dispersing element and a sensitive camera, for example.

Conventional fluorescence-endoscope apparatuses using the UNMIXING technique include, for example, the endoscope apparatus described in the following Publication of Japanese Patent No. 2008-43396.

In fluorescence-endoscope apparatuses that capture spectral images of a plurality of types of fluorescence, the longer the exposure time used, the lower the frame rate becomes.

The brightness of each fluorescent component (human tissue, residue, or fluorescence agent) present in the biological tissue of an observation target is not uniform.

Thus, for example, when a darker fluorescent component is present in the biological tissue, it is necessary to increase the exposure time so that the brightness of the fluorescence image of the darker fluorescent component is suitable for observation. However, if the exposure time for the fluorescence images of other fluorescent components present in the biological tissue is increased in a similar manner in accordance with the change made in the exposure time for the fluorescence image of the darker fluorescent component, the frame rate is greatly reduced. When the other fluorescent components present in the biological tissue are excessively bright and if the exposure time is increased further, the brightnesses of the fluorescence images of the excessively-brighter fluorescent components are saturated.

For example, when an excessively bright fluorescent component is present in the biological tissue, it is necessary to reduce the exposure time such that the brightness of the image of the excessively bright fluorescent component is suitable for observation. However, if the exposure time for the fluorescence images of the other fluorescent components present in the biological tissue is reduced in a similar manner in accordance with the change made in the exposure time for the fluorescence image of the excessively bright fluorescent component and if, for example, the other fluorescent components are darker, the fluorescence images of the darker fluorescent components become too dark to be detected.

Therefore, in fluorescence-extraction processing using the UNMIXING technique in the endoscope apparatus described in Publication of Japanese Patent No. 2008-43396, constant UNMIXING coefficients (component ratios of the fluorescent components) are used regardless of the exposure conditions, such as the exposure time etc. Thus, when the fluorescence image is detected by adjusting the exposure conditions, such as the exposure time etc., so that a suitable brightness is achieved for each fluorescence wavelength, the UNMIXING coefficients become unsuitable, and it is sometimes difficult to separate the fluorescent components suitably.

The fluorescence-endoscope apparatus using the conventional UNMIXING technique will be described with reference to an example where a sample containing three types of fluorescent components having different fluorescence wavelengths is subjected to spectroscopy.

FIGS. 15A and 15B are diagrams for explaining three types of fluorescent components 1 to 3 present in a sample, where FIG. 15A is a diagram conceptually showing the distribution of the fluorescent components 1 to 3 in the sample, and FIG. 15B is a diagram showing fluorescence spectra of the fluorescent components 1 to 3. FIGS. 16A to 16C are explanatory diagrams conceptually showing the distributions and brightnesses of spectral images acquired by an image acquisition apparatus through a tunable light-dispersing element, such as an etalon etc., in a fluorescence-endoscope apparatus, where FIG. 16A is a diagram showing a spectral image of the fluorescent component 1 at the maximum-fluorescence wavelength λ1, FIG. 16B is a diagram showing a spectral image of the fluorescent component 2 at the maximum-fluorescence wavelength λ2, and FIG. 16C is a diagram showing a spectral image of the fluorescent component 3 at the maximum-fluorescence wavelength λ3. $I_{all}(\lambda 1)$, $I_{all}(\lambda 2)$, and $I_{all}(\lambda 3)$ are signal intensities that are detected at an arbitrary common pixel Pi in each of the spectral images shown in FIGS. 16A to 16C. FIGS. 17A to 17C are diagrams showing example exposure timings for spectral images of the individual fluorescent components 1 to 3 at the maximum-fluorescence wavelengths λ1 to λ3, where FIG. 17A is a diagram showing transmission-switching timings of the maximum-fluorescence wavelengths λ1 to λ3 of the three types of fluorescent components 1 to 3 by a tunable light-dispersing element, FIG. 17B is a diagram showing image-acquisition timings of the fluorescence wavelengths λ1 to λ3 that are acquired by an image acquisition apparatus, and FIG. 17C is a diagram showing an example of a matrix equation for calculating densities D1 to D3 of the fluorescent components 1 to 3 using the conventional UNMIXING technique in a spectral image in which fluorescence signals generated by the fluorescent components 1 to 3 coexist. In FIGS. 17A to 17C, $t\lambda_1$ to $t\lambda_3$ are exposure times at which the individual fluorescence wavelengths λ1 to λ3 are spectrally separated through a tunable light-dispersing element etc., and $M_1$ to $M_3$ are memories that store the data of the respective fluorescence wavelengths λ1 to λ3, which have been spectrally separated through the tunable light-dispersing element etc., acquired by individual image acquisition apparatuses.

Image acquisition using the image acquisition apparatus is performed on a sample, serving as a target, in which, as shown in FIG. 15B, the fluorescent component 1 having the maximum-fluorescence wavelength at the wavelength λ1, the fluorescent component 2 having the maximum-fluorescence wavelength at the wavelength λ2, and the fluorescent component 3 having the maximum-fluorescence wavelength at the wavelength λ3 are individually distributed in the locations shown in FIG. 15A, by transmitting the fluorescence wavelengths λ1 to λ3 generated by the individual fluorescent components 1 to 3 through the tunable light-dispersing element in a time-division manner.

At this time, as shown in FIGS. 16A to 16C, although the intensities of the fluorescence signals from the individual fluorescent components 1 to 3 are different, the spectral images at the individual fluorescence wavelengths are images that contain the fluorescence signals generated by the three types of fluorescent components in a mixed manner. In other words, in these spectral images, fluorescence signals emitted from the fluorescent components 1 to 3 are not separated.

Here, it is assumed that fluorescence-extraction processing using the conventional UNMIXING technique described in Publication of Japanese Patent No. 2008-43396 is performed on a spectral image containing the fluorescence signals from the fluorescent components 1 to 3 in a mixed manner.

In the fluorescence-extraction processing using the conventional UNMIXING technique, the UNMIXING coefficients (the component ratios of the fluorescent components) of the fluorescence spectra of the three types of fluorescent components 1 to 3 present in the sample at the individual normalized densities are stored in advance in a predetermined storage medium.

Then, the UNMIXING coefficients (the component ratios of the fluorescent components) of the fluorescence spectra of the fluorescent components 1 to 3 at the individual normarized densities stored in the predetermined storage medium and the intensities $I_{all}(\lambda 1)$ to $I_{all}(\lambda 3)$ in the fluorescence images at the individual fluorescence wavelengths λ1 to λ3 that are detected are used to calculate the densities D1 to D3 of the fluorescent components 1 to 3 based on the matrix equation shown in FIG. 17C.

In this way, in the fluorescence-endoscope apparatus using the conventional UNMIXING technique, it is possible to obtain distribution images of the individual fluorescent components by performing UNMIXING on the spectral images using the spectra of the individual fluorescent components.

FIGS. 18A to 18G are diagrams showing image processing after the UNMIXING processing, where FIG. 18A is a distribution image of the fluorescent component 1 after the UNMIXING processing, FIG. 18B is a diagram showing a state in which a predetermined color is assigned to a distributed region of the fluorescent component 1 in the distribution image in FIG. 18A, FIG. 18C is a distribution image of the fluorescent component 2 after the UNMIXING processing, FIG. 18D is a diagram showing a state in which a predetermined color is assigned to a distributed region of the fluorescent component 2 in the distribution image in FIG. 18C, FIG. 18E is a distribution image of the fluorescent component 3 after the UNMIXING processing, FIG. 18F is a diagram showing a state in which a predetermined color is assigned to a distributed region of the fluorescent component 3 in the distribution image in FIG. 18E, and FIG. 18G is a diagram showing a state in which the distribution images shown in FIGS. 18B, 18D, and 18F are combined into one image.

In accordance with the brightnesses of the individual fluorescent components; their tendency to accumulate in a biological subject, serving as a sample; their transportability to a lesion, serving as a sample; metabolic properties in a biological subject (such as time); time (assessment time) and timing before performing measurement after introducing a fluorophor into the biological subject; and so forth, the fluorescence intensities (brightnesses) at the maximum-fluorescence wavelength are different for every fluorescent component in the sample.

For example, even with the fluorescent components 1 to 3 having the fluorescence spectral properties shown in FIG. 19A, as shown in FIG. 19B, the fluorescence intensity of the fluorescent component 2 at the maximum-fluorescence wavelength λ2 may be different.

In such a case, it is difficult to detect a darker fluorescent component if changing the exposure conditions, including the exposure time etc., such as increasing the exposure time for the fluorescence image of the fluorescent component 2 in FIGS. 19A and 19B, is not performed properly. Because the intensity detected from the darker fluorescent component 2 at the fluorescence wavelength λ2 is weak, the detected signal tends to be affected by noise, and it is difficult to obtain the correct density even when the UNMIXING processing is performed.

However, for example, if the exposure time is evenly increased for the fluorescence images of all fluorescent components at the maximum-fluorescence wavelength in accordance with a suitable adjustment of the exposure time for the fluorescent component that is dark at the maximum-fluorescence wavelength, the frame rate is considerably reduced.

For the fluorescent component that is dark at the maximum-fluorescence wavelength, if only the exposure time for the fluorescence image at the maximum-fluorescence wavelength is increased, then the detection level of the fluorescence wavelengths of the other fluorescent components contained in the image varies, and a divergence from the UNMIXING coefficients (the component ratios of the fluorescent components) occurs, making separation of the fluorescent components difficult.

For example, in contrast to the situation shown in FIGS. 19A and 19B, in the case where the fluorescent component 2 is excessively bright at the maximum-fluorescence wavelength, the brightness of the image of the fluorescent component 2 is saturated if changing the exposure conditions, including the exposure time etc., such as reducing the exposure time for the fluorescence image of the fluorescent component 2, is not performed properly.

However, for example, if the exposure time is evenly decreased for the fluorescence images of all fluorescent components at the maximum-fluorescence wavelength in accordance with a suitable adjustment of the exposure time for the fluorescent component that is bright at the maximum-fluorescence wavelength, then the fluorescence images of the other fluorescent components at the maximum-fluorescence wavelength become darker, making it difficult to detect the darker fluorescent components, or the detected signal tends to be affected by noise, making it difficult to obtain the correct densities even if the UNMIXING processing is performed.

If only the exposure time for the fluorescence image at the maximum-fluorescence wavelength of the fluorescent component that is excessively-bright at the maximum-fluorescence wavelength is reduced, then the detection level of the fluorescence wavelengths of the other fluorescent components present in the image varies, and a divergence from the UNMIXING coefficients (the component ratios of the fluorescent components) occurs, making separation of the fluorescent components difficult.

As shown in FIG. 22B, when only the exposure time for the fluorescence image at the fluorescence wavelength λ2 shown in FIG. 21B is increased, not only the fluorescent component 2, but also the other components, such as the fluorescent component 1 and the fluorescent component 3, are detected at high brightness.

In such a case, even if the UNMIXING processing is performed on the acquired spectral images, the component ratios of the actual fluorescent components become different from the UNMIXING coefficients that have been stored in a memory etc. in advance. Therefore, even if the densities D1 to D3 of the fluorescent components 1 to 3 are obtained using the matrix equation shown in FIG. 17C, to which matrix equation (13) above has been applied, as shown in FIGS. 23B to 23D, it is difficult to acquire distribution images that are separated into the individual fluorescent components.

A fluorescence-endoscope apparatus of one aspect of the present invention is a fluorescence-endoscope apparatus that radiates excitation light onto biological tissue containing a plurality of types of fluorescent components, whose maximum-fluorescence wavelengths are different and whose fluorescence wavelengths overlap in at least parts of the wavelength ranges, that acquires a plurality of types of images of fluorescence generated by the biological tissue, and that displays, in a separated manner, the plurality of types of fluorescent components present in the biological tissue using the acquired fluorescence images, comprising: a light source portion that emits at least one type of excitation light that excites the plurality of types of fluorescent components; a fluorescence image capturing unit that acquires the images of fluorescence generated by the biological tissue for every n types [where, m≤n] of wavelengths λ1 to wavelength λn; a fluorescence-spectrum storage unit that records fluorescence spectra of m types [where, 2≤m] of individual fluorescent component 1 to fluorescent component m present in the biological tissue at normalized densities under reference exposure conditions; a fluorescent-component-density computation unit that obtains densities of the individual fluorescent components present in the biological tissue for all pixels in the fluorescence images by performing computation using the fluorescence spectra at the individual normalized densities of the fluorescent component 1 to fluorescent component m under the reference exposure conditions that are stored in the fluorescence-spectrum storage unit and the fluorescence images for every wavelength λ1 to wavelength λn acquired by the fluorescence image capturing unit; a fluorescence-image combining portion that forms distribution images of the individual fluorescent components on the basis of the density of the individual fluorescent components obtained by the fluorescent-component-density computation unit, assigns predetermined colors corresponding to the individual fluorescent components to the formed distribution images of the individual fluorescent components, and combines the distribution images to which the predetermined colors are assigned into one image; and an image display portion that displays the image that has been combined by the fluorescence-image combining portion, wherein, when a1 (λ1) to a1(λn) to am(λ1) to am(λn) are defined as coefficients at the wavelength λ1 to wavelength λn of the fluorescent component 1 to fluorescent component m at the individual normalized densities under the reference exposure conditions, which are obtained from the fluorescence spectra, stored in the fluorescence-spectrum storage unit, of the fluorescent component 1 to fluorescent component m at the individual normalized densities under the reference exposure conditions, $I_{all}(\lambda 1)$ to $I_{all}(\lambda n)$ are defined as intensities of the fluorescence images at the wavelength λ1 to wavelength λn acquired by the fluorescence image capturing unit, and D1 to Dm are defined as the densities of the fluorescent component 1 to fluorescent component m, the fluorescent-component-density computation unit calculates, for all pixels, the density D1 of the fluorescent component 1 to the density Dm of the fluorescent component m in each pixel in the fluorescence images using Equation (1) below, and wherein the fluorescent-component-density computation unit: checks if the reference exposure conditions of an exposure condition item have been changed; and if a value of a predetermined exposure condition item has been changed when the fluorescence image at least one wavelength λx among the wavelength λ1 to wavelength λn is acquired by the fluorescence image capturing unit, in accordance with the change, when the density D1 of the fluorescent component 1 to the density Dm of the fluorescent component m are calculated using Equation (1), changes the coefficients a1 (λx) to am(λx) at the wavelength λx of the fluorescent component 1 to fluorescent component m at the normalized density under the reference exposure conditions using the ratio of the value of the changed predetermined exposure condition item to the value of the predetermined exposure condition item under the reference exposure conditions when the fluorescence image at the wavelength λx is acquired by the fluorescence image capturing unit:

[Expression 5]

$$\begin{pmatrix} D1 \\ \vdots \\ Dm \end{pmatrix} = \begin{pmatrix} a1(\lambda 1) & \cdots & am(\lambda 1) \\ \vdots & \vdots & \vdots \\ a1(\lambda n) & \cdots & am(\lambda n) \end{pmatrix}^{-1} \begin{pmatrix} I_{all}(\lambda 1) \\ \vdots \\ I_{all}(\lambda n) \end{pmatrix} \quad 式(1)$$

Equation (1).

In the above-mentioned fluorescence-endoscope apparatus, if the exposure time has been changed when the fluorescence image at the predetermined wavelength λx among the wavelength λ1 to wavelength λn is acquired by the fluorescence image capturing unit, in accordance with the change, when the density D1 of the fluorescent component 1 to the density Dm of the fluorescent component m are calculated using Equation (1), the fluorescent-component-density computation unit may multiply the coefficients a1 (λx) to am(λx) at the predetermined wavelength λx of the fluorescent component 1 to fluorescent component m at the normalized density under the reference exposure conditions by the ratio of the changed exposure time to the exposure time under the reference exposure conditions when the fluorescence image at the predetermined wavelength λx is acquired by the fluorescence image capturing unit.

In the above-mentioned fluorescence-endoscope apparatus, if the exposure times have been changed while keeping the frame rate constant when the fluorescence images at the individual wavelengths of the wavelength λ1 to wavelength λn are acquired by the fluorescence image capturing unit, in accordance with the change, when the density D1 of the fluorescent component 1 to the density Dm of the fluorescent component m are calculated using Equation (1), the fluorescent-component-density computation unit may multiply the coefficients a1 (λ1) to am(λ1) to a1 (λn) to am(λn) at individual wavelengths among the wavelength λ1 to wavelength λn of the fluorescent component 1 to fluorescent component m at the normalized density under the reference exposure conditions by the ratio of the changed exposure time to the exposure time under the reference exposure conditions when the fluorescence images at the individual wavelengths of the wavelength λ1 to wavelength λn are acquired by the fluorescence image capturing unit.

In the above-mentioned fluorescence-endoscope apparatus, if the intensity of the excitation light that excites the predetermined wavelength λx has been changed when the fluorescence image at the predetermined wavelength λx among the wavelength λ1 to wavelength λn is acquired by the fluorescence image capturing unit, in accordance with the change, when the density D1 of the fluorescent component 1 to the density Dm of the fluorescent component m are calculated using Equation (1), the fluorescent-component-density computation unit may multiply the coefficients a1 (λx) to am(λx) at the wavelength λx of the fluorescent component 1 to fluorescent component m at the normalized density under the reference exposure conditions by the ratio of the changed intensity of the excitation light that excites the predetermined wavelength λx to the intensity of the excitation light that excites the predetermined wavelength λx under the reference exposure conditions when the fluorescence image at the predetermined wavelength λx is acquired by the fluorescence image capturing unit.

In the above-mentioned fluorescence-endoscope apparatus, if the intensities of the excitation light beams that excite the individual wavelengths have been changed when the fluorescence images at the individual wavelengths of the wavelength λ1 to wavelength λn are acquired by the fluorescence image capturing unit, in accordance with the change, when the density D1 of the fluorescent component 1 to the density Dm of the fluorescent component m are calculated using Equation (1), the fluorescent-component-density computation unit may multiply the coefficients a1 (λ1) to am(λ1) to a1 (λn) to am(λn) at individual wavelengths among the wavelengths λ1 to λn of the fluorescent component 1 to fluorescent component m at the normalized density under the reference exposure conditions by the ratios of the changed intensities of the excitation light beams that excite the individual wavelengths to the intensities of the excitation light beams that excite the individual wavelengths under the reference exposure conditions when the fluorescence images at the individual wavelengths of the wavelength λ1 to wavelength λn are acquired by the fluorescence image capturing unit.

In the above-mentioned fluorescence-endoscope apparatus, if the excitation time of the excitation light that excites the predetermined wavelength λx has been changed when the fluorescence image at predetermined wavelength λx among the wavelength λ1 to wavelength λn is acquired by the fluorescence image capturing unit, in accordance with the change, when the density D1 of the fluorescent component 1 to the density Dm of the fluorescent component m are calculated using Equation (1), the fluorescent-component-density computation unit may multiply the coefficients a1 (λx) to am(λx) at the wavelength λx of the fluorescent component 1 to fluorescent component m at the normalized density under the reference exposure conditions by the ratio of the changed excitation time of the excitation light that excites the predetermined wavelength λx to the excitation time of the excitation light that excites the predetermined wavelength λx under the reference exposure conditions when the fluorescence image at the predetermined wavelength λx is acquired by the fluorescence image capturing unit.

In the above-mentioned fluorescence-endoscope apparatus, if the intensity and the excitation time of the excitation light that excites the predetermined wavelength λx have been changed when the fluorescence image at predetermined wavelength λx among the wavelength λ1 to wavelength λn is acquired by the fluorescence image capturing unit, in accordance with the change, when the density D1 of the fluorescent component 1 to the density Dm of the fluorescent component m are calculated using Equation (1), the fluorescent-component-density computation unit may multiply the coefficients a1 (λx) to am(λx) at the wavelength λx of the fluorescent component 1 to fluorescent component m at the normalized density under the reference exposure conditions by the ratios of the changed intensity and the changed excitation time of the excitation light that excites the predetermined wavelength λx to the intensity and the excitation time of the excitation light that excites the predetermined wavelength λx under the reference exposure conditions when the fluorescence image at the predetermined wavelength λx is acquired by the fluorescence image capturing unit.

In the above-mentioned fluorescence-endoscope apparatus, if a detection intensity has been changed when the fluorescence image at the predetermined wavelength λx among the wavelength λ1 to wavelength λn is acquired by the fluorescence image capturing unit, in accordance with the change, when the density D1 of the fluorescent component 1 to the density Dm of the fluorescent component m are calculated using Equation (1), the fluorescent-component-density computation unit may multiply the coefficients a1 (λx) to am(λx) at the predetermined wavelength λx of the fluorescent component 1 to fluorescent component m at the normalized density under the reference exposure conditions by the ratio of the changed detection intensity to the detection intensity under the reference exposure conditions when the fluorescence image at the predetermined wavelength λx is acquired by the fluorescence image capturing unit.

In the above-mentioned fluorescence-endoscope apparatus, if a gain has been changed when the fluorescence image at the predetermined wavelength λx among the wavelength λ1 to wavelength λn is acquired by the fluorescence image capturing unit, in accordance with the change, when the density D1 of the fluorescent component 1 to the density Dm of the fluorescent component m are calculated using Equation (1), the fluorescent-component-density computation unit may multiply the coefficients a1 (λx) to am(λx) at the predetermined wavelength λx of the fluorescent component 1 to fluorescent component m at the normalized density under the reference exposure conditions by the ratio of the changed gain to the gain under the reference exposure conditions when the fluorescence image at the predetermined wavelength λx is acquired by the fluorescence image capturing unit.

BRIEF DESCRIPTION OF THE SEVERAL VIEWS OF THE DRAWINGS

FIG. 7C is an explanatory diagram showing the exposure conditions in the fluorescence-endoscope apparatus of Example 1 and computation performed by the fluorescent-component-density computation unit $13d_2$, and is a diagram showing, in time-series, the light in each of the wavelength ranges selected by and transmitted through the tunable light-dispersing element $12b_4$ under the exposure conditions in Example 1.

FIG. 7D is an explanatory diagram showing the exposure conditions in the fluorescence-endoscope apparatus of Example 1 and computation performed by the fluorescent-component-density computation unit $13d_2$, and is a diagram showing, in time-series, the light in each of the wavelength ranges that has been, at substantially the same time as in FIG. 7C, photoelectrically converted through the image acquisition device $12b_5$ and stored in each of the frame memories $13c_1$, $13c$, and $13c_3$.

FIG. 7E is an explanatory diagram showing the exposure conditions in the fluorescence-endoscope apparatus of Example 1 and computation performed by the fluorescent-component-density computation unit $13d_2$, and is a diagram showing a matrix equation that is used in the UNMIXING processing performed by the fluorescent-component-density computation unit $13d_2$ under the exposure conditions shown in FIGS. 7C and 7D.

FIG. 8A is an explanatory diagram showing the exposure conditions in the fluorescence-endoscope apparatus of Example 2 and computation performed by the fluorescent-component-density computation unit $13d_2$, and is a diagram showing, in time-series, the light in each of the wavelength ranges selected by and transmitted through the tunable light-dispersing element $12b_4$ under the reference exposure conditions.

FIG. 8B is an explanatory diagram showing the exposure conditions in the fluorescence-endoscope apparatus of Example 2 and computation performed by the fluorescent-component-density computation unit $13d_2$, and is a diagram showing, in time-series, the light in each of the wavelength ranges selected by and transmitted through the tunable light-dispersing element $12b_4$ under the exposure conditions in Example 2.

FIG. 8C is an explanatory diagram showing the exposure conditions in the fluorescence-endoscope apparatus of Example 2 and computation performed by the fluorescent-component-density computation unit $13d_2$, and is a diagram showing a matrix equation that is used in the UNMIXING processing performed by the fluorescent-component-density computation unit $13d_2$ under the exposure conditions shown in FIG. 8B.

FIG. 9A is an explanatory diagram showing the exposure conditions in the fluorescence-endoscope apparatus of Example 3 and computation performed by the fluorescent-component-density computation unit $13d_2$, and is a diagram showing, in time-series, the intensity and the irradiation timing of each excitation light beam that excites the fluorescence wavelengths of the individual fluorescent components under the reference exposure conditions.

FIG. 9B is an explanatory diagram showing the exposure conditions in the fluorescence-endoscope apparatus of Example 3 and computation performed by the fluorescent-component-density computation unit $13d_2$, and is a diagram showing, in time-series, the intensity and the irradiation timing of each excitation light beam that excites the fluorescence wavelengths of the individual fluorescent components under the exposure conditions in Example 3.

FIG. 9C is an explanatory diagram showing the exposure conditions in the fluorescence-endoscope apparatus of Example 3 and computation performed by the fluorescent-component-density computation unit $13d_2$, and is a diagram showing a matrix equation that is used in the UNMIXING processing performed by the fluorescent-component-density computation unit $13d_2$ under the exposure conditions shown in FIG. 9B.

FIG. 10A is an explanatory diagram showing the exposure conditions in the fluorescence-endoscope apparatus of Example 4 and computation performed by the fluorescent-component-density computation unit $13d_2$, and is a diagram showing, in time-series, the intensity and the irradiation timing of each excitation light beam that excites the fluorescence wavelengths of the individual fluorescent components under the reference exposure conditions.

FIG. 10B is an explanatory diagram showing the exposure conditions in the fluorescence-endoscope apparatus of Example 4 and computation performed by the fluorescent-component-density computation unit $13d_2$, and is a diagram showing, in time-series, the intensity and the irradiation timing of each excitation light beam that excites the fluorescence wavelengths of the individual fluorescent components under the exposure conditions in Example 4.

FIG. 10O is an explanatory diagram showing the exposure conditions in the fluorescence-endoscope apparatus of Example 4 and computation performed by the fluorescent-component-density computation unit $13d_2$, and is a diagram showing a matrix equation that is used in the UNMIXING processing performed by the fluorescent-component-density computation unit $13d_2$ under the exposure conditions shown in FIG. 10B.

FIG. 11A is an explanatory diagram showing the exposure conditions in the fluorescence-endoscope apparatus of Example 5 and computation performed by the fluorescent-component-density computation unit $13d_2$, and is a diagram showing, in time-series, the intensity and the irradiation timing of each excitation light beam that excites the fluorescence wavelengths of the individual fluorescent components under the reference exposure conditions.

FIG. 11B is an explanatory diagram showing the exposure conditions in the fluorescence-endoscope apparatus of Example 5 and computation performed by the fluorescent-component-density computation unit $13d_2$, and is a diagram showing, in time-series, the intensity and the irradiation timing of each excitation light beam that excites the fluorescence wavelengths of the individual fluorescent components under the exposure conditions in Example 5.

FIG. 11C is an explanatory diagram showing the exposure conditions in the fluorescence-endoscope apparatus of Example 5 and computation performed by the fluorescent-component-density computation unit $13d_2$, and is a diagram showing a matrix equation that is used in the UNMIXING processing performed by the fluorescent-component-density computation unit $13d_2$ under the exposure conditions shown in FIG. 11B.

FIG. 12A is an explanatory diagram showing the exposure conditions in the fluorescence-endoscope apparatus of Example 6 and computation performed by the fluorescent-component-density computation unit $13d_2$, and is a diagram showing, in time-series, the intensity and the irradiation timing of each excitation light beam that excites the fluorescence wavelengths of the individual fluorescent components under the reference exposure conditions.

FIG. 12B is an explanatory diagram showing the exposure conditions in the fluorescence-endoscope apparatus of Example 6 and computation performed by the fluorescent-component-density computation unit $13d_2$, and is a diagram showing, in time-series, the intensity and the irradiation timing of each excitation light beam that excites the fluorescence wavelengths of the individual fluorescent components under the exposure conditions in Example 6.

FIG. 12C is an explanatory diagram showing the exposure conditions in the fluorescence-endoscope apparatus of Example 6 and computation performed by the fluorescent-component-density computation unit $13d_2$, and is a diagram showing a matrix equation that is used in the UNMIXING processing performed by the fluorescent-component-density computation unit $13d_2$ under the exposure conditions shown in FIG. 12B.

FIG. 13A is an explanatory diagram showing the exposure conditions in the fluorescence-endoscope apparatus of Example 7 and computation performed by the fluorescent-component-density computation unit $13d_2$, and is a diagram showing, in time-series, the intensity and the irradiation timing of each excitation light beam that excites the fluorescence wavelengths of the individual fluorescent components under the reference exposure conditions.

FIG. 13B is an explanatory diagram showing the exposure conditions in the fluorescence-endoscope apparatus of Example 7 and computation performed by the fluorescent-component-density computation unit $13d_2$, and is a diagram showing, in time-series, the intensity and the irradiation timing of each excitation light beam that excites the fluorescence wavelengths of the individual fluorescent components under the exposure conditions in Example 7.

FIG. 13C is an explanatory diagram showing the exposure conditions in the fluorescence-endoscope apparatus of Example 7 and computation performed by the fluorescent-component-density computation unit $13d_2$, and is a diagram showing a matrix equation that is used in the UNMIXING processing performed by the fluorescent-component-density computation unit $13d_2$ under the exposure conditions shown in FIG. 13B.

FIG. 14A is an explanatory diagram showing the exposure conditions in the fluorescence-endoscope apparatus of Example 8 and computation performed by the fluorescent-component-density computation unit $13d_2$, and is a diagram showing, in time-series, the gain and the detection timing of the fluorescence images at the fluorescence wavelengths of the individual fluorescent components under the reference exposure conditions.

FIG. 14B is an explanatory diagram showing the exposure conditions in the fluorescence-endoscope apparatus of Example 8 and computation performed by the fluorescent-component-density computation unit $13d_2$, and is a diagram showing, in time-series, the gain and the detection timing of the fluorescence images at the fluorescence wavelengths of the individual fluorescent components under the exposure conditions in Example 8.

FIG. 14C is an explanatory diagram showing the exposure conditions in the fluorescence-endoscope apparatus of Example 8 and computation performed by the fluorescent-component-density computation unit $13d_2$, and is a diagram showing a matrix equation that is used in the UNMIXING processing performed by the fluorescent-component-density computation unit $13d_2$ under the exposure conditions shown in FIG. 14B.

FIG. 17A is a diagram showing example exposure timings for spectral images of the individual fluorescent components 1 to 3 at the maximum-fluorescence wavelengths $\lambda 1$ to $\lambda 3$, and is a diagram showing transmission-switching timings of the maximum wavelengths $\lambda 1$ to $\lambda 3$ of the three types of fluorescent components 1 to 3 by a tunable light-dispersing element.

FIG. 17B is a diagram showing example exposure timings for spectral images of the individual fluorescent components 1 to 3 at the maximum-fluorescence wavelengths $\lambda 1$ to $\lambda 3$, and is a diagram showing image-acquisition timings of the fluorescence wavelengths $\lambda 1$ to $\lambda 3$ that are acquired by an image acquisition apparatus.

FIG. 17C is a diagram showing example exposure timings for spectral images of the individual fluorescent components 1 to 3 at the maximum-fluorescence wavelengths $\lambda 1$ to $\lambda 3$, and is a diagram showing an example of a matrix equation for calculating densities D1 to D3 of the fluorescent components 1 to 3 using the conventional UNMIXING technique in a spectral image in which fluorescence signals generated by the fluorescent components 1 to 3 coexist.

DETAILED DESCRIPTION OF THE INVENTION

Figure 1:
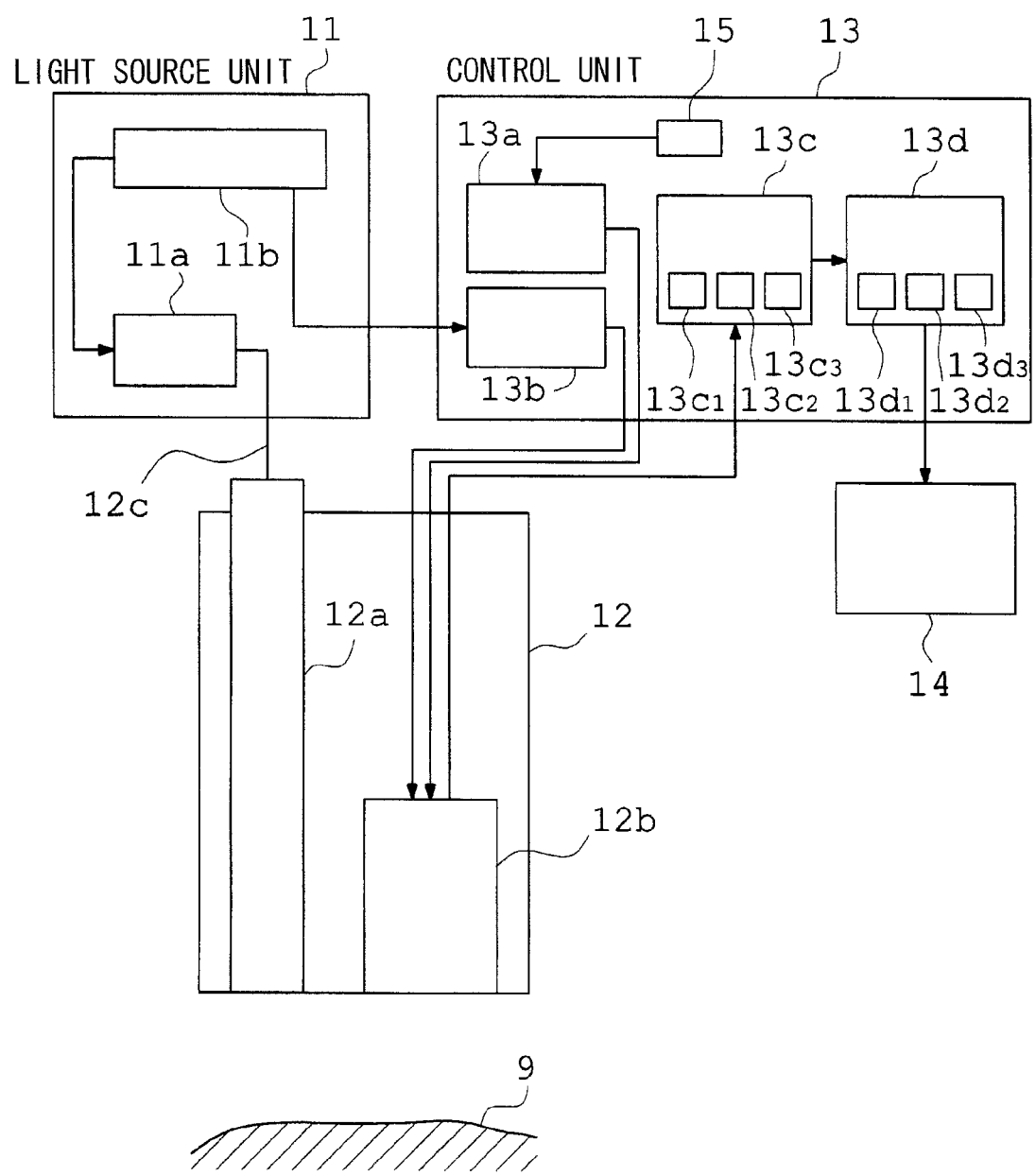
FIG. 1 is a block diagram showing, in outline, a configuration that is common to fluorescence-endoscope apparatuses of individual examples of the present invention.
Figure 2:
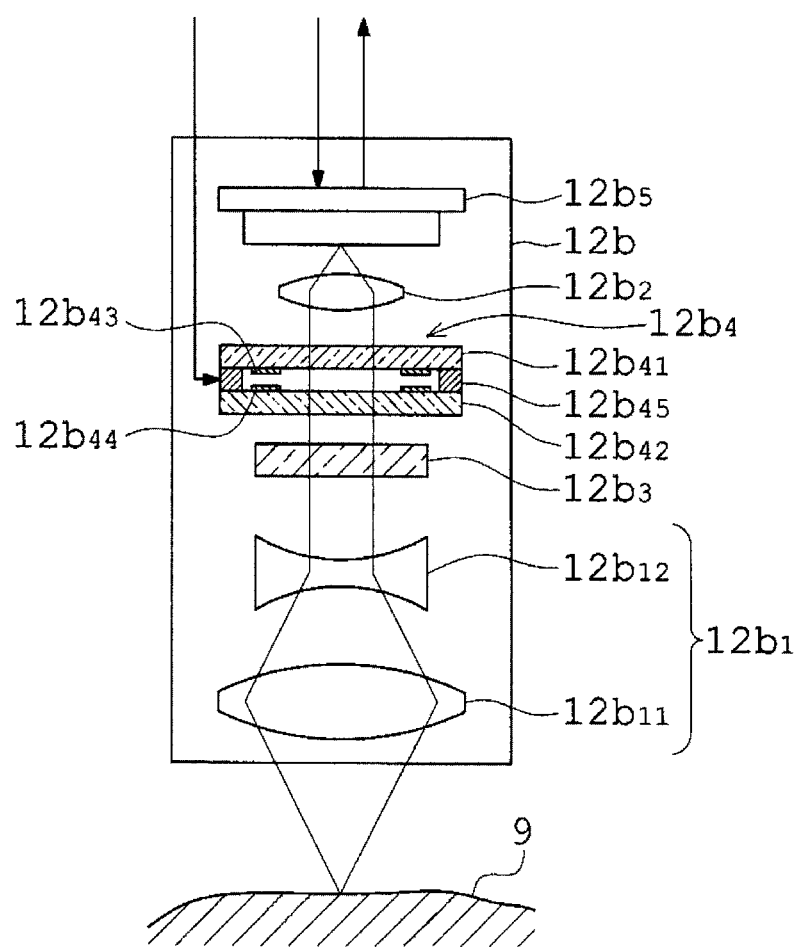
FIG. 2 is an explanatory diagram showing the configuration of an image acquisition portion of the fluorescence-endoscope apparatus shown in FIG. 1.

FIG. 1 is a block diagram showing, in outline, a configuration that is common to fluorescence-endoscope apparatuses of individual examples of the present invention. FIG. 2 is an explanatory diagram showing the configuration of an image acquisition portion in the fluorescence-endoscope apparatus shown in FIG. 1.

The fluorescence-endoscope apparatus in FIG. 1 includes a light source unit 11, an endoscope-tip inserted portion 12, a control unit 13, a display unit 14, and an exposure-conditions setting unit 15.

The light source unit 11 includes an excitation-light light source 11a and a light-source control circuit 11b.

The excitation-light light source 11a includes a light source (not shown) and a plurality of types of excitation filters (not shown) for respectively exciting a plurality of types of fluorescent components or a single excitation filter (not shown) for simultaneously exciting a plurality of types of fluorescent components, and the excitation-light light source 11a is configured to emit light having a predetermined excitation wavelength range.

The light-source control circuit 11b is configured so as to be able to perform, on the basis of values of the excitation time and excitation intensity that are set by the exposure-conditions setting unit 15, selective switching control of the intensities and the emission time of the excitation light that corresponds to a plurality of types of fluorescent components from the excitation-light light source 11a and that is emitted from the light source unit 11 by, for example, rotating a turret that is provided with the excitation filters and transparent glass plates on the circumference thereof or through, for example, a tunable light-dispersing element, such as an etalon etc.

The endoscope-tip inserted portion 12 includes an illumination optical system 12a and an image acquisition portion 12b.

The illumination optical system 12a radiates the light from the light source unit 11 through a light guide 12c onto biological tissue 9.

The excitation-light light source 11a, the light guide 12c, and the illumination optical system 12a in the light source unit 11 cooperatively function as a light source portion that radiates, onto an observed site on the biological subject 9, at least one type of excitation light that excites a plurality of types of fluorescent components having different fluorescence-wavelength characteristics.

As shown in FIG. 2, the image acquisition portion 12b includes an objective optical system $12b_1$, an image-forming optical system $12b_2$, an excitation-light cut filter $12b_3$, a tunable light-dispersing element $12b_4$, and an image acquisition device $12b_5$.

The excitation-light cut filter $12b_3$ has the optical property that it cuts light in a predetermined excitation wavelength range and transmits light in other wavelength ranges.

The tunable light-dispersing element $12b_4$ is formed of an etalon etc. The etalon is provided with a pair of optical substrates $12b_{41}$ and $12b_{42}$, electrostatic capacitance sensors $12b_{43}$ and $12b_{44}$ that measure the inter-surface distance between the surfaces of the pair of optical substrates $12b_{41}$ and $12b_{42}$ facing each other, and, as an actuator for moving one substrate $12b_{41}$, a piezoelectric device $12b_{45}$ which is driven under the control of a tunable-light-dispersing-element control unit circuit 13a, which will be described later. With such a configuration, under the control performed by the tunable-light-dispersing-element control circuit 13a, which will be described later, the tunable light-dispersing element $12b_4$ selects fluorescence in a plurality of predetermined wavelength ranges from the light incident thereon from an observed site on the biological subject 9 and allows it to pass through in a time-division manner.

The image acquisition device $12b_5$ is, for example, constructed of a monochrome CCD formed of a single-chip image sensor and photoelectrically converts the light that has been selected and transmitted by a light-dispersing optical element $12b_4$. The photoelectrically converted image is stored in frame memories $13c_1$ to $13c_3$ that are provided in the control unit 13, which will be described later.

The image acquisition portion 12b functions as a fluorescence image capturing unit that acquires images of fluorescence that are generated by the biological tissue for each of n types [where, m≤n] of wavelength λ1 to wavelength λn.

The control unit 13 includes the tunable-light-dispersing-element control circuit 13a, an image-acquisition-device control circuit 13b, a frame memory 13c, and an image processing circuit 13d.

The tunable-light-dispersing-element control circuit 13a controls driving of the tunable light-dispersing element $12b_4$ on the basis of values of the exposure time set by the exposure-conditions setting unit 15.

The frame memory 13c includes the frame memories $13c_1$, $13c_2$, and $13c_3$ for spectral images.

The frame memories $13c_1$, $13c_2$, and $13c_3$ for the spectral images individually store images of the light in the fluorescence-detecting wavelength range that has been selected by and transmitted through the tunable light-dispersing element $12b_4$ and photoelectrically converted via the image acquisition device $12b_5$.

The image-acquisition-device control circuit 13b controls driving of the image acquisition device $12b_5$ on the basis of values of the exposure time that are set by the exposure-conditions setting unit 15, the value of the signal gain of the detection wavelength acquired by the image acquisition device, and so forth.

The image processing circuit 13d includes an UNMIXING coefficient storage unit $13d_1$, a fluorescent-component-density computation unit $13d_2$, and a fluorescence-image combining portion $13d_3$.

The UNMIXING coefficient storage unit $13d_1$ stores fluorescence spectra of m types [where, 2≤m] of fluorescent component 1 to fluorescent component m present in the biological tissue 9 at their individual normalized densities under the reference exposure conditions and functions as a fluorescence-spectrum storage unit.

The fluorescent-component-density computation unit $13d_2$ obtains densities of the individual fluorescent components present in the biological tissue 9 for all pixels in the fluorescence images by performing computation using the fluorescence spectra of the individual fluorescent components 1 to fluorescent component m at the normalized densities under the reference exposure conditions that are stored in the UNMIXING coefficient storage unit $13d_1$ and the fluorescence images for every wavelength λ1 to wavelength λn that are acquired by the image acquisition portion 12b.

During the computation, the fluorescent-component-density computation unit $13d_2$ checks if the reference exposure conditions in the exposure condition items set by the exposure-conditions setting unit 15 have been changed; and if there has been a change in values of the predetermined exposure condition items during acquisition of the fluorescence image at least one wavelength λx among the wavelength λ1 to wavelength λn by the image acquisition portion 12b, in accordance with this change, upon calculating a density D1 of the fluorescent component 1 to a density Dm of the fluorescent component m using Equation (1), which will be described below, changes the coefficients a1 (λx) to am(λx) at the wavelength λx of the fluorescent component 1 to fluorescent component m at the normalized density under the reference exposure conditions using a ratio of the values of the predetermined exposure condition items that have been changed to the values of the predetermined exposure condition items under the reference exposure conditions when the fluorescence image at the wavelength λx is acquired by the image acquisition portion 12b.

The exposure condition items in the present invention refer to various items that can be set by an operator in the fluorescence-endoscope apparatus, such as, for example, the exposure time, the excitation intensity, the excitation time, the signal gain at the detection wavelength acquired by the image acquisition device, the detection intensity, adjusted by an ND filter, at the detection wavelength, and so forth.

The exposure-conditions setting unit 15 is configured such that the values of these exposure condition items can be set and entered. Among the exposure conditions that have been set and entered, the exposure-conditions setting unit 15 transmits the values of the excitation time and the excitation intensity to the light-source control circuit 11b in the light source unit 11. The exposure-conditions setting unit 15 transmits the values of the exposure time that have been set and entered to the tunable-light-dispersing-element control circuit 13a and the image-acquisition-device control circuit 13b in the control unit 13. The exposure-conditions setting unit 15 transmits the values of the set and entered signal gain at the detection wavelength acquired by the image acquisition device to the image-acquisition-device control circuit 13b in the control unit 13. The exposure-conditions setting unit 15 transmits the values of these exposure condition items that have been set and entered to the fluorescent-component-density computation unit 13$d_2$ of the image processing circuit 13d in the control unit 13.

The exposure-conditions setting unit 15 can be a device through which values can be input via a display similar to that of a personal computer etc. or can be a switch through which an operator can directly change the settings in the light source unit 11, the image-acquisition unit 12, and so forth.

The fluorescence-image combining portion 13$d_3$ creates the distribution images of the individual fluorescent components on the basis of the densities of the individual fluorescent components obtained by the fluorescent-component-density computation unit 13$d_2$; assigns predetermined colors, such as, for example, R, G, B, and so forth corresponding to the individual fluorescent components, to the created distribution images of the individual fluorescent components; and combines the distribution images to which the predetermined colors have been assigned into one image. At this time, the individual image signals are converted into output signals of different colors such that the portions in which the individual fluorescent components are distributed, such as, for example, a normal tissue portion, a lesion tissue portion, and so forth, can easily be identified.

The display unit 14 functions as an image display portion and displays the image that has been combined through the fluorescence-image combining portion 13$d_3$.

The image acquisition device 12$b_5$ can be formed of a color CCD that is provided with, for example, a mosaic filter (not shown) and a single-chip image sensor (not shown).

The single-chip image sensor can be configured such that the pixels each correspond to respective filters that form a mosaic filter and that transmit the light in the individual wavelength ranges, and such that the light of the image separated by the mosaic filter is acquired separately at different pixels.

In this case, the frame memories 13$c_1$, 13$c_2$, and 13$c_3$ for the spectral images can be configured such that the individual memories correspond to the individual filters that form the mosaic filter and that transmit the light in the individual wavelength ranges, and such that individual image signals that have been separated through the mosaic filter and acquired at the corresponding individual pixels are stored separately therein.

A procedure for separating the fluorescent components using an UNMIXING technique in the fluorescent-component-density computation unit 13$d_2$ will be explained below.

A method for computing the densities D of the individual fluorescent components in the UNMIXING will be described first.

As described above, a signal intensity $I_{all}(\lambda n)$ of the measurement target at the wavelength $\lambda n$ is defined as the sum of the signal intensities of the individual fluorescent components at the wavelength $\lambda n$ and can be expressed as in Equation (11) below:

$$I_{all}(\lambda n) = I1(\lambda n) + I2(\lambda n) \ldots + Im(\lambda n) \quad (11)$$

where I1 is the signal intensity obtained from the fluorescent component 1 at the wavelength $\lambda n$, I2 is the signal intensity obtained from the fluorescent component 2 at the wavelength $\lambda n$, and Im is the signal intensity obtained from the fluorescent component m at the wavelength $\lambda n$.

The signal intensity obtained from the fluorescent component is proportional to the density of the fluorescent component. Therefore, when m types of fluorescent components are present in the measurement target, the signal intensities obtained from the individual fluorescent components at the wavelength $\lambda n$ can be expressed as in Equations (12a) to (12c) below:

$$I1(\lambda n) = a1(\lambda n) * D1 \quad (12a)$$

where D1 is the density of the fluorescent component 1, and a1 ($\lambda n$) is the coefficient at the wavelength $\lambda n$ of the fluorescent component 1 at the normalized density under the reference exposure conditions;

$$I2(\lambda n) = a2(\lambda n) * D2 \quad (12b)$$

where D2 is the density of the fluorescent component 2, and a2 ($\lambda n$) is the coefficient at the wavelength $\lambda n$ of the fluorescent component 2 at the normalized density under the reference exposure conditions; and $$Im(\lambda n) = am(\lambda n) * Dm \quad (12c)$$

where Dm is the density of the fluorescent component m, and am($\lambda n$) is the coefficient at the wavelength $\lambda n$ of the fluorescent component m at the normalized density under the reference exposure conditions.

In accordance with these Equations (12a) to (12c), when m types of fluorescent components are assumed to be present in the measurement target, the signal intensities of the measurement target at n types of wavelength $\lambda 1$ to wavelength $\lambda n$ can be expressed by, for example, matrix equation (13) below:

[Expression 6]

$$\begin{pmatrix} I_{all}(\lambda 1) \\ I_{all}(\lambda 2) \\ \vdots \\ I_{all}(\lambda n) \end{pmatrix} = \begin{pmatrix} a1(\lambda 1) & a2(\lambda 1) & \ldots & am(\lambda 1) \\ a1(\lambda 2) & a2(\lambda 2) & \ldots & am(\lambda 2) \\ \vdots & \vdots & \vdots & \vdots \\ a1(\lambda n) & a2(\lambda n) & \ldots & am(\lambda n) \end{pmatrix} \begin{pmatrix} D1 \\ D2 \\ \vdots \\ Dn \end{pmatrix}. \quad (13)$$

Here, the left-hand side in the matrix equation (13):

[Expression 7]

$$\begin{pmatrix} I_{all}(\lambda 1) \\ I_{all}(\lambda 2) \\ \vdots \\ I_{all}(\lambda n) \end{pmatrix}$$

represents the spectra of the measurement target.

The right-hand side in the matrix equation (13):

[Expression 8]

$$\begin{pmatrix} a1(\lambda 1) & a2(\lambda 1) & \ldots & am(\lambda 1) \\ a1(\lambda 2) & a2(\lambda 2) & \ldots & am(\lambda 2) \\ \vdots & \vdots & \vdots & \vdots \\ a1(\lambda n) & a2(\lambda n) & \ldots & am(\lambda n) \end{pmatrix}$$

represents the fluorescence spectra of the individual fluorescent components at the normalized density under the reference exposure conditions.

Here, regarding the exposure conditions during acquisition of the individual fluorescence images at the fluorescence wavelength $\lambda 1$ to fluorescence wavelength $\lambda n$ by the image acquisition portion 12b, if there is no change in the values of all exposure condition items compared with the values of the exposure condition items under the reference exposure conditions, the fluorescent-component-density computation unit 13$d_2$ obtains the densities D1, D2, . . . , and Dm of the individual fluorescent components by solving matrix equation (1) below:

[Expression 9]

$$\begin{pmatrix} D1 \\ D2 \\ \vdots \\ Dn \end{pmatrix} = \begin{pmatrix} a1(\lambda 1) & a2(\lambda 1) & \ldots & am(\lambda 1) \\ a1(\lambda 2) & a2(\lambda 2) & \ldots & am(\lambda 2) \\ \vdots & \vdots & \vdots & \vdots \\ a1(\lambda n) & a2(\lambda n) & \ldots & am(\lambda n) \end{pmatrix}^{-1} \begin{pmatrix} I_{all}(\lambda 1) \\ I_{all}(\lambda 2) \\ \vdots \\ I_{all}(\lambda n) \end{pmatrix}. \quad (1)$$

In the above matrix equation, if the number of types of spectral images and the number of types of fluorescent components are the same (in other words, n=m), because the number of equations and the number of different values of the densities of the fluorescent components become the same, it is possible to solve the matrix equation uniquely. If the number of types of spectral images is greater than the number of types of fluorescent components (in other words, n>m), even though the number of equations becomes greater than the number of different values of the densities of the fluorescent components, it is possible to solve the matrix equation by using a least squares method in this case. In contrast, if the number of types of spectral images is less than the number of types of fluorescent components (in other words, n<m), because the number of equations is less than the number of different values of the densities of the fluorescent components, it is not possible to solve the matrix equation.

Therefore, in the UNMIXING procedure, it is assumed that the number of types of spectral images is greater than or equal to the number of types of fluorescent components (in other words, n≥m).

On the other hand, regarding the exposure conditions during acquisition of the individual fluorescence images at the fluorescence wavelengths λ1 to fluorescence wavelength λn by the image acquisition portion 12$b$, if there is a change in the values of any exposure condition items constituting the exposure conditions for the fluorescence images at least one wavelength λx compared with the values of the exposure condition items under the reference exposure conditions, upon calculating a density D1 of the fluorescent component 1 to a density Dm of the fluorescent component m using Equation (1), the fluorescent-component-density computation unit 13$d_2$ changes the coefficients a1 (λx) to am(λx) at the wavelength λx of the fluorescent component 1 to fluorescent component m at the normalized density under the reference exposure conditions using the ratio of the values of predetermined exposure condition items that have been changed to the values of the predetermined exposure condition items under the reference exposure conditions when the fluorescence image at the wavelength λx is acquired by the image acquisition portion 12$b$.

For example, if there is a change in the exposure time for the fluorescence image at the fluorescence wavelength λ2 compared with the exposure time under the reference exposure conditions, when α$_2$ is defined as the ratio of the changed exposure time, the UNMINXING coefficient in Equation (1) above is corrected as in Equation (1') below:

[Expression 10]

$$\begin{pmatrix} D1 \\ D2 \\ \vdots \\ Dn \end{pmatrix} = \begin{pmatrix} a1(\lambda 1) & a2(\lambda 1) & \ldots & am(\lambda 1) \\ a1(\lambda 2) \times \alpha_2 & a2(\lambda 2) \times \alpha_2 & \ldots & am(\lambda 2) \times \alpha_2 \\ \vdots & \vdots & \vdots & \vdots \\ a1(\lambda n) & a2(\lambda n) & \ldots & am(\lambda n) \end{pmatrix}^{-1} \begin{pmatrix} I_{all}(\lambda 1) \\ I_{all}(\lambda 2) \\ \vdots \\ I_{all}(\lambda n) \end{pmatrix}. \quad (1')$$

Next, by solving Equation (1') above that has corrected the UNMIXING coefficients, the densities D1, D2, . . . , and Dm of the individual fluorescent components are obtained.

Next, effects and advantages afforded by the thus-configured fluorescence-endoscope apparatus of the present invention will be described.

Figure 3A:
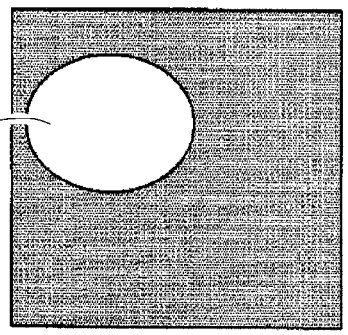
FIG. 3A is a diagram showing a distribution image of individual fluorescent components in the case where the UNMIXING technique described in Publication of Japanese Patent No. 2008-43396 is used for individual spectral images at fluorescence wavelengths λ1 to λ3 when, as shown in FIGS. 21A to 21C, the fluorescence wavelength λ2 emitted from the fluorescent component 2 among the three types of fluorescent components 1 to 3 is considerably dark, and is a diagram showing the distribution image of the fluorescent component 1.
Figure 3B:
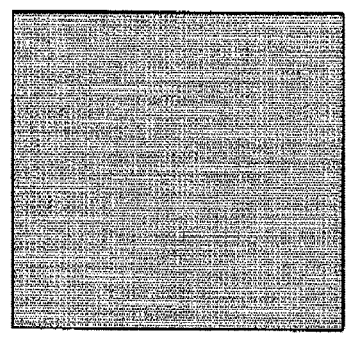
FIG. 3B is a diagram showing a distribution image of the individual fluorescent components in the case where the UNMIXING technique described in Publication of Japanese Patent No. 2008-43396 is used for the individual spectral images at the fluorescence wavelengths λ1 to λ3 when, as shown in FIGS. 21A to 21C, the fluorescence wavelength λ2 emitted from the fluorescent component 2 among the three types of fluorescent components 1 to 3 is considerably dark, and is a diagram showing the distribution image of the fluorescent component 2.
Figure 3C:
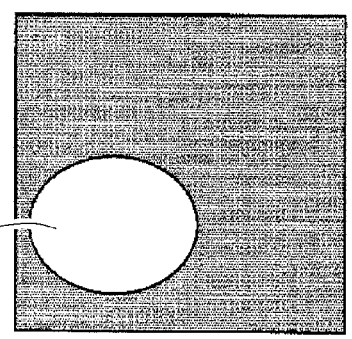
FIG. 3C is a diagram showing a distribution image of the individual fluorescent components in the case where the UNMIXING technique described in Publication of Japanese Patent No. 2008-43396 is used for the individual spectral images at the fluorescence wavelengths λ1 to λ3 when, as shown in FIGS. 21A to 21C, the fluorescence wavelength λ2 emitted from the fluorescent component 2 among the three types of fluorescent components 1 to 3 is considerably dark, and is a diagram showing the distribution image of the fluorescent component 3.
Figure 21A:
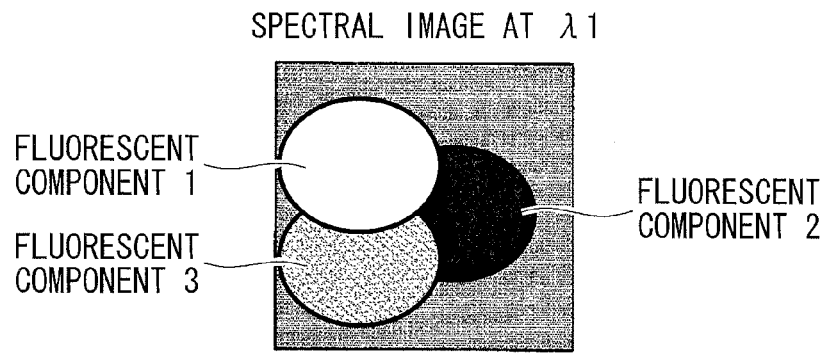
FIG. 21A is a diagram showing, as a comparative example for FIG. 20A, individual spectral images at the fluorescence wavelengths λ1 to λ3 when the fluorescence wavelength λ2 generated by the fluorescent component 2 among the three types of fluorescent components 1 to 3 is considerably dark, and is a diagram showing the spectral image at the fluorescence wavelength λ1.
Figure 21B:
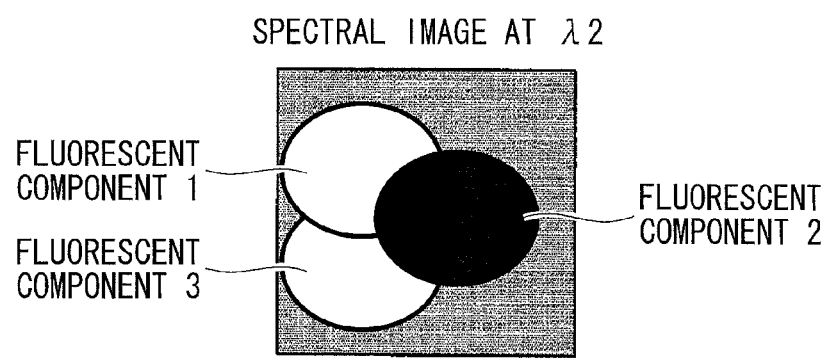
FIG. 21B is a diagram showing, as a comparative example for FIG. 20B, individual spectral images at the fluorescence wavelengths λ1 to λ3 when the fluorescence wavelength λ2 generated by the fluorescent component 2 among the three types of fluorescent components 1 to 3 is considerably dark, and is a diagram showing the spectral image at the fluorescence wavelength λ2.
Figure 21C:
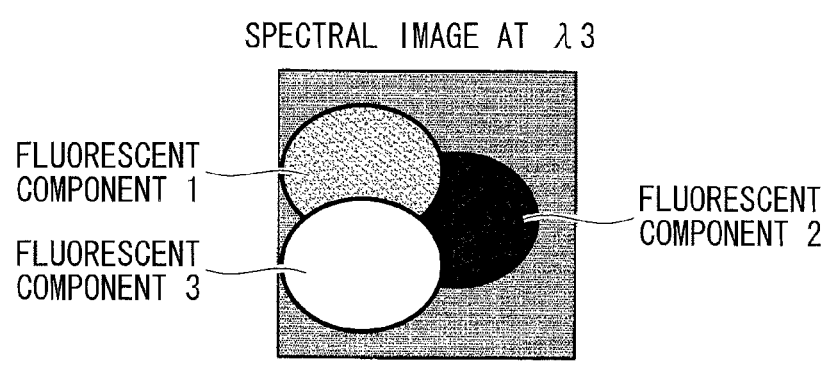
FIG. 21C is a diagram showing, as a comparative example for FIG. 20C, individual spectral images at the fluorescence wavelengths λ1 to λ3 when the fluorescence wavelength λ2 generated by the fluorescent component 2 among the three types of fluorescent components 1 to 3 is considerably dark, and is a diagram showing the spectral image at the fluorescence wavelength λ3.

Here, for example, it is assumed that, as shown in FIGS. 21A to 21C, the individual spectral images are acquired at the fluorescence wavelengths λ1 to λ3 when the maximum-fluorescence wavelength λ2 emitted from the fluorescent component 2 among the three types of fluorescent components 1 to 3 is considerably dark. In this case, if an adjustment for increasing the exposure time for the fluorescence image of the fluorescent component 2 is not made, even if the UNMIXING technique described in Publication of Japanese Patent No. 2008-43396 is applied to the spectral images shown in FIGS. 21A to 21C, as shown in FIG. 3B, the distribution image of the fluorescent component 2 becomes dark, making it impossible to observe.

Figure 22A:
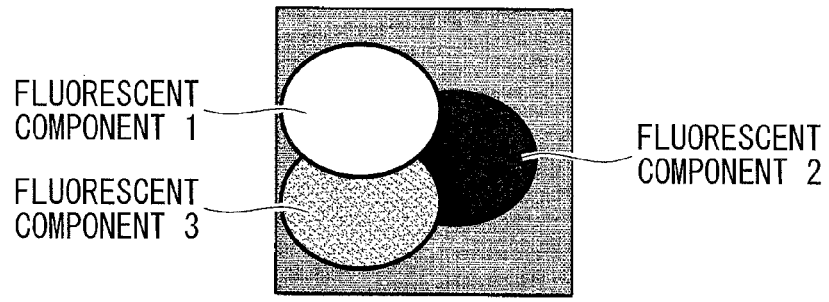
FIG. 22A is a diagram showing individual spectral images at the fluorescence wavelengths λ1 to λ3 in a situation where, for a sample containing the fluorescent components 1 to 3 that have brightnesses as shown in FIGS. 21A to 21C, the exposure time of the fluorescence image at the fluorescence wavelength λ2 is increased by a predetermined period of time from the exposure time under the reference exposure conditions, and is a diagram showing the spectral image at the fluorescence wavelength λ1.
Figure 22B:
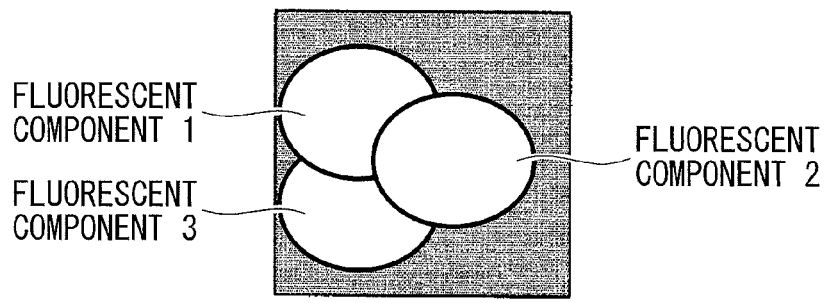
FIG. 22B is a diagram showing individual spectral images at the fluorescence wavelengths λ1 to λ3 in a situation where, for a sample containing the fluorescent components 1 to 3 that have brightnesses as shown in FIGS. 21A to 21C, the exposure time of the fluorescence image at the fluorescence wavelength λ2 is increased by a predetermined period of time from the exposure time under the reference exposure conditions, and is a diagram showing the spectral image at the fluorescence wavelength λ2.
Figure 22C:
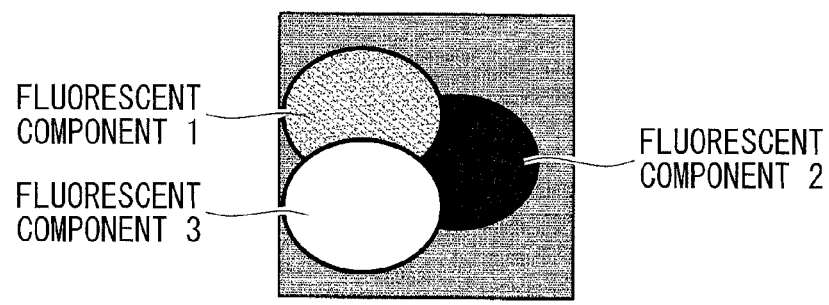
FIG. 22C is a diagram showing individual spectral images at the fluorescence wavelengths λ1 to λ3 in a situation where, for a sample containing the fluorescent components 1 to 3 that have brightnesses as shown in FIGS. 21A to 21C, the exposure time of the fluorescence image at the fluorescence wavelength λ2 is increased by a predetermined period of time from the exposure time under the reference exposure conditions, and is a diagram showing the spectral image at the fluorescence wavelength λ3.
Figure 23A:
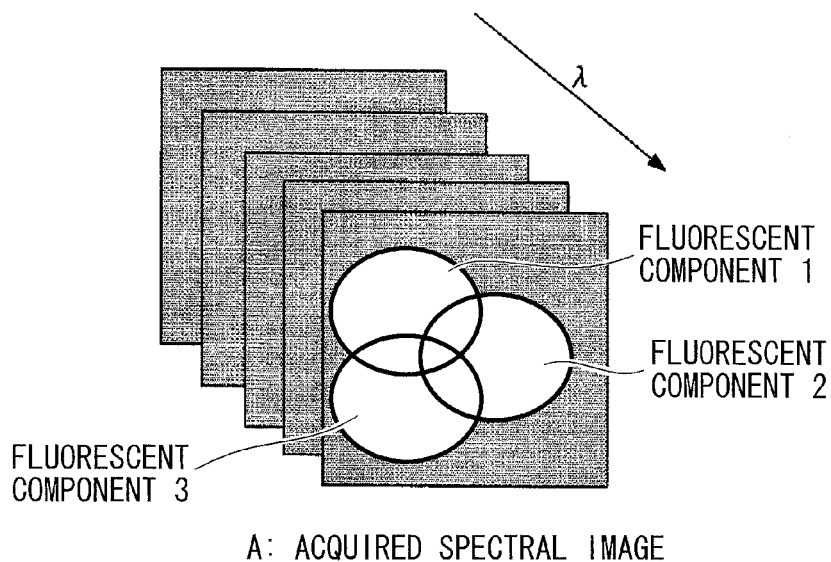
FIG. 23A is a diagram showing individual distribution images of the fluorescent components 1 to 3 after UNMIXING processing has been performed on the individual spectral images at the fluorescence wavelengths λ1 to λ3 in a situation where the exposure time for the fluorescence images at the fluorescence wavelength λ2 shown in FIGS. 22A to 22C is increased from the exposure time under the reference exposure conditions, and is a diagram showing a group of the acquired individual spectral images.
Figure 23B:
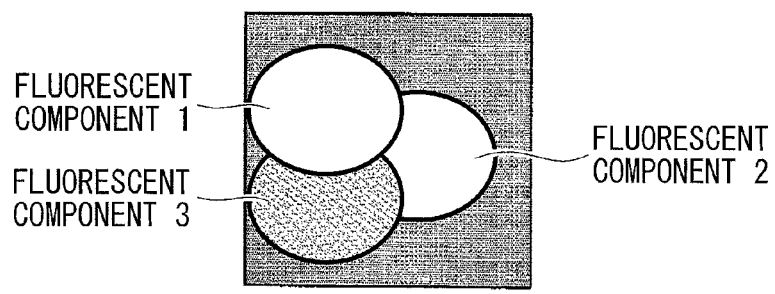
FIG. 23B is a diagram showing individual distribution images of the fluorescent components 1 to 3 after UNMIXING processing has been performed on the individual spectral images at the fluorescence wavelengths λ1 to λ3 in a situation where the exposure time for the fluorescence images at the fluorescence wavelength λ2 shown in FIGS. 22A to 22C is increased from the exposure time under the reference exposure conditions, and is a diagram showing the distribution image of the fluorescent component 1.
Figure 23C:
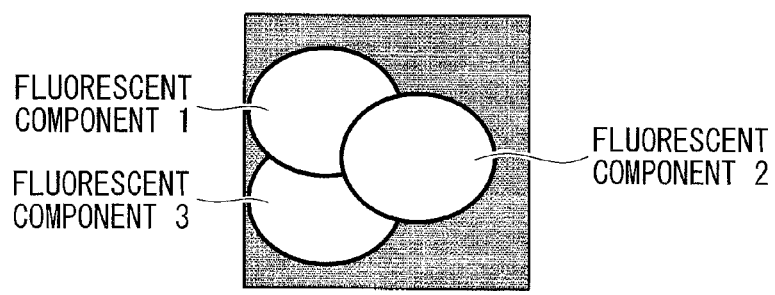
FIG. 23C is a diagram showing individual distribution images of the fluorescent components 1 to 3 after UNMIXING processing has been performed on the individual spectral images at the fluorescence wavelengths λ1 to λ3 in a situation where the exposure time for the fluorescence images at the fluorescence wavelength λ2 shown in FIGS. 22A to 22C is increased from the exposure time under the reference exposure conditions, and is a diagram showing the distribution image of the fluorescent component 2.
Figure 23D:
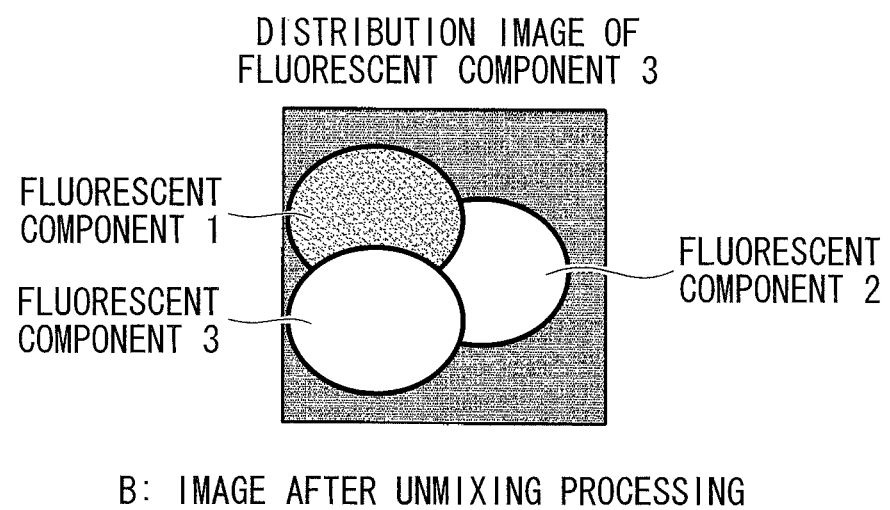
FIG. 23D is a diagram showing individual distribution images of the fluorescent components 1 to 3 after UNMIXING processing has been performed on the individual spectral images at the fluorescence wavelengths λ1 to λ3 in a situation where the exposure time for the fluorescence images at the fluorescence wavelength λ2 shown in FIGS. 22A to 22C is increased from the exposure time under the reference exposure conditions, and is a diagram showing the distribution image of the fluorescent component 3.

Next, if the exposure time of the fluorescence image at the fluorescence wavelength λ2 is made longer than the exposure time under the reference exposure conditions, the spectral images shown in FIGS. 22A to 22C are acquired. In this case, if the UNMIXING technique described in Publication of Japanese Patent No. 2008-43396 is applied, as shown in FIG. 4B,
it is possible to extract the bright fluorescence component of the fluorescent component 2 from the distribution image of the fluorescent component 2; however, it is not possible to separate the fluorescent components of the other fluorescent components 1 and 3.

Figure 5A:
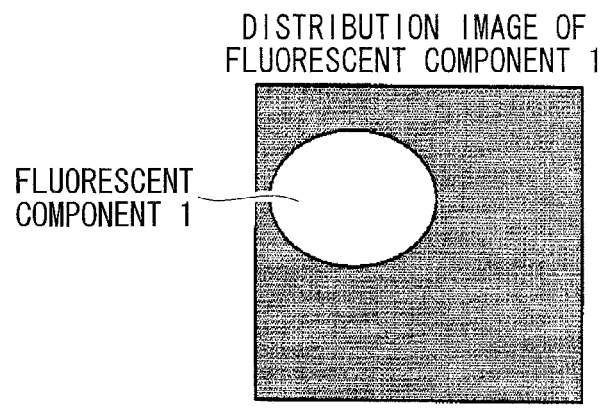
FIG. 5A is a diagram showing a distribution image of the individual fluorescent components in the case where the UNMIXING technique that is performed by a fluorescent-component-density computation unit $13d_2$ in the fluorescence-endoscope apparatus of the present invention is used for the individual spectral images at the fluorescence wavelengths λ1 to λ3 when the exposure time of the fluorescence images at the fluorescence wavelength λ2 is increased by a predetermined period of time from the exposure time under the reference exposure conditions in samples that are shown in FIGS. 22A to 22C having combinations of the fluorescent components shown in FIGS. 21A to 21C, and is a diagram showing the distribution image of the fluorescent component 1.
Figure 5B:
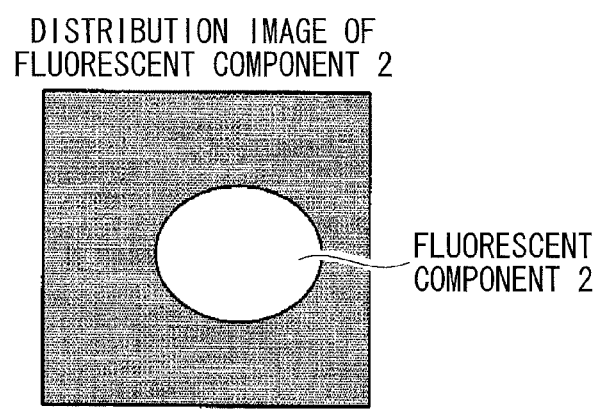
FIG. 5B is a diagram showing a distribution image of the individual fluorescent components in the case where the UNMIXING technique that is performed by the fluorescent-component-density computation unit $13d_2$ in the fluorescence-endoscope apparatus of the present invention is used for the individual spectral images at the fluorescence wavelengths λ1 to λ3 when the exposure time of the fluorescence images at the fluorescence wavelength λ2 is increased by a predetermined period of time from the exposure time under the reference exposure conditions in samples that are shown in FIGS. 22A to 22C having combinations of the fluorescent components shown in FIGS. 21A to 21C, and is a diagram showing the distribution image of the fluorescent component 2.
Figure 5C:
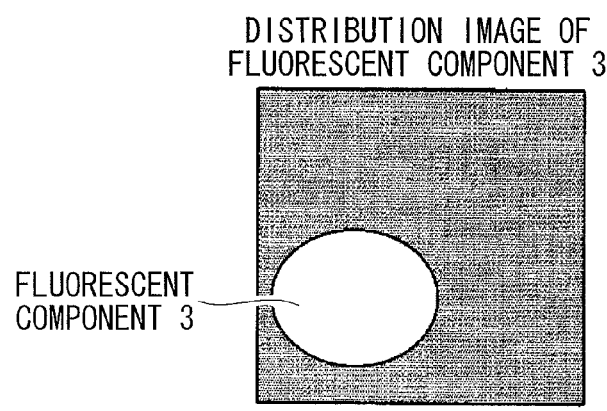
FIG. 5C is a diagram showing a distribution image of the individual fluorescent components in the case where the UNMIXING technique that is performed by the fluorescent-component-density computation unit $13d_2$ in the fluorescence-endoscope apparatus of the present invention is used for the individual spectral images at the fluorescence wavelengths λ1 to λ3 when the exposure time of the fluorescence images at the fluorescence wavelength λ2 is increased by a predetermined period of time from the exposure time under the reference exposure conditions in samples that are shown in FIGS. 22A to 22C having combinations of the fluorescent components shown in FIGS. 21A to 21C, and is a diagram showing the distribution image of the fluorescent component 3.

In contrast, according to the present invention, when the spectral images shown in FIGS. 22A to 22C are acquired by increasing the exposure time of the fluorescence image at the fluorescence wavelength λ2 from the exposure time under the reference exposure conditions, the fluorescent-component-density computation unit 13$d_2$ adjusts, in accordance with the change in the exposure time, the UNMIXING coefficients that are obtained upon application of the UNMIXING technique by using the ratio of the changed exposure time to the reference exposure time. Therefore, the densities of the fluorescent components calculated through the matrix equation (1) are obtained on the basis of the values obtained by suitably correcting the UNMIXING coefficients. As a result, as shown in FIGS. 5A to 5C, the acquired spectral images are bright images in which the fluorescence components among the individual fluorescent components 1 to 3 are separated.

This will be described using matrices in the UNMIXING technique.

<Intensities of Spectral Images Derived Using UNMIXING Coefficients>

For example, when $I_{all}(\lambda 1)$, $I_{all}(\lambda 2)$, and $I_{all}(\lambda 3)$ are defined as the intensities of the spectral images of the fluorescent components 1 to 3, they are represented by following equations using the UNMIXING coefficients:

(1) spectral image at the fluorescence wavelength λ1

$$I_{all}(\lambda 1) = D1 \times a1(\lambda 1) + D2 \times a2(\lambda 1) + D3 \times a3(\lambda 1);$$

(2) spectral image at the fluorescence wavelength $\lambda 2$ $$I_{all}(\lambda 2)=D1\times a1(\lambda 2)+D2\times a2(\lambda 2)+D3\times a3(\lambda 2);$$

(3) spectral image at the fluorescence wavelength $\lambda 3$ $$I_{all}(\lambda 3)=D1\times a1(\lambda 3)+D2\times a2(\lambda 3)+D3\times a3(\lambda 3).$$

<Distribution Images Derived from Above-Mentioned Spectral Images>

According to the above-mentioned equations, the distribution images of the fluorescent components 1 to 3 can be expressed by the following equations:

(1) distribution image of the fluorescent component 1

$$[I_{all}(\lambda 1)+I_{all}(\lambda 2)+I_{all}(\lambda 3)]-[D2\times a2(\lambda 1)+D3\times a3(\lambda 1)+D2\times a2(\lambda 2)+D3\times a3(\lambda 2)+D2\times a2(\lambda 3)+D3\times a3(\lambda 3)]=D1\times a1(\lambda 1)+D1\times a1(\lambda 2)+D1\times a1(\lambda 3);$$

(2) distribution image of the fluorescent component 2

$$[I_{all}(\lambda 1)+I_{all}(\lambda 2)+I_{all}(\lambda 3)]-[D1\times a1(\lambda 1)+D3\times a3(\lambda 1)+D1\times a1(\lambda 2)+D3\times a3(\lambda 2)+D1\times a1(\lambda 3)+D3\times a3(\lambda 3)]=D2\times a2(\lambda 1)+D2\times a2(\lambda 2)+D2\times a2(\lambda 3);$$

(3) distribution image of the fluorescent component 3

$$[I_{all}(\lambda 1)+I_{all}(\lambda 2)+I_{all}(\lambda 3)]-[D1\times a1(\lambda 1)+D2\times a2(\lambda 1)+D1\times a1(\lambda 2)+D2\times a2(\lambda 2)+D1\times a1(\lambda 3)+D2\times a2(\lambda 3)]=D3\times a3(\lambda 1)+D3\times a3(\lambda 2)+D3\times a3(\lambda 3).$$

A problem related to the calculation of the density of the fluorescent component 2 using the conventional UNMIXING technique performed when the exposure conditions for the fluorescence image at the maximum-fluorescence wavelength $\lambda 2$ of the fluorescent component 2 is changed from the exposure conditions under the reference exposure conditions will be described below.

For example, the exposure conditions for the fluorescence image at the fluorescence wavelength $\lambda 2$ are assumed to be doubled (for example, the exposure time is doubled) because the maximum-fluorescence wavelength $\lambda 2$ of the fluorescent component 2 is dark. If the UNMIXING coefficients are assumed to be unchanged at this time, the spectral images at the maximum-fluorescence wavelengths $\lambda 1$ to $\lambda 3$ of the fluorescent components 1 to 3 are individually expressed as in the following equations using the UNMIXING coefficients. At this time, the densities $D1'$, $D2'$, and $D3'$ of the individual fluorescent components have different values from the densities $D1$, $D2$, and $D3$ under the reference exposure conditions due to the change in the exposure conditions.

<Spectral Images Derived Using UNMIXING Coefficients>

(1) spectral image at the fluorescence wavelength $\lambda 1$ $$I_{all}(\lambda 1)=D1'\times a1(\lambda 1)+D2'\times a2(\lambda 1)+D3'\times a3(\lambda 1);$$

(2) spectral image at the fluorescence wavelength $\lambda 2$ $$2\times I_{all}(\lambda 2)=D1'\times a1(\lambda 2)+D2'\times a2(\lambda 2)+D3'\times a3(\lambda 2);$$

(3) spectral image at the fluorescence wavelength $\lambda 3$ $$I_{all}(\lambda 3)=D1'\times a1(\lambda 3)+D2'\times a2(\lambda 3)+D3'\times a3(\lambda 3).$$

However, in practice, the spectral image at the fluorescence wavelength $\lambda 2$ when the exposure conditions for the fluorescence wavelength $\lambda 2$ are doubled (for example, the exposure time is doubled) is expressed as:

$$2\times I_{all}(\lambda 2)=2\times[D1'\times a1(\lambda 2)+D2'\times a2(\lambda 2)+D3'\times a3(\lambda 2)].$$

Figure 4A:
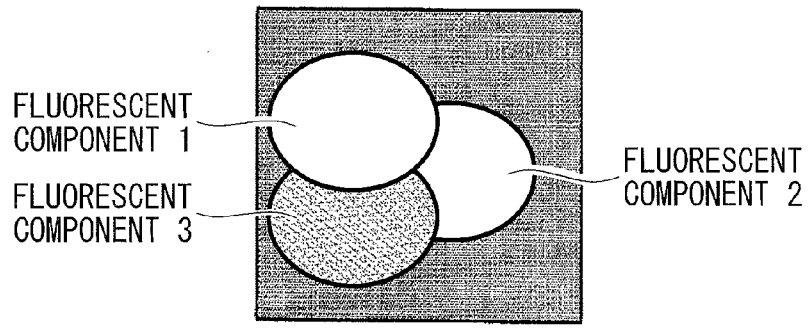
FIG. 4A is a diagram showing a distribution image of the individual fluorescent components in the case where the UNMIXING technique described in Publication of Japanese Patent No. 2008-43396 is used for the individual spectral images at the fluorescence wavelengths λ1 to λ3 when the exposure time of the fluorescence images at the fluorescence wavelength λ2 is increased by a predetermined period of time from the exposure time under the reference exposure conditions in samples that are shown in FIGS. 22A to 22C having combinations of the fluorescent components shown in FIGS. 21A to 21C, and is a diagram showing the distribution image of the fluorescent component 1.
Figure 4B:
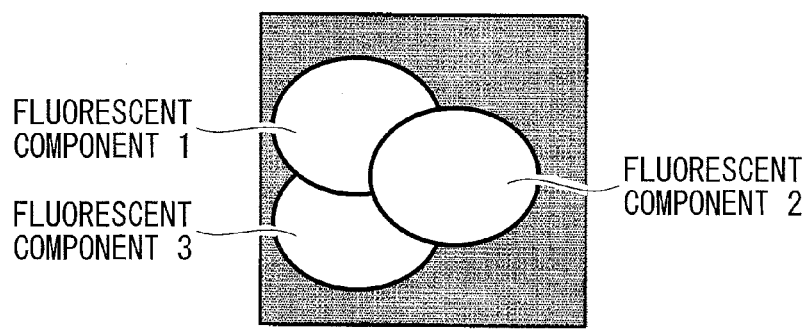
FIG. 4B is a diagram showing a distribution image of the individual fluorescent components in the case where the UNMIXING technique described in Publication of Japanese Patent No. 2008-43396 is used for the individual spectral images at the fluorescence wavelengths λ1 to λ3 when the exposure time of the fluorescence images at the fluorescence wavelength λ2 is increased by a predetermined period of time from the exposure time under the reference exposure conditions in samples that are shown in FIGS. 22A to 22C having combinations of the fluorescent components shown in FIGS. 21A to 21C, and is a diagram showing the distribution image of the fluorescent component 2.
Figure 4C:
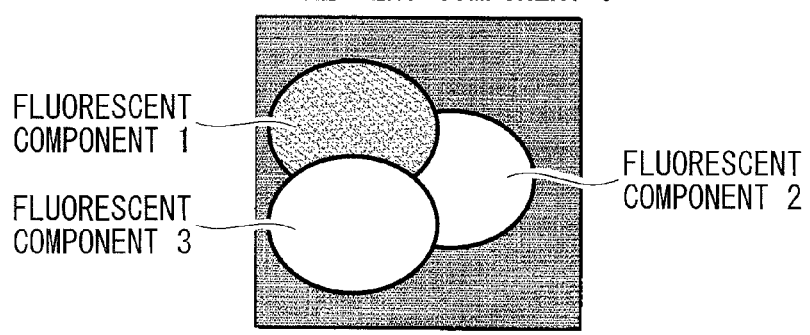
FIG. 4C is a diagram showing a distribution image of the individual fluorescent components in the case where the UNMIXING technique described in Publication of Japanese Patent No. 2008-43396 is used for the individual spectral images at the fluorescence wavelengths λ1 to λ3 when the exposure time of the fluorescence images at the fluorescence wavelength λ2 is increased by a predetermined period of time from the exposure time under the reference exposure conditions in samples that are shown in FIGS. 22A to 22C having combinations of the fluorescent components shown in FIGS. 21A to 21C, and is a diagram showing the distribution image of the fluorescent component 3.

Therefore:

(1) the distribution image of the fluorescent component 1 is expressed as:

$$[I_{all}(\lambda 1)+2\times I_{all}(\lambda 2)+I_{all}(\lambda 3)]-[D2'\times a2(\lambda 1)+D3'\times a3(\lambda 1)+D2'\times a2(\lambda 2)+D3'\times a3(\lambda 2)+D2'\times a2(\lambda 3)+D3'\times a3(\lambda 3)]=D1'\times a1(\lambda 1)+D1'\times a1(\lambda 2)+D1'\times a1(\lambda 3)+D1'\times a1(\lambda 2)+D2'\times a2(\lambda 2)+D3'\times a3(\lambda 2),$$

and so, as shown in FIG. 4A, it is not possible to separate the fluorescence component $D2'\times a2$ ($\lambda 2$) of the fluorescent component 2 and the fluorescence component $D3'\times a3$ ($\lambda 2$) of the fluorescent component 3;

(2) the distribution image of the fluorescent component 2 is expressed as:

$$[I_{all}(\lambda 1)+2\times I_{all}(\lambda 2)+I_{all}(\lambda 3)]-[D1'\times a1(\lambda 1)+D3'\times a3(\lambda 1)+D1'\times a1(\lambda 2)+D3'\times a3(\lambda 2)+D1'\times a1(\lambda 3)+D3'\times a3(\lambda 3)]=D2'\times a2(\lambda 1)+D2'\times a2(\lambda 2)+D2'\times a2(\lambda 3)+D2'\times a2(\lambda 2)+D1'\times a1(\lambda 2)+D3'\times a3(\lambda 2),$$

and so, as shown in FIG. 4B, it is not possible to separate the fluorescence component $D1'\times a1$ ($\lambda 2$) of the fluorescent component 1 and the fluorescence component $D3'\times a3$ ($\lambda 2$) of the fluorescent component 3; and (3) the distribution image of the fluorescent component 3 is expressed as:

$$[I_{all}(\lambda 1)+2\times I_{all}(\lambda 2)+I_{all}(\lambda 3)]-[D1'\times a1(\lambda 1)+D2'\times a2(\lambda 1)+D1'\times a1(\lambda 2)+D2'\times a2(\lambda 2)+D1'\times a1(\lambda 3)+D2'\times a2(\lambda 3)]=D3'\times a3(\lambda 1)+D3'\times a3(\lambda 2)+D3'\times a3(\lambda 3)+D3'\times a3(\lambda 2)+D1'\times a1(\lambda 2)+D2'\times a2(\lambda 2),$$

and so, as shown in FIG. 4C, it is not possible to separate the fluorescence component $D1'\times a1$ ($\lambda 2$) of the fluorescent component 1 and the fluorescence component $D2'\times a2(\lambda 2)$ of the fluorescent component 2.

For example, the exposure conditions for the fluorescence image at the fluorescence wavelength $\lambda 2$ are assumed to be halved (for example, the exposure time is halved) because the maximum-fluorescence wavelength $\lambda 2$ of the fluorescent component 2 is excessively bright. If the UNMIXING coefficients are assumed to be unchanged at this time, the spectral images at the maximum-fluorescence wavelengths $\lambda 1$ to $\lambda 3$ of the fluorescent components 1 to 3 are expressed as follows using the UNMIXING coefficients. At this time, the densities $D1''$, $D2''$, and $D3''$ of the individual fluorescent components have different values from the densities $D1$, $D2$, and $D3$ under the reference exposure conditions due to the change in the exposure conditions.

<Spectral Images Derived Using UNMIXING Coefficients>

(1) spectral image at the fluorescence wavelength $\lambda 1$:

$$I_{all}(\lambda 1)=D1''\times a1(\lambda 1)+D2''\times a2(\lambda 1)+D3''\times a3(\lambda 1)$$

(2) spectral image at the fluorescence wavelength $\lambda 2$:

$$\frac{1}{2}\times I_{all}(\lambda 2)=D1''\times a1(\lambda 2)+D2''\times a2(\lambda 2)+D3''\times a3(\lambda 2)$$

(3) spectral image at the fluorescence wavelength $\lambda 3$:

$$I_{all}(\lambda 3)=D1''\times a1(\lambda 3)+D2''\times a2(\lambda 3)+D3''\times a3(\lambda 3)$$

However, in practice, the spectral image at the fluorescence wavelength $\lambda 2$ when the exposure conditions for the fluorescence wavelength $\lambda 2$ are halved (for example, the exposure time is halved) is expressed as:

$$\frac{1}{2}\times I_{all}(\lambda 2)=\frac{1}{2}\times[D1''\times a1(\lambda 2)+D2''\times a2(\lambda 2)+D3''\times a3(\lambda 2)].$$

Therefore:

(1) The distribution image of the fluorescent component 1 is expressed as $$[I_{all}(\lambda 1)+\frac{1}{2}\times I_{all}(\lambda 2)+I_{all}(\lambda 3)]-[D2''\times a2(\lambda 1)+D3''\times a3(\lambda 1)+D2''\times a2(\lambda 2)+D3''\times a3(\lambda 2)+D2''\times a2(\lambda 3)+D3''\times a3(\lambda 3)]=D1''\times a1(\lambda 1)+D1''\times a1(\lambda 2)+D1''\times a1(\lambda 3)-\frac{1}{2}\times[D1''\times a1(\lambda 2)+D2''\times a2(\lambda 2)+D3''\times a3(\lambda 2)],$$

and so, the fluorescence component of the fluorescent component 1 becomes darker than necessary by $-\frac{1}{2}\times D1''\times a1$ ($\lambda 2$).

(2) The distribution image of the fluorescent component 2 is expressed as $$[I_{all}(\lambda 1)+\tfrac{1}{2}\times I_{all}(\lambda 2)+I_{all}(\lambda 3)]-[D1''\times a1(\lambda 1)+D3''\times a3(\lambda 1)+D1''\times a1(\lambda 2)+D3''\times a3(\lambda 2)+D1''\times a1(\lambda 3)+D3''\times a3(\lambda 3)]=D2''\times a2(\lambda 1)+D2''\times a2(\lambda 2)+D2''\times a2(\lambda 3)-\tfrac{1}{2}\times[D2''\times a2(\lambda 2)+D1''\times a1(\lambda 2)+D3''\times a3(\lambda 2)],$$

and so, the fluorescence component of the fluorescent component 2 becomes darker than necessary by $-\tfrac{1}{2}\times D2''\times a2(\lambda 2)$. As a result, as shown in FIG. 3B, it is not possible to acquire the distribution image of the fluorescent component 2.

(3) The distribution image of the fluorescent component 3 is expressed as $$[I_{all}(\lambda 1)+\tfrac{1}{2}\times I_{all}(\lambda 2)+I_{all}(\lambda 3)]-[D2''\times a2(\lambda 1)+D3''\times a3(\lambda 1)+D2''\times a2(\lambda 2)+D3''\times a3(\lambda 2)+D2''\times a2(\lambda 3)+D3''\times a3(\lambda 3)]=D3''\times a3(\lambda 1)+D3''\times a3(\lambda 2)+D3''\times a3(\lambda 3)-\tfrac{1}{2}\times[D3''\times a3(\lambda 2)+D1''\times a1(\lambda 2)+D2''\times a2(\lambda 2)],$$

and so, the fluorescence component of the fluorescent component 3 becomes darker than necessary by $-\tfrac{1}{2}\times D3''\times a3(\lambda 2)$.

In contrast, in the present invention, as described above, the fluorescent-component-density computation unit 13$d_2$ adjusts, in accordance with the change in the exposure time, the UNMIXING coefficients that are obtained upon application of the UNMIXING technique by using the ratio of the changed exposure time to the reference exposure time. Therefore, the densities of the fluorescent components that are to be calculated through the matrix equation (1) are obtained on the basis of the values obtained by suitably correcting the UNMIXING coefficients.

Specifically, for example, the exposure conditions for the fluorescence image at the fluorescence wavelength $\lambda 2$ are assumed to be doubled (for example, the exposure time is doubled) because the maximum-fluorescence wavelength $\lambda 2$ of the fluorescent component 2 is dark. If the UNMIXING coefficients are assumed to be changed at this time, the spectral images at the maximum-fluorescence wavelengths $\lambda 1$ to $\lambda 3$ of the fluorescent components 1 to 3 are expressed as follows using the UNMIXING coefficients.

<Spectral Images Derived Using UNMIXING Coefficients>
(1) spectral image at the fluorescence wavelength $\lambda 1$ $$I_{all}(\lambda 1)=D1\times a1(\lambda 1)+D2\times a2(\lambda 1)+D3\times a3(\lambda 1);$$

(2) spectral image at the fluorescence wavelength $\lambda 2$ $$2\times I_{all}(\lambda 2)=D1\times a1(\lambda 2)\times 2+D2\times a2(\lambda 2)\times 2+D3\times a3(\lambda 2)\times 2;$$

(3) spectral image at the fluorescence wavelength $\lambda 3$ $$I_{all}(\lambda 3)=D1\times a1(\lambda 3)+D2\times a2(\lambda 3)+D3\times a3(\lambda 3).$$

Therefore:
(1) The distribution image of the fluorescent component 1 is expressed as $$[I_{all}(\lambda 1)+2\times I_{all}(\lambda 2)+I_{all}(\lambda 3)]-[D2\times a2(\lambda 1)+D3\times a3(\lambda 1)+D2\times a2(\lambda 2)\times 2+D3\times a3(2)\times 2+D2\times a2(\lambda 3)+D3\times a3(\lambda 3)]=D1\times a1(\lambda 1)+D1\times a1(\lambda 2)\times 2+D1\times a1(\lambda 3),$$

and so, as shown in FIG. 5A, an image that is separated from the fluorescence components of the fluorescent components 2 and 3 is acquired.

(2) The distribution image of the fluorescent component 2 is expressed as $$[I_{all}(\lambda 1)+2\times I_{all}(\lambda 2)+I_{all}(\lambda 3)]-[D1\times a1(\lambda 1)+D3\times a3(\lambda 1)+D1\times a1(\lambda 2)\times 2+D3\times a3(\lambda 2)\times 2+D1\times a1(\lambda 3)+D3\times a3(\lambda 3)]=D2\times a2(\lambda 1)+D2\times a2(\lambda 2)\times 2+D2\times a2(\lambda 3),$$

and so, as shown in FIG. 5B, an image that is separated from the fluorescence components of the fluorescent components 1 and 3 is acquired.

(3) The distribution image of the fluorescent component 3 is expressed as $$[I_{all}(\lambda 1)+2\times I_{all}(\lambda 2)+I_{all}(\lambda 3)]-[D1\times a1(\lambda 1)+D2\times a2(\lambda 1)+D1\times a1(\lambda 2)\times 2+D2\times a2(\lambda 2)\times 2+D1\times a1(\lambda 3)+D2\times a2(\lambda 3)]=D3\times a3(\lambda 1)+D3\times a3(\lambda 2)\times 2+D3\times a3(\lambda 3),$$

and so, as shown in FIG. 5C, an image that is separated from the fluorescence components of the fluorescent components 2 and 3 is acquired.

Under the situation where the exposure conditions have been changed, the calculation of the densities of the fluorescent components according to the conventional UNMIXING technique and the calculation of the densities of the fluorescent components according to the present invention will be described below using further specific values.

For the sake of convenience of description, the case where two types of fluorescent components 1 and 2 are used will be described.

Figure 6A:
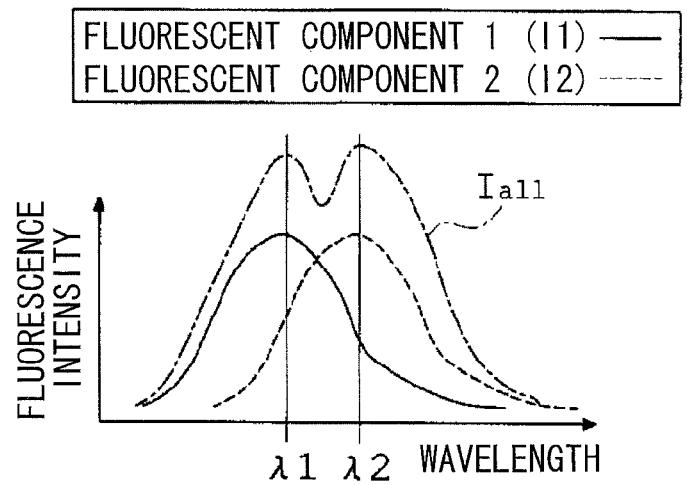
FIG. 6A is a diagram showing the fluorescence spectra of the individual fluorescent components 1 and 2 under the reference exposure conditions and the fluorescence spectrum of a measurement target in which the fluorescent components 1 and 2 are present in a mixed manner, and is a diagram showing the individual spectra when fluorescence intensities of the individual fluorescent components 1 and 2 are substantially the same.
Figure 6B:
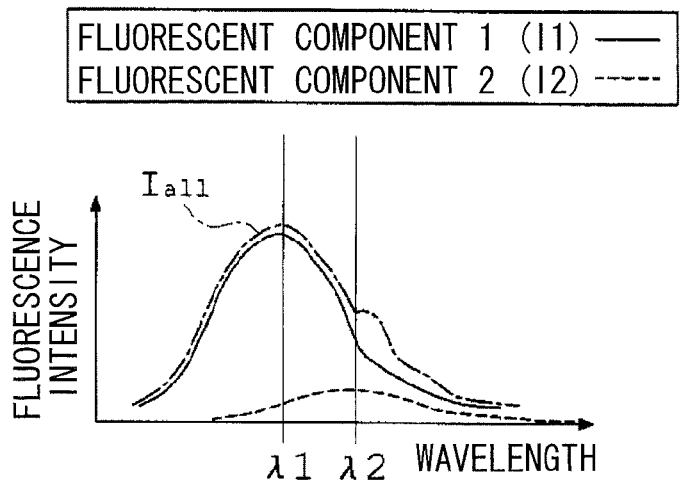
FIG. 6B is a diagram showing the fluorescence spectra of the individual fluorescent components 1 and 2 under the reference exposure conditions and the fluorescence spectrum of a measurement target in which the fluorescent components 1 and 2 are present in a mixed manner, and is a diagram showing the individual spectra when fluorescence intensities of the individual fluorescent components 1 and 2 are considerably different.
Figure 6C:
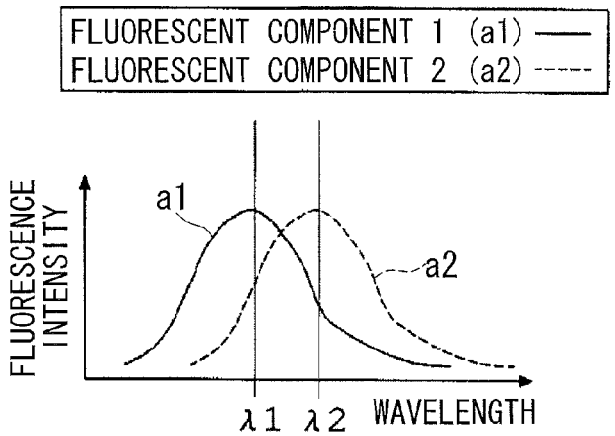
FIG. 6C is a diagram showing the fluorescence spectral properties of the individual fluorescent components 1 and 2 at the individual normalized densities.

FIGS. 6A and 6B are diagrams showing fluorescence spectra of the individual fluorescent components 1 and 2 under the reference exposure conditions and fluorescence spectra of a measurement target in which the fluorescent components 1 and 2 are present in a mixed manner, where FIG. 6A is a diagram showing individual spectra when the fluorescence intensities of the individual fluorescent components 1 and 2 are substantially the same, FIG. 63 is a diagram showing individual spectra when the fluorescence intensities of the individual fluorescent components 1 and 2 are considerably different, and FIG. 6C is a diagram showing the fluorescence spectral properties of the individual fluorescent components 1 and 2 at the individual normalized densities.

Calculation of the densities of the fluorescent components will be described, using individual fluorescent components 1 and 2, which are conventional fluorescence spectral properties at a individual normalized densities, as shown in FIG. 6C.

When $I_{all}(\lambda 1)$ and $I_{all}(\lambda 2)$ are defined as the intensities of the spectral images of the fluorescent components 1 and 2, the spectral images can be expressed as in Equation (21) below using the UNMIXING coefficients:

[Expression 11]

$$\begin{pmatrix} I_{all}(\lambda 1) \\ I_{all}(\lambda 2) \end{pmatrix} = \begin{pmatrix} a1(\lambda 1) & a2(\lambda 1) \\ a1(\lambda 2) & a2(\lambda 2) \end{pmatrix} \begin{pmatrix} D1 \\ D2 \end{pmatrix}. \qquad (21)$$

According to Equation (21), the densities D1 and D2 of the individual fluorescent components 1 and 2 can be expressed as in Equation (22) below:

[Expression 12]

$$\begin{pmatrix} D1 \\ D2 \end{pmatrix} = \begin{pmatrix} a1(\lambda 1) & a2(\lambda 1) \\ a1(\lambda 2) & a2(\lambda 2) \end{pmatrix}^{-1} \begin{pmatrix} I_{all}(\lambda 1) \\ I_{all}(\lambda 2) \end{pmatrix} \qquad (22)$$

$$= \frac{1}{a1(\lambda 1)\times a2(\lambda 2) - a1(\lambda 2)\times a2(\lambda 1)} \begin{pmatrix} a2(\lambda 2) & -a2(\lambda 1) \\ -a1(\lambda 2) & a1(\lambda 1) \end{pmatrix} \begin{pmatrix} I_{all}(\lambda 1) \\ I_{all}(\lambda 2) \end{pmatrix}.$$

According to Equation (22), the densities D1 and D2 of the fluorescent components 1 and 2 are obtained by solving Equations (23) and (24) below:

[Expression 13]

$$D1 = \frac{1}{a1(\lambda1) \times a2(\lambda2) - a1(\lambda2) \times a2(\lambda1)}|a2(\lambda2)I_{all}(\lambda1) - a2(\lambda1)I_{all}(\lambda2)| \quad (23)$$

$$D2 = \frac{1}{a1(\lambda1) \times a2(\lambda2) - a1(\lambda2) \times a2(\lambda1)}|-a1(\lambda2)I_{all}(\lambda1) + a1(\lambda1)I_{all}(\lambda2)|. \quad (24)$$

First, as shown in FIG. 6A, in the case where the density distribution of the fluorescent components 1 and 2 individually has the fluorescence intensities of substantially the same brightness and where the exposure conditions have been changed, the calculation of the densities of the fluorescent components according to the conventional UNMIXING technique and the calculation of the densities of the fluorescent components according to the present invention will be described.

In this case, as shown in FIG. 6(C), the fluorescence intensity at a fluorescence wavelength $\lambda1$ of the fluorescent component 1 is assumed to be 1, and the fluorescence intensity at a fluorescence wavelength $\lambda2$ of the fluorescent component 1 is assumed to be 0.5. The fluorescence intensity at a fluorescence wavelength $\lambda1$ of the fluorescent component 2 is assumed to be 0.5, and the fluorescence intensity at a fluorescence wavelength $\lambda2$ of the fluorescent component 2 is assumed to be 1.

As shown in FIG. 6A, the intensities of the spectral images at the wavelengths $\lambda1$ and $\lambda2$ are assumed to be unity, respectively.

By applying this to Equation (21) above, the spectral images at this time can be expressed as in Equation (21a) below:

[Expression 14]

$$\begin{pmatrix} 1 \\ 1 \end{pmatrix} = \begin{pmatrix} 1 & 0.5 \\ 0.5 & 1 \end{pmatrix}\begin{pmatrix} D1 \\ D2 \end{pmatrix}. \quad (21a)$$

By applying this to Equations (23) and (24) above, the densities D1 and D2 of the fluorescent components 1 and 2 are expressed as:

[Expression 15]

$$D1 = \frac{1}{1-0.25}(1-0.5) \approx 0.67$$

$$D2 = \frac{1}{1-0.25}(-0.5+1) \approx 0.67.$$

The distribution image of the fluorescent component 1 at this time is expressed as:

$$[I_{all}(\lambda1) + I_{all}(\lambda2)] - [D2 \times a2(\lambda1) + D2 \times a2(\lambda2)] =$$
$$D1 \times a1(\lambda1) + D1 \times a1(\lambda2) = 0.67 \times a1(\lambda1) + 0.67 \times a1(\lambda2),$$

and so, an image in which only the fluorescence component of the fluorescent component 1 is present and the fluorescence component of the fluorescent component 2 is not present is acquired.

The distribution image of the fluorescent component 2 is expressed as:

$$[I_{all}(\lambda1)+I_{all}(\lambda2)]-[D1 \times a1(\lambda1)+D1 \times a1(\lambda2)]=D2 \times a2$$
$$(\lambda1)+D2 \times a2(\lambda2)=0.67 \times a2(\lambda1)+0.67 \times a2(\lambda2),$$

and so, an image in which only the fluorescence component of the fluorescent component 2 is present and the fluorescence component of the fluorescent component 1 is not present is acquired.

Here, the calculated values for the densities of the fluorescent components 1 and 2 according to the conventional UNMIXING technique and the calculated values for the densities of the fluorescent components 1 and 2 according to the present invention will be shown for the case where the exposure time of the fluorescence wavelength $\lambda2$ is made 10-times greater to make the fluorescence intensity $I_{all}(\lambda2)$ 10-times greater.

With the method of calculating the densities of the fluorescent components 1 and 2 according to the conventional UNMIXING technique, by applying this to Equation (21) above, the spectral images can be expressed as in Equation (21b) below:

[Expression 16]

$$\begin{pmatrix} 1 \\ 10 \end{pmatrix} = \begin{pmatrix} 1 & 0.5 \\ 0.5 & 1 \end{pmatrix}\begin{pmatrix} D1' \\ D2' \end{pmatrix}. \quad (21b)$$

By applying this to Equations (23) and (24) above, the densities D1' and D2' of the fluorescent components 1 and 2 are expressed as:

[Expression 17]

$$D1' = \frac{1}{1-0.25}(1-5) \approx -5.33$$

$$D2' = \frac{1}{1-0.25}(-0.5+10) \approx 12.67,$$

and so, values different from the densities D1 and D2 that are obtained from Equation (21a) above are obtained.

The distribution image of the fluorescent component 1 at this time is expressed as:

$$[I_{all}(\lambda1)+10 \times I_{all}(\lambda2)]-[D2' \times a2(\lambda1)+D2' \times a2(\lambda2)]$$
$$=D1' \times a1(\lambda1)+D2' \times a2(\lambda1)+10[D1' \times a1(\lambda2)+D2' \times$$
$$a2(\lambda2)]-[D2' \times a2(\lambda1)+D2' \times a2(\lambda2)]=D1' \times a1$$
$$(\lambda1)+10D1' \times a1(\lambda2)+9D2' \times a2(\lambda2),$$

and so, it is not possible to separate the fluorescence component 9D2'×a2 ($\lambda2$) of the fluorescent component 2.

Here, the fluorescence component of the fluorescent component 1 in the distribution image of the fluorescent component 1 is expressed as:

$$D1' \times a1(\lambda1)+10D1' \times a1(\lambda2) \approx -5.33 \times a1(\lambda1)+10 \times (-5.33) \times a2(\lambda2).$$

The fluorescence component of the fluorescent component 2 in the distribution image of the fluorescent component 1 is expressed as:

$$9D2' \times a2(\lambda2) \approx 9 \times 12.67 \times a2(\lambda2).$$

The distribution image of the fluorescent component 2 is expressed as:

$$[I_{all}(\lambda 1)+10 \times I_{all}(\lambda 2)]-[D1'\times a1(\lambda 1)+D1'\times a1(\lambda 2)]$$
$$=D1'\times a1(\lambda 1)+D2'\times a2(\lambda 1)+10[D1'\times a1(\lambda 2)+D2'\times a2(\lambda 2)]-[D1'\times a1(\lambda 1)+D1'\times a1(\lambda 2)]=D2'\times a2(\lambda 1)+9D1'\times a2(\lambda 2)+10D2'\times a2(\lambda 2),$$

and so, it is not possible to separate the fluorescence component $9D1'\times a2(\lambda 2)$ of the fluorescent component 1.

Here, the fluorescence component of the fluorescent component 1 in the distribution image of the fluorescent component 1 is expressed as:

$$9D1'\times a2(\lambda 2)\approx 9\times(-5.33)\times a2(\lambda 2).$$

The fluorescence component of the fluorescent component 2 in the distribution image of the fluorescent component 1 is expressed as:

$$D2'\times a2(\lambda 1)+10D2'\times a2(\lambda 2)\approx 12.67\times a2(\lambda 1)+10\times 12.67\times a2(\lambda 2).$$

In contrast, in the present invention, as described above, the fluorescent-component-density computation unit $13d_2$ adjusts, in accordance with the change in the exposure time, the UNMIXING coefficients that are obtained upon application of the UNMIXING technique by using the ratio of the changed exposure time to the reference exposure time. Therefore, the densities of the fluorescent components that are to be calculated through the matrix equation (1) are obtained on the basis of the values obtained by suitably correcting the UNMIXING coefficients.

In other words, in the method of calculating the densities of the fluorescent components 1 and 2 according to the UNMIXING technique of the present invention, by applying this to Equation (21) above, the spectral image can be expressed as in Equation (21c) below:

[Expression 18]

$$\begin{pmatrix} 1 \\ 10 \end{pmatrix} = \begin{pmatrix} 1 & 0.5 \\ 0.5\times 10 & 1\times 10 \end{pmatrix}\begin{pmatrix} D1 \\ D2 \end{pmatrix}. \quad (21c)$$

By applying this to Equations (23) and (24) above, the densities D1 and D2 of the fluorescent components 1 and 2 are expressed as:

[Expression 19]

$$D1 = \frac{1}{10-2.5}(10-5) \approx 0.67$$

$$D2 = \frac{1}{10-2.5}(-5+10) \approx 0.67,$$

and the values become the same as those of the densities D1 and D2 obtained from Equation (21a) above.

The distribution image of the fluorescent component 1 at this time is expressed as:

$$[I_{all}(\lambda 1)+10\times I_{all}(\lambda 2)]-[D2\times a2(\lambda 1)+10\times D2\times a2(\lambda 2)]$$
$$=D1\times a1(\lambda 1)+D2\times a2(\lambda 1)+10[D1\times a1(\lambda 2)+D2\times a2(\lambda 2)]-[D2\times a2(\lambda 1)+10\times D2\times a2(\lambda 2)]=D1\times a1(\lambda 1)+10\times D1\times a1(\lambda 2),$$

and so, an image that is separated from the fluorescence component of the fluorescent component 2 is acquired.

Here, the distribution image of the fluorescent component 1 contains only the fluorescence component of the fluorescent component 1 and is expressed as:

$$D1\times a1(\lambda 1)+10\times D1\times a1(\lambda 2)\approx 0.67\times a1(\lambda 1)+10\times 0.67\times a1(\lambda 2).$$

The distribution image of the fluorescent component 2 is expressed as:

$$[I_{all}(\lambda 1)+10\times I_{all}(\lambda 2)]-[D1\times a1(\lambda 1)+10\times D1\times a1(\lambda 2)]$$
$$=D1\times a1(\lambda 1)+D2\times a2(\lambda 1)+10[D1\times a1(\lambda 2)+D2\times a2(\lambda 2)]-[D1\times a1(\lambda 1)+10\times D1\times a1(\lambda 2)]=D2\times a2(\lambda 1)+10\times D2\times a2(\lambda 2),$$

and so, an image that is separated from the fluorescence component of the fluorescent component 1 is acquired.

At this time, the distribution image of the fluorescent component 2 contains only the fluorescence component of the fluorescent component 2 and is expressed as:

$$D2\times a2(\lambda 1)+10\times D2\times a2(\lambda 2)\approx 12.67\times a2(\lambda 1)+10\times 12.67\times a2(\lambda 2).$$

Next, as shown in FIG. 6B, the case where the fluorescence intensities of the individual fluorescent components 1 and 2 have a density distribution to be considerably different brightness will be described.

In this case, as shown in FIG. 6(C), the fluorescence intensity at a fluorescence wavelength $\lambda 1$ of the fluorescent component 1 is assumed to be 1, and the fluorescence intensity at a fluorescence wavelength $\lambda 2$ of the fluorescent component 1 is assumed to be 0.5. The fluorescence intensity at a fluorescence wavelength $\lambda 1$ of the fluorescent component 2 is assumed to be 0.5, and the fluorescence intensity at a fluorescence wavelength $\lambda 2$ of the fluorescent component 2 is assumed to be 1.

As shown in FIG. 6B, the intensities of the spectral images at the wavelengths $\lambda 1$ are assumed to be 1, and the intensities of the spectral images at the wavelengths $\lambda 2$ are assumed to be 0.55.

By applying this to Equation (21) above, the spectral images at this time can be expressed as in Equation (21a') below:

[Expression 20]

$$\begin{pmatrix} 1 \\ 0.55 \end{pmatrix} = \begin{pmatrix} 1 & 0.5 \\ 0.5 & 1 \end{pmatrix}\begin{pmatrix} D1 \\ D2 \end{pmatrix}. \quad (21a')$$

By applying this to Equations (23) and (24) above, the densities D1 and D2 of the fluorescent components 1 and 2 are expressed as:

[Expression 21]

$$D1 = \frac{1}{1-0.25}(1-0.5\times 0.55) \approx 0.97$$

$$D2 = \frac{1}{1-0.25}(-0.5+0.55) \approx 0.07.$$

The distribution image of the fluorescent component 1 at this time is expressed as:

$$[I_{all}(\lambda 1)+I_{all}(\lambda 2)]-[D2\times a2(\lambda 1)+D2\times a2(\lambda 2)]=D1\times a1(\lambda 1)+D1\times a1(\lambda 2),$$

and so, an image in which the fluorescence component of the fluorescent component 2 is not present is acquired.

Here, the distribution image of the fluorescent component 1 contains only the fluorescence component of the fluorescent component 1 and is expressed as:

$$D1\times a1(\lambda 1)+D1\times a1(\lambda 2)\approx 0.97\times a1(\lambda 1)+0.97\times a2(\lambda 2).$$

The distribution image of the fluorescent component 2 is expressed as:

$$[I_{all}(\lambda 1)+I_{all}(\lambda 2)]-[D1\times a1(\lambda 1)+D1\times a1(\lambda 2)]=D2\times a2(\lambda 1)+D2\times a2(\lambda 2),$$

and so, an image in which the fluorescence component of the fluorescent component 1 is not present is acquired.

Here, the distribution image of the fluorescent component 2 contains only the fluorescence component of the fluorescent component 2 and is expressed as:

$$D2\times a2(\lambda 1)+D2\times a2(\lambda 2)\approx 0.07\times a2(\lambda 1)+0.07\times a2(\lambda 2).$$

Here, the calculated values for the densities of the fluorescent components 1 and 2 according to the conventional UNMIXING technique and the calculated values for the densities of the fluorescent components 1 and 2 according to the present invention are shown for the case where the exposure time of the fluorescence wavelength λ2 is made 10-times greater to make the fluorescence intensity $I_{all}(\lambda 2)$ 10-times greater.

With the method of calculating the densities of the fluorescent components 1 and 2 according to the conventional UNMIXING technique, by applying this to Equation (21) above, the spectral images can be expressed as in Equation (21b') below:

[Expression 22]

$$\begin{pmatrix} 1 \\ 5.5 \end{pmatrix} = \begin{pmatrix} 1 & 0.5 \\ 0.5 & 1 \end{pmatrix} \begin{pmatrix} D1' \\ D2' \end{pmatrix}. \qquad (21b')$$

By applying this to Equations (23) and (24) above, the densities D1' and D2' of the fluorescent components 1 and 2 are expressed as:

$$D1' = \frac{1}{1-0.25}(1-2.75) \approx -2.33 \qquad \text{[Expression 23]}$$

$$D2' = \frac{1}{1-0.25}(-0.5+5.5) \approx 6.67,$$

and so, values different from those of the densities D1 and D2 obtained from Equation (21a') above are obtained.

The distribution image of the fluorescent component 1 at this time is expressed as:

$$[I_{all}(\lambda 1)+10\times I_{all}(\lambda 2)]-[D2'\times a2(\lambda 1)+D2'\times a2(\lambda 2)]$$
$$=D1'\times a1(\lambda 1)+D2'\times a2(\lambda 1)+10[D1'\times a1(\lambda 2)+D2'\times a2(\lambda 2)]-[D2'\times a2(\lambda 1)+D2'\times a2(\lambda 2)]=D1'\times a1(\lambda 1)+10D1'\times a1(\lambda 2)+9D2'\times a2(\lambda 2),$$

and so, it is not possible to separate the fluorescence component 9D2'×a2 (λ2) of the fluorescent component 2.

Here, the fluorescence component of the fluorescent component 1 in the distribution image of the fluorescent component 1 is expressed as:

$$D1'\times a1(\lambda 1)+10D1'\times a1(\lambda 2)\approx -2.33\times a1(\lambda 1)+10\times (-2.33)\times a1(\lambda 2).$$

The fluorescence component of the fluorescent component 2 in the distribution image of the fluorescent component 1 is expressed as:

$$9D2'\times a2(\lambda 2)\approx 9\times 6.67\times a2(\lambda 2).$$

The distribution image of the fluorescent component 2 is expressed as:

$$[I_{all}(\lambda 1)+10\times I_{all}(\lambda 2)]-[D1'\times a1(\lambda 1)+D1'\times a1(\lambda 2)]$$
$$=D1'\times a1(\lambda 1)+D2'\times a2(\lambda 1)+10[D1'\times a1(\lambda 2)+D2'\times a2(\lambda 2)]-[D1'\times a1(\lambda 1)+D1'\times a1(\lambda 2)]=D2'\times a2(\lambda 1)+9D1'\times a1(\lambda 2)+10D2'\times a2(\lambda 2),$$

and so, it is not possible to separate the fluorescence component 9D1'×a1 (λ2) of the fluorescent component 1.

Here, the fluorescence component of the fluorescent component 1 in the distribution image of the fluorescent component 2 is expressed as:

$$9D1'\times a1(\lambda 2)\approx 9\times (-2.33)\times a1(\lambda 2).$$

The fluorescence component of the fluorescent component 2 in the distribution image of the fluorescent component 2 is expressed as:

$$D2'\times a2(\lambda 1)+10D2'\times a2(\lambda 2)\approx 6.67\times a2(\lambda 1)+10\times 6.67\times a1(\lambda 2).$$

In contrast, in the method of calculating the densities of the fluorescent components 1 and 2 according to the UNMIXING technique of the present invention, by applying this to Equation (21) above, the spectral image can be expressed as in Equation (21c') below:

[Expression 24]

$$\begin{pmatrix} 1 \\ 5.5 \end{pmatrix} = \begin{pmatrix} 1 & 0.5 \\ 0.5\times 10 & 1\times 10 \end{pmatrix} \begin{pmatrix} D1 \\ D2 \end{pmatrix}. \qquad (21c')$$

By applying this to Equations (23) and (24) above, the densities D1 and D2 of the fluorescent components 1 and 2 are expressed as:

$$D1 = \frac{1}{10-2.5}(10-2.75) \approx 0.97 \qquad \text{[Expression 25]}$$

$$D2 = \frac{1}{10-2.5}(-5+5.5) \approx 0.07,$$

and the values become the same as those of the densities D1 and D2 obtained from Equation (21a') above.

The distribution image of the fluorescent component 1 at this time is expressed as:

$$[I_{all}(\lambda 1)+10\times I_{all}(\lambda 2)]-[D2\times a2(\lambda 1)+10\times D2\times a2(\lambda 2)]$$
$$=D1\times a1(\lambda 1)+D2\times a2(\lambda 1)+10[D1\times a1(\lambda 2)+D2\times a2(\lambda 2)]-[D2\times a2(\lambda 1)+10\times D2\times a2(\lambda 2)]=D1\times a1(\lambda 1)+10\times D1\times a1(\lambda 2),$$

and so, an image that is separated from the fluorescence component of the fluorescent component 2 is acquired.

Here, the distribution image of the fluorescent component 1 contains only the fluorescence component of the fluorescent component 1 and is expressed as:

$$D1\times a1(\lambda 1)+10\times D1\times a1(\lambda 2)\approx 0.97\times a1(\lambda 1)+10\times 0.97\times a1(\lambda 2).$$

The distribution image of the fluorescent component 2 is expressed as:

$$[I_{all}(\lambda 1)+10\times I_{all}(\lambda 2)]-[D1\times a1(\lambda 1)+10\times D1\times a1(\lambda 2)]$$
$$=D1\times a1(\lambda 1)+D2\times a2(\lambda 1)+10[D1\times a1(\lambda 2)+D2\times a2(\lambda 2)]-[D1\times a1(\lambda 1)+10\times D1\times a1(\lambda 2)]=D2\times a2(\lambda 1)+10\times D2\times a2(\lambda 2),$$

and so, an image that is separated from the fluorescence component of the fluorescent component 1 is acquired.

The distribution image of the fluorescent component 2 at this time is expressed as:

$$D2 \times a2(\lambda 1) + 10 \times D2 \times a2(\lambda 2) \approx 0.07 \times a2(\lambda 1) + 10 \times 0.07 \times a2(\lambda 2).$$

Therefore, according to the fluorescence-endoscope apparatus of the present invention, it is possible to provide a fluorescence-endoscope apparatus that is capable of, even if the exposure conditions are changed, displaying the individual fluorescent components in a separated manner regardless of the change in the exposure conditions while keeping the frame rate unchanged as much as possible, such that the brightnesses of the individual fluorescent components become brightnesses suitable for observing the fluorescence image.

Example 1

Figure 7A:
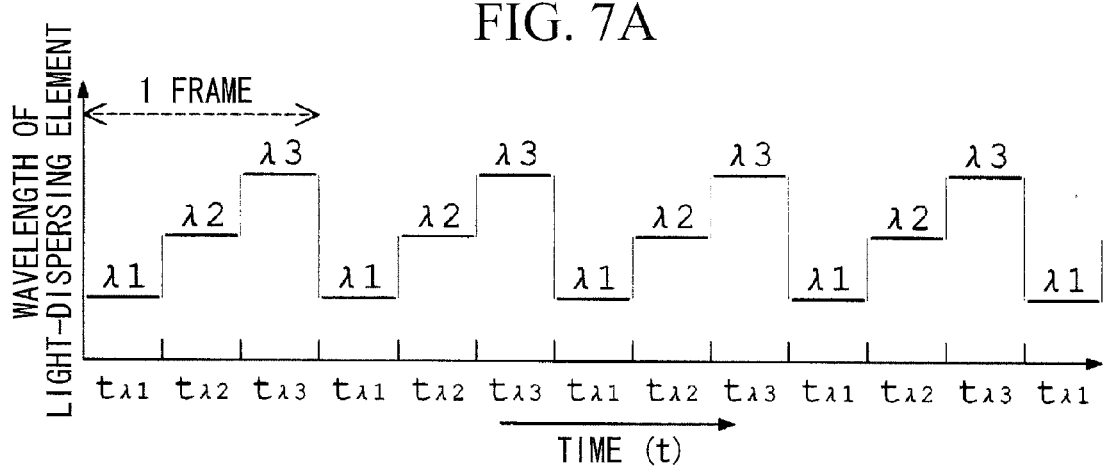
FIG. 7A is an explanatory diagram showing the exposure conditions in the fluorescence-endoscope apparatus of Example 1 and computation performed by the fluorescent-component-density computation unit $13d_2$, and is a diagram showing, in time-series, the light in each of the wavelength ranges selected by and transmitted through a tunable light-dispersing element $12b_4$ under the reference exposure conditions.
Figure 7B:
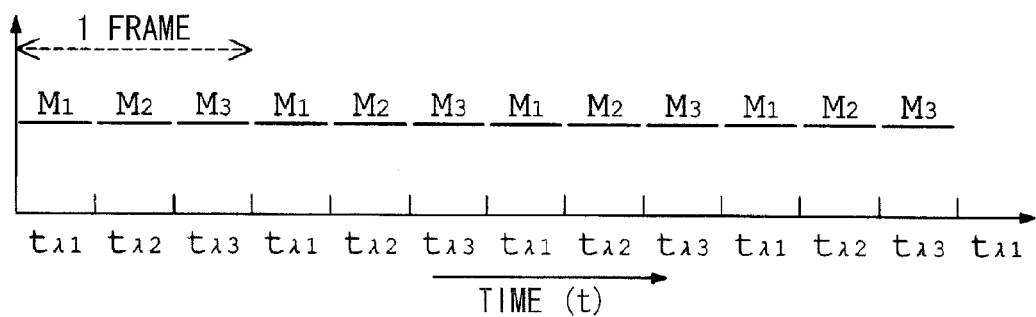
FIG. 7B is an explanatory diagram showing the exposure conditions in the fluorescence-endoscope apparatus of Example 1 and computation performed by the fluorescent-component-density computation unit $13d_2$, and is a diagram showing, in time-series, the light in each of the wavelength ranges that has been, at substantially the same time as in FIG. 7A, photoelectrically converted through an image acquisition device $12b_5$ and stored in each of frame memories $13c_1$, $13c_2$, and $13c_3$.
Figure 15A:
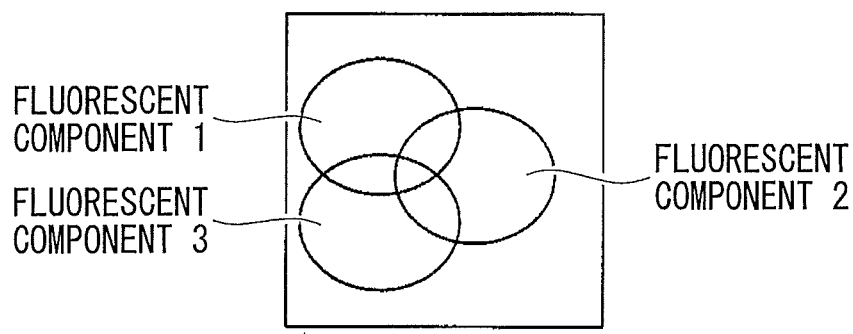
FIG. 15A is a diagram for explaining the three types of fluorescent components 1 to 3 present in a sample, and is a diagram conceptually showing the distribution of the fluorescent components 1 to 3 in the sample.
Figure 15B:
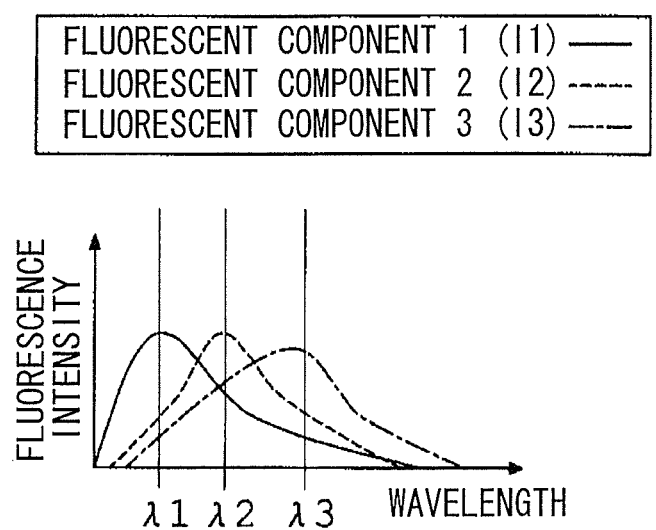
FIG. 15B is a diagram for explaining the three types of fluorescent components 1 to 3 present in a sample, and is a diagram showing fluorescence spectra of the fluorescent components 1 to 3.
Figure 16A:
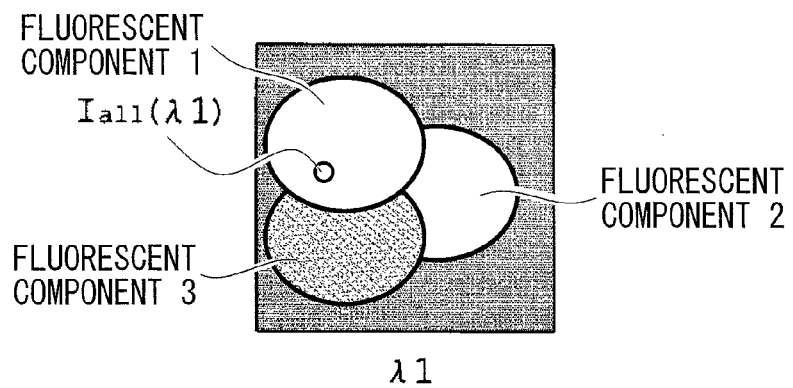
FIG. 16A is an explanatory diagram conceptually showing the distribution and brightness of a spectral image acquired by an image acquisition apparatus through a predetermined tunable light-dispersing element in a fluorescence-endoscope apparatus, and is a diagram showing a spectral image of the fluorescent component 1 at the maximum-fluorescence wavelength $\lambda 1$.
Figure 16B:
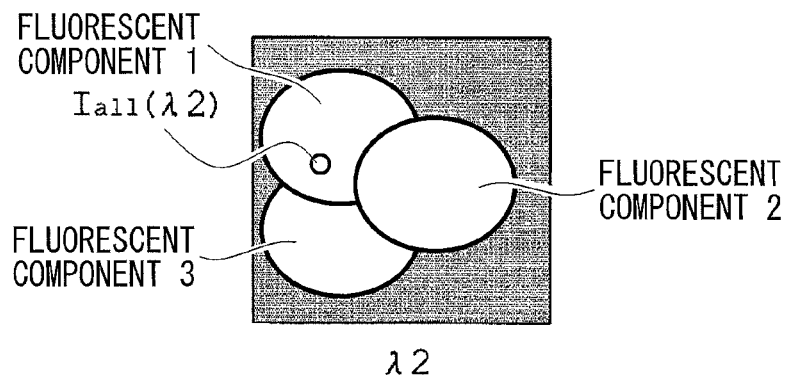
FIG. 16B is an explanatory diagram conceptually showing the distribution and brightness of a spectral image acquired by an image acquisition apparatus through a predetermined tunable light-dispersing element in a fluorescence-endoscope apparatus, and is a diagram showing a spectral image of the fluorescent component 2 at the maximum-fluorescence wavelength $\lambda 2$.
Figure 16C:
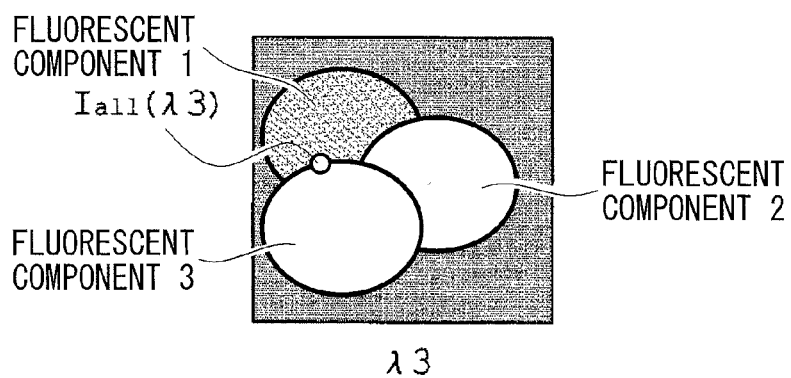
FIG. 16C is an explanatory diagram conceptually showing the distribution and brightness of a spectral image acquired by an image acquisition apparatus through a predetermined tunable light-dispersing element in a fluorescence-endoscope apparatus, and is a diagram showing a spectral image of the fluorescent component 3 at the maximum-fluorescence wavelength $\lambda 3$.
Figure 18A:
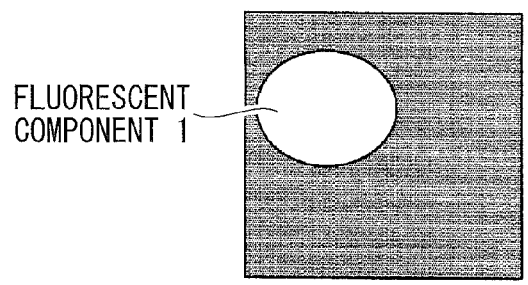
FIG. 18A is a diagram showing image processing after the UNMIXING processing, and is a distribution image of the fluorescent component 1 after the UNMIXING processing.
Figure 18B:
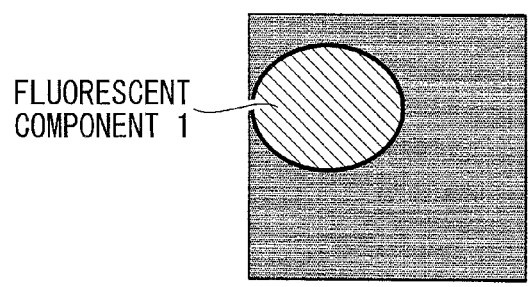
FIG. 18B is a diagram showing image processing after the UNMIXING processing, and is a diagram showing a state in which a predetermined color is assigned to a distributed region of the fluorescent component 1 in the distribution image in FIG. 18A.
Figure 18C:
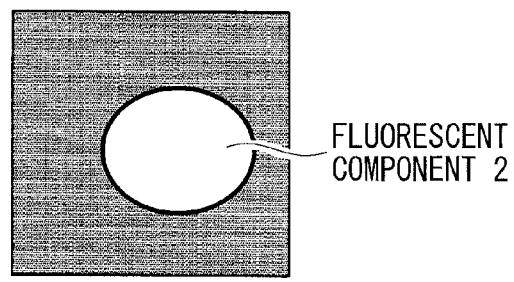
FIG. 18C is a diagram showing image processing after the UNMIXING processing, and is a distribution image of the fluorescent component 2 after the UNMIXING processing.
Figure 18D:
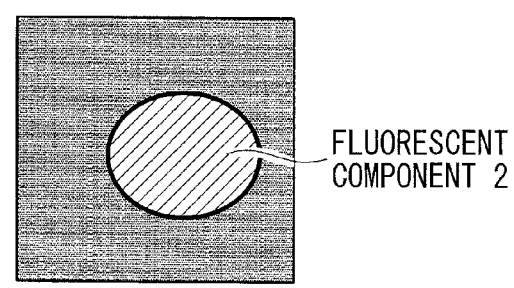
FIG. 18D is a diagram showing image processing after the UNMIXING processing, and is a diagram showing a state in which a predetermined color is assigned to a distributed region of the fluorescent component 2 in the distribution image in FIG. 18C.
Figure 18E:
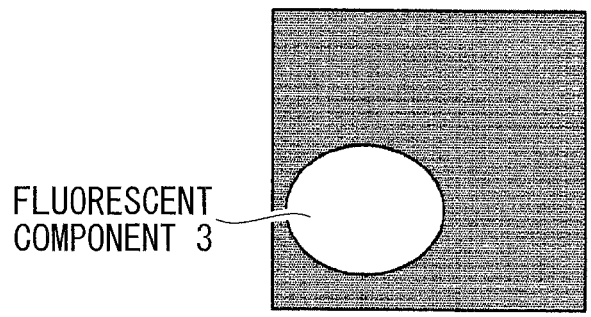
FIG. 18E is a diagram showing image processing after the UNMIXING processing, and is a distribution image of the fluorescent component 3 after the UNMIXING processing.
Figure 18F:
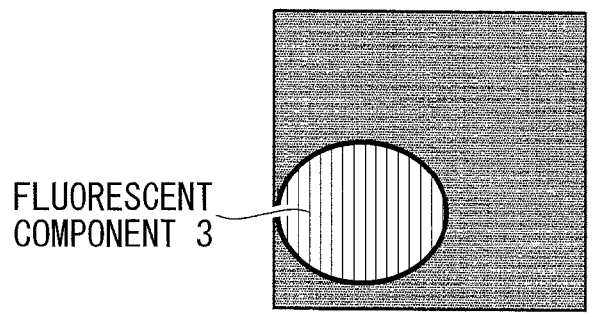
FIG. 18F is a diagram showing image processing after the UNMIXING processing, and is a diagram showing a state in which a predetermined color is assigned to a distributed region of the fluorescent component 3 in the distribution image in FIG. 18E.
Figure 18G:
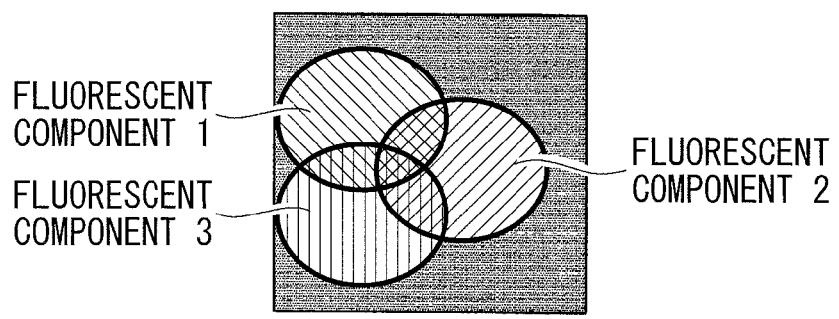
FIG. 18G is a diagram showing image processing after the UNMIXING processing, and is a diagram showing a state in which the distribution images shown in FIGS. 18B, 18D, and 18F are combined into one image.
Figure 19A:
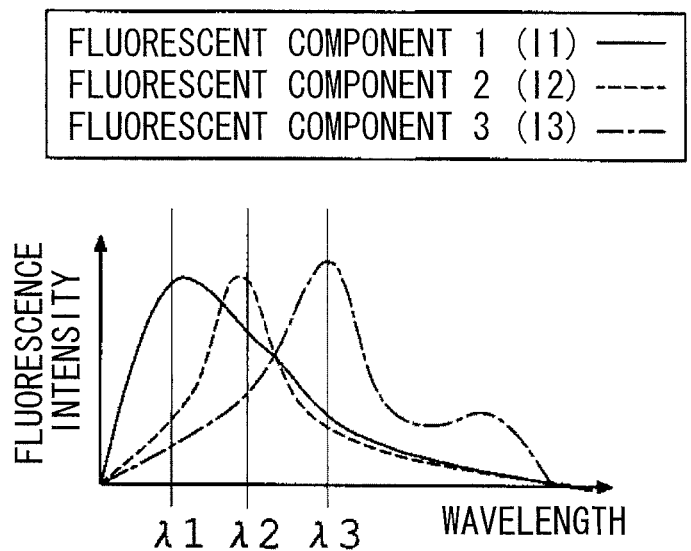
FIG. 19A is an explanatory diagram showing fluorescence intensities of three types of fluorescent components present in a sample, and is a diagram showing fluorescence spectra of the individual fluorescent components.
Figure 19B:
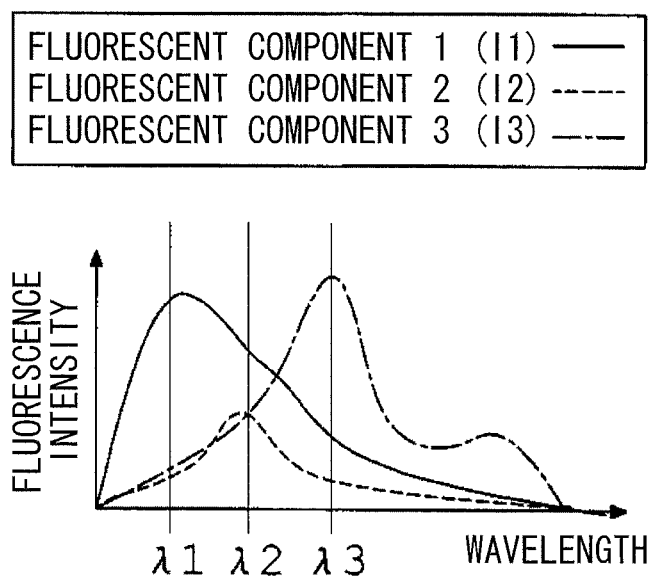
FIG. 19B is an explanatory diagram showing fluorescence intensities of three types of fluorescent components present in a sample, and is a diagram showing an example in which the fluorescence intensity of the fluorescent component 2 is different.
Figure 20A:
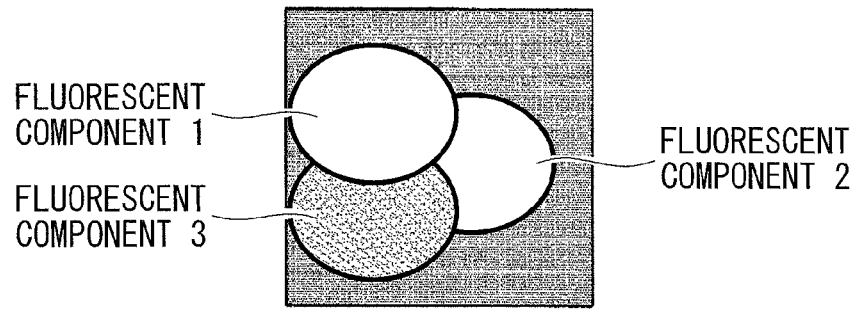
FIG. 20A is a diagram showing individual spectral images at the maximum-fluorescence wavelengths λ1 to λ3 when the three types of fluorescent components 1 to 3 have identical brightnesses, and is a diagram showing the spectral image at the fluorescence wavelength λ1.
Figure 20B:
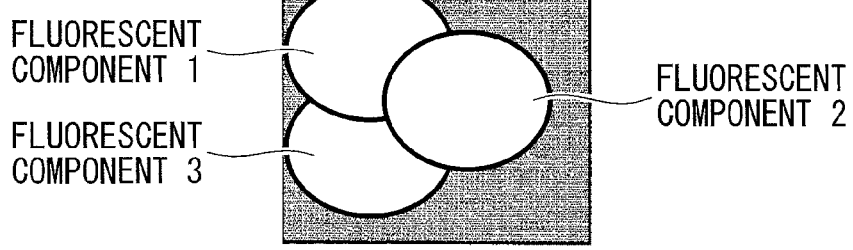
FIG. 20B is a diagram showing individual spectral images at the maximum-fluorescence wavelengths λ1 to λ3 when the three types of fluorescent components 1 to 3 have identical brightnesses, and is a diagram showing the spectral image at the fluorescence wavelength λ2.
Figure 20C:
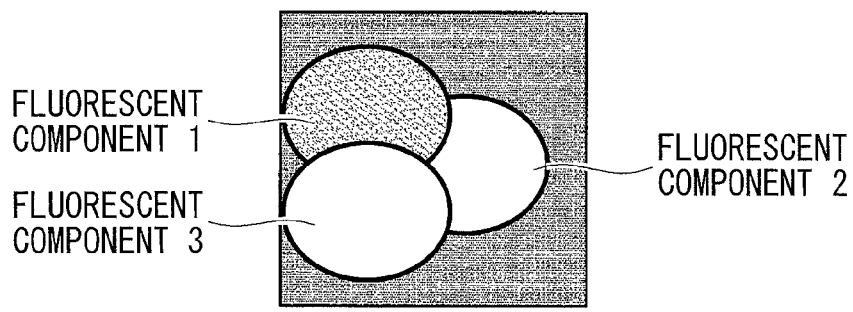
FIG. 20C is a diagram showing individual spectral images at the maximum-fluorescence wavelengths λ1 to λ3 when the three types of fluorescent components 1 to 3 have identical brightnesses, and is a diagram showing the spectral image at the fluorescence wavelength λ3.

FIGS. 7A to 7E are explanatory diagrams showing the exposure conditions in the fluorescence-endoscope apparatus of Example 1 and computation performed by the fluorescent-component-density computation unit 13$d_2$, where FIG. 7A is a diagram showing, in time-series, the light in each of the wavelength ranges selected by and transmitted through the tunable light-dispersing element 12$b_4$ under the reference exposure conditions, FIG. 7B is a diagram showing, in time-series, the light in each of the wavelength ranges that has been, at substantially the same time as in FIG. 7A, photoelectrically converted through the image acquisition device 12$b_5$ and stored in each of the frame memories 13$c_1$, 13$c_2$, and 13$c_3$, FIG. 7C is a diagram showing, in time-series, the light in each of the wavelength ranges selected by and transmitted through the tunable light-dispersing element 12$b_4$ under the exposure conditions in Example 1, FIG. 7D is a diagram showing, in time-series, the light in each of the wavelength ranges that has been, at substantially the same time as in FIG. 7C, photoelectrically converted through the image acquisition device 12$b_5$ and stored in each of the frame memories 13$c_1$, 13$c_2$, and 13$c_3$, and FIG. 7E is a diagram showing a matrix equation that is used in the UNMIXING processing performed by the fluorescent-component-density computation unit 13$d_2$ under the exposure conditions shown in FIG. 7C and FIG. 7D.

The basic configuration of the fluorescence-endoscope apparatus of Example 1 is as described above using FIGS. 1 and 2.

With the fluorescence-endoscope apparatus of Example 1, as shown in FIG. 7C, the exposure conditions are changed through the exposure-conditions setting unit 15 such that, by increasing transmitting time $t\lambda_2'$ of the fluorescence wavelength $\lambda 2$ from the fluorescent component 2 that has been transmitted through the tunable light-dispersing element 12$b_4$ in comparison with transmitting time $t\lambda_2$ under the reference exposure conditions shown in FIG. 7A so that the time to be stored by the frame memory 13$c_2$ is increased by the same amount, as shown in FIG. 7D.

When the density D1 of the fluorescent component 1 to the density Dm of the fluorescent component m are calculated using Equation (1), in accordance with the change in the exposure time that is made upon acquisition of the fluorescence image at the predetermined wavelength $\lambda x$ among the wavelength $\lambda 1$ to wavelength $\lambda n$ by the image acquisition portion 12$b$, the fluorescent-component-density computation unit 13$d_2$ multiplies the coefficients a1 ($\lambda x$) to am($\lambda x$) at the predetermined wavelength $\lambda x$ of the fluorescent component 1 to fluorescent component m at the normalized density under the reference exposure conditions by the ratio ($t\lambda_2'/t\lambda_2$) of the changed exposure time $t\lambda_2'$ to the exposure time $t\lambda_2$ under the reference exposure conditions when the fluorescence image at the predetermined wavelength $\lambda x$ is acquired by the image acquisition portion 12$b$.

The spectral image under the exposure conditions in Example 1 can be expressed as in Equation (1a') below, when expressed by a matrix equation using the UNMIXING coefficients:

[Expression 34]

$$\begin{pmatrix} a_1(\lambda 1) & a_2(\lambda 1) & a_3(\lambda 1) \\ a_1(\lambda 2) \times (t'_{\lambda 2}/t_{\lambda 2}) & a_2(\lambda 2) \times (t'_{\lambda 2}/t_{\lambda 2}) & a_3(\lambda 2) \times (t'_{\lambda 2}/t_{\lambda 2}) \\ a_1(\lambda 3) & a_2(\lambda 3) & a_3(\lambda 3) \end{pmatrix} \times \begin{pmatrix} D1 \\ D2 \\ D3 \end{pmatrix} = \begin{pmatrix} I_{all}(\lambda 1) \\ I_{all}(\lambda 2) \\ I_{all}(\lambda 3) \end{pmatrix}. \quad (1a')$$

According to this Equation (1a'), the fluorescent-component-density computation unit 13$d_2$ calculates the densities D1 to D3 of the fluorescent components 1 to 3.

According to the fluorescence-endoscope apparatus of Example 1, even if the exposure time for the spectral image at the specific detection wavelength is changed, because deterioration of the frame rate is minimized as much as possible, it is possible to detect, at high brightness, a plurality of fluorophores in a state where the individual detection wavelengths are separated.

Example 2

FIGS. 8A to 8C are explanatory diagrams showing the exposure conditions in the fluorescence-endoscope apparatus of Example 2 and computation performed by the fluorescent-component-density computation unit 13$d_2$, where FIG. 8A is a diagram showing, in time-series, the light in each of the wavelength ranges selected by and transmitted through the tunable light-dispersing element 12$b_4$ under the reference exposure conditions, FIG. 8B is a diagram showing, in time-series, the light in each of the wavelength ranges selected by and transmitted through the tunable light-dispersing element 12$b_4$ under the exposure conditions in Example 2, and FIG. 8C is a diagram showing a matrix equation that is used in the UNMIXING processing performed by the fluorescent-component-density computation unit 13$d_2$ under the exposure conditions shown in FIG. 8B.

With the fluorescence-endoscope apparatus of Example 2, as shown in FIG. 8B, the exposure conditions are changed through the exposure-conditions setting unit 15, while keeping the frame rate constant, such that the ratio of the exposure times $t\lambda_1''$, $t\lambda_2''$, and $t\lambda_3''$ at the individual detection wavelengths $\lambda 1$ to $\lambda 3$ differs from the ratio of the exposure times $t\lambda_1$, $t\lambda_2$, and $t\lambda_3$ at the individual detection wavelengths $\lambda 1$ to $\lambda 3$ under the reference exposure conditions shown in FIG. 8A.

When the density D1 of the fluorescent component 1 to the density D3 of the fluorescent component 3 are calculated using Equation (1), in accordance with the change in the exposure time that is made upon acquisition of the fluorescence image at the individual wavelengths of the wavelength $\lambda 1$ to wavelength $\lambda 3$ by the image acquisition portion 12$b$ while keeping the frame rate constant, the fluorescent-component-density computation unit 13$d_2$ individually multiplies the coefficients a1 ($\lambda 1$) to a3 ($\lambda 1$) to a1 ($\lambda 3$) to a3 ($\lambda 3$) at the individual wavelengths of the wavelength λ1 to wavelength λ3 of the fluorescent component 1 to fluorescent component 3 at the normalized density under the reference exposure conditions by the ratios ($t\lambda_1''/t\lambda_1$, $t\lambda_2''/t\lambda_2$, and $t\lambda_3''/t\lambda_3$) of the changed exposure times $t\lambda_1''$, $t\lambda_2''$, and $t\lambda_3''$ to the exposure times $t\lambda_1$, $t\lambda_2$, and $t\lambda_3$ under the reference exposure conditions when the fluorescence images at the individual wavelengths of the wavelength λ1 to wavelength λ3 are acquired by the image acquisition portion 12b.

The spectral images under the exposure conditions in Example 2 can be expressed as in Equation (1b') below when expressed by the matrix equation using the UNMIXING coefficients:

[Expression 35]

$$\begin{pmatrix} a_1(\lambda 1) \times (t''_{\lambda 1}/t_{\lambda 1}) & a_2(\lambda 1) \times (t''_{\lambda 1}/t_{\lambda 1}) & a_3(\lambda 1) \times (t''_{\lambda 1}/t_{\lambda 1}) \\ a_1(\lambda 2) \times (t''_{\lambda 2}/t_{\lambda 2}) & a_2(\lambda 2) \times (t''_{\lambda 2}/t_{\lambda 2}) & a_3(\lambda 2) \times (t''_{\lambda 2}/t_{\lambda 2}) \\ a_1(\lambda 3) \times (t''_{\lambda 3}/t_{\lambda 3}) & a_2(\lambda 3) \times (t''_{\lambda 3}/t_{\lambda 3}) & a_3(\lambda 3) \times (t''_{\lambda 3}/t_{\lambda 3}) \end{pmatrix} \times \quad (1b')$$

$$\begin{pmatrix} D1 \\ D2 \\ D3 \end{pmatrix} = \begin{pmatrix} I_{all}(\lambda 1) \\ I_{all}(\lambda 2) \\ I_{all}(\lambda 3) \end{pmatrix}.$$

According to this Equation (1b'), the fluorescent-component-density computation unit $13d_2$ calculates the densities D1 to D3 of the fluorescent components 1 to 3.

As described above, the frame rate is constant in Example 2. Accordingly, Equation (1b') above is expressed as:

$$\sum_{i=1}^{m} t_{\lambda i} = \sum_{j=1}^{m} t'' \lambda_j, m = 3. \quad \text{[Expression 36]}$$

According to the fluorescence-endoscope apparatus of Example 2, even if the exposure times for the spectral images at the individual detection wavelengths are changed in such a manner that deterioration of the frame rate is avoided, it is possible to detect, at high brightness, a plurality of fluorophores in a state where the individual detection wavelengths are separated and the brightnesses are balanced.

Other configurations, effects, and advantages are substantially the same as those of the fluorescence-endoscope apparatus of Example 1.

Example 3

FIGS. 9A to 9C are explanatory diagrams showing the exposure conditions in the fluorescence-endoscope apparatus of Example 3 and computation performed by the fluorescent-component-density computation unit $13d_2$, where FIG. 9A is a diagram showing, in time-series, the intensity and the irradiation timing of each excitation light beam that excites the fluorescence wavelengths of the individual fluorescent components under the reference exposure conditions, FIG. 9B is a diagram showing, in time-series, the intensity and the irradiation timing of each excitation light beam that excites the fluorescence wavelengths of the individual fluorescent components under the exposure conditions in Example 3, and FIG. 9C is a diagram showing a matrix equation that is used in the UNMIXING processing performed by the fluorescent-component-density computation unit $13d_2$ under the exposure conditions shown in FIG. 9B.

With the fluorescence-endoscope apparatus of Example 3, as shown in FIG. 9B, by increasing the intensity $I_{EX2}'$ of the excitation light that excites the fluorescence wavelength λ2 of the fluorescent component 2 compared with the intensity $I_{EX2}$ under the reference exposure conditions shown in FIG. 9A, the exposure conditions are changed through the exposure-conditions setting unit 15 such that the intensity stored in the frame memory $13c_2$ becomes stronger by the same amount.

When the density D1 of the fluorescent component 1 to the density D3 of the fluorescent component 3 are calculated using Equation (1), in accordance with the change in the intensity of the excitation light that excites the fluorescence wavelength λ2 that is made upon acquisition of the fluorescence image at the fluorescence wavelength λ2 by the image acquisition portion 12b, the fluorescent-component-density computation unit $13d_2$ multiplies the coefficients a1 (λ2) to a3 (λ2) at the wavelength λ2 of the fluorescent component 1 to fluorescent component 3 at the normalized density under the reference exposure conditions by the ratio ($I_{EX2}'/I_{EX2}$) of the changed intensity $I_{EX2}'$ of the excitation light that excites the fluorescence wavelength λ2 to the intensity $I_{EX2}$ of the excitation light that excites the fluorescence wavelength λ2 under the reference exposure conditions when the fluorescence image at the fluorescence wavelength λ2 is acquired by the image acquisition portion 12b.

The spectral images under the exposure conditions in Example 3 can be expressed as in Equation (1c') below when expressed by the matrix equation using the UNMIXING coefficients:

[Expression 37]

$$\begin{pmatrix} a_1(\lambda 1) & a_2(\lambda 1) & a_3(\lambda 1) \\ a_1(\lambda 2) \times (I'_{EX2}/I_{EX2}) & a_2(\lambda 2) \times (I'_{EX2}/I_{EX2}) & a_3(\lambda 2) \times (I'_{EX2}/I_{EX2}) \\ a_1(\lambda 3) & a_2(\lambda 3) & a_3(\lambda 3) \end{pmatrix} \quad (1c')$$

$$\times \begin{pmatrix} D1 \\ D2 \\ D3 \end{pmatrix} = \begin{pmatrix} I_{all}(\lambda 1) \\ I_{all}(\lambda 2) \\ I_{all}(\lambda 3) \end{pmatrix}.$$

According to this Equation (1c'), the fluorescent-component-density computation unit $13d_2$ calculates the densities D1 to D3 of the fluorescent components 1 to 3.

According to the fluorescence-endoscope apparatus of Example 3, even if the excitation intensity for the spectral image at the specific detection wavelength is changed in such a manner that deterioration of the frame rate is avoided, it is possible to detect, at high brightness, a plurality of fluorophores in a state where the individual detection wavelengths are separated.

Example 4

FIGS. 10A to 10C are explanatory diagrams showing the exposure conditions in the fluorescence-endoscope apparatus of Example 4 and computation performed by the fluorescent-component-density computation unit $13d_2$, where FIG. 10A is a diagram showing, in time-series, the intensity and the irradiation timing of each excitation light that excites the fluorescence wavelengths of the individual fluorescent components under the reference exposure conditions, FIG. 10B is a diagram showing, in time-series, the intensity and the irradiation timing of each excitation light beam that excites the fluorescence wavelengths of the individual fluorescent components under the exposure conditions in Example 4, and FIG. 10C is a diagram showing a matrix equation that is used in the UNMIXING processing performed by the fluorescent-component-density computation unit $13d_2$ under the exposure conditions shown in FIG. 10B.

With the fluorescence-endoscope apparatus of Example 4, as shown in FIG. 10B, by changing the intensities $I_{EX1}''$ to $I_{EX3}''$ of the individual excitation light beams that individually excite the fluorescence wavelength $\lambda 1$ of the fluorescent component 1 to fluorescence wavelength $\lambda 3$ of the fluorescent component 3 relative to the intensities $I_{EX1}$ to $I_{EX3}$ under the reference exposure conditions shown in FIG. 10A, the exposure conditions are changed through the exposure-conditions setting unit 15 such that the intensities stored in the frame memories $13c_1$ to $13c_3$ are changed by the same amount.

When the density D1 of the fluorescent component 1 to the density D3 of the fluorescent component 3 are calculated using Equation (1), in accordance with the change in the intensities of the excitation light beams that excite the individual wavelengths that is made upon acquisition of the fluorescence images at the individual wavelengths of the wavelength $\lambda 1$ to wavelength $\lambda 3$ by the image acquisition portion 12b, the fluorescent-component-density computation unit $13d_2$ individually multiplies the coefficients $a1(\lambda 1)$ to $a3(\lambda 1)$ to $a1(\lambda 3)$ to $a3(\lambda 3)$ at the individual wavelengths of the wavelength $\lambda 1$ to wavelength $\lambda 3$ of the fluorescent component 1 to fluorescent component 3 at the normalized density under the reference exposure conditions by the ratios ($I_{EX1}''$, $I_{EX1}$, $I_{EX2}''$, $I_{EX2}$, and $I_{EX3}''/I_{EX3}$) of the changed intensities $I_{EX1}''$, $I_{EX2}''$ and $I_{EX3}''$ of the excitation light that excites the individual wavelengths to the intensities $I_{EX1}$, $I_{EX2}$, and $I_{EX3}$ of the excitation light that excites the individual wavelengths under the reference exposure conditions when the fluorescence images at the individual wavelengths of the wavelength $\lambda 1$ to wavelength $\lambda 3$ are acquired by the image acquisition portion 12b.

The spectral images under the exposure conditions in Example 4 can be expressed as in Equation (1d') below when expressed by the matrix equation using the UNMIXING coefficients:

[Expression 38]

$$\begin{pmatrix} a_1(\lambda 1) \times (I_{EX1}''/I_{EX1}) & a_2(\lambda 1) \times (I_{EX1}''/I_{EX1}) & a_3(\lambda 1) \times (I_{EX1}''/I_{EX1}) \\ a_1(\lambda 2) \times (I_{EX2}''/I_{EX2}) & a_2(\lambda 2) \times (I_{EX2}''/I_{EX2}) & a_3(\lambda 2) \times (I_{EX2}''/I_{EX2}) \\ a_1(\lambda 3) \times (I_{EX3}''/I_{EX3}) & a_2(\lambda 3) \times (I_{EX3}''/I_{EX3}) & a_3(\lambda 3) \times (I_{EX3}''/I_{EX3}) \end{pmatrix} \quad (1d')$$

$$\times \begin{pmatrix} D1 \\ D2 \\ D3 \end{pmatrix} = \begin{pmatrix} I_{all}(\lambda 1) \\ I_{all}(\lambda 2) \\ I_{all}(\lambda 3) \end{pmatrix}.$$

According to this Equation (1d'), the fluorescent-component-density computation unit $13d_2$ calculates the densities D1 to D3 of the fluorescent components 1 to 3.

According to the fluorescence-endoscope apparatus of Example 4, even if the excitation intensity for the spectral image at the individual detection wavelengths is changed in such a manner that deterioration of the frame rate is avoided, it is possible to detect, at high brightness, a plurality of fluorophores in a brightness state where the individual detection wavelengths are separated and the brightnesses are balanced.

Example 5

FIGS. 11A to 11C are explanatory diagrams showing the exposure conditions in the fluorescence-endoscope apparatus of Example 5 and computation performed by the fluorescent-component-density computation unit $13d_2$, where FIG. 11A is a diagram showing, in time-series, the intensity and the irradiation timing of each excitation light beam that excites the fluorescence wavelengths of the individual fluorescent components under the reference exposure conditions, FIG. 11B is a diagram showing, in time-series, the intensity and the irradiation timing of each excitation light beam that excite the fluorescence wavelengths of the individual fluorescent components in Example 5, and FIG. 11C is a diagram showing a matrix equation that is used in the UNMIXING processing performed by the fluorescent-component-density computation unit $13d_2$ under the exposure conditions shown in FIG. 11B.

With the fluorescence-endoscope apparatus of Example 5, as shown in FIG. 11B, by reducing the excitation time $t_{Ex2}'$ of the excitation light that excites the fluorescence wavelength $\lambda 2$ of the fluorescent component 2 compared with the excitation time $t_{Ex2}$ under the reference exposure conditions shown in FIG. 11A, the exposure conditions are changed through the exposure-conditions setting unit 15 such that the intensity stored in the frame memory $13c_2$ becomes weaker by the same amount.

When the density D1 of the fluorescent component 1 to the density D3 of the fluorescent component 3 are calculated using Equation (1), in accordance with the change in the intensity of the excitation light that excites the fluorescence wavelength $\lambda 2$ that is made upon acquisition of the fluorescence image at the fluorescence wavelength $\lambda 2$ by the image acquisition portion 12b, the fluorescent-component-density computation unit $13d_2$ multiplies the coefficients $a1(\lambda 2)$ to $a3(\lambda 2)$ at the wavelength $\lambda 2$ of the fluorescent component 1 to fluorescent component 3 at the normalized density under the reference exposure conditions by the ratio ($t_{EX2}'/t_{EX2}$) of the changed excitation time $t_{EX2}'$ of the excitation light that excites the fluorescence wavelength $\lambda 2$ to the excitation time $t_{EX2}$ of excitation light that excites the fluorescence wavelength $\lambda 2$ under the reference exposure conditions when the fluorescence image at the fluorescence wavelength $\lambda 2$ is acquired by the image acquisition portion 12b.

The spectral images under the exposure conditions in Example 5 can be expressed as in Equation (1e') below when expressed by the matrix equation using the UNMIXING coefficients:

[Expression 39]

$$\begin{pmatrix} a_1(\lambda 1) & a_2(\lambda 1) & a_3(\lambda 1) \\ a_1(\lambda 2) \times (t_{EX2}'/t_{EX2}) & a_2(\lambda 2) \times (t_{EX2}'/t_{EX2}) & a_3(\lambda 2) \times (t_{EX2}'/t_{EX2}) \\ a_1(\lambda 3) & a_2(\lambda 3) & a_3(\lambda 3) \end{pmatrix} \quad (1e')$$

$$\times \begin{pmatrix} D1 \\ D2 \\ D3 \end{pmatrix} = \begin{pmatrix} I_{all}(\lambda 1) \\ I_{all}(\lambda 2) \\ I_{all}(\lambda 3) \end{pmatrix}.$$

According to this Equation (1e'), the fluorescent-component-density computation unit $13d_2$ calculates the densities D1 to D3 of the fluorescent components 1 to 3.

According to the fluorescence-endoscope apparatus of Example 5, even if the excitation time for the spectral image at the specific detection wavelength is changed in such a manner that deterioration of the frame rate is avoided, it is possible to detect, at high brightness, a plurality of fluorophores in a state where the individual detection wavelengths are separated and the brightnesses are balanced.

Example 6

FIGS. 12A to 12C are explanatory diagrams showing the exposure conditions in the fluorescence-endoscope apparatus of Example 6 and computation performed by the fluorescent-component-density computation unit 13$d_2$, where FIG. 12A is a diagram showing, in time-series, the intensity and the irradiation timing of each excitation light beam that excites the fluorescence wavelengths of the individual fluorescent components under the reference exposure conditions, FIG. 12B is a diagram showing, in time-series, the intensity and the irradiation timing of each excitation light beam that excites the fluorescence wavelengths of the individual fluorescent components under the exposure conditions in Example 6, and FIG. 12C is a diagram showing a matrix equation that is used in the UNMIXING processing performed by the fluorescent-component-density computation unit 13$d_2$ under the exposure conditions shown in FIG. 12B.

With the fluorescence-endoscope apparatus of Example 6, as shown in FIG. 12B, by changing the excitation intensity $I_{Ex2}'$ and the excitation time $t_{Ex2}'$ of the excitation light that excites the fluorescence wavelength λ2 of the fluorescent component 2 relative to the excitation intensity $I_{Ex2}$ and the excitation time $t_{Ex2}$ under the reference exposure conditions shown in FIG. 12A, the exposure conditions are changed through the exposure-conditions setting unit 15 such that the intensity stored in the frame memory 13$c_2$ is changed by the same amount.

When the density D1 of the fluorescent component 1 to the density D3 of the fluorescent component 3 are calculated using Equation (1), in accordance with the change in the intensity and the excitation time of the excitation light that excites the predetermined wavelength λ2 that is made upon acquisition of the fluorescence image at the predetermined wavelength λ2 among the wavelength λ1 to wavelength λ3 by the image acquisition portion 12$b$, the fluorescent-component-density computation unit 13$d_2$ multiplies the coefficients a1(λ2) to a3(λ2) at the wavelength λ2 of the fluorescent component 1 to fluorescent component 3 at the normalized density under the reference exposure conditions by the ratio $((I_{Ex2}'/I_{Ex2})\times(t_{Ex2}'/t_{Ex2}))$ of the changed intensity $I_{Ex2}'$ and the changed excitation time $t_{Ex2}'$ of the excitation light that excites the predetermined wavelength λ2 to the intensity $I_{Ex2}$ and the excitation time $t_{Ex2}$ of the excitation light that excites the predetermined wavelength λ2 under the reference exposure conditions when the fluorescence image at the predetermined wavelength λ2 is acquired by the image acquisition portion 12$b$.

The spectral images under the exposure conditions in Example 6 can be expressed as in Equation (1f') below when expressed by the matrix equation using the UNMIXING coefficients:

[Expression 40]

$$\begin{pmatrix} a_1(\lambda 1) & a_2(\lambda 1) & a_3(\lambda 1) \\ a_1(\lambda 2)\times\alpha_2 6 & a_2(\lambda 2)\times\alpha_2 6 & a_3(\lambda 2)\times\alpha_2 6 \\ a_1(\lambda 3) & a_2(\lambda 3) & a_3(\lambda 3) \end{pmatrix} \times \begin{pmatrix} D1 \\ D2 \\ D3 \end{pmatrix} = \begin{pmatrix} I_{all}(\lambda 1) \\ I_{all}(\lambda 2) \\ I_{all}(\lambda 3) \end{pmatrix} \quad (1f')$$

where $\alpha_2 6 = I_{Ex2}'\times t_{Ex2}'/I_{Ex2}\times t_{Ex2}$.

According to this Equation (1f'), the fluorescent-component-density computation unit 13$d_2$ calculates the densities D1 to D3 of the fluorescent components 1 to 3.

According to the fluorescence-endoscope apparatus of Example 6, even if the excitation intensity and the excitation time for the spectral image at the specific detection wavelength are changed in such a manner that deterioration of the frame rate is avoided, it is possible to detect, at high brightness, a plurality of fluorophores in a state where the individual detection wavelengths are separated and the brightnesses are balanced.

Example 7

FIGS. 13A to 13C are explanatory diagrams showing the exposure conditions in the fluorescence-endoscope apparatus of Example 7 and computation performed by the fluorescent-component-density computation unit 13$d_2$, where FIG. 13A is a diagram showing, in time-series, the intensity and the irradiation timing of each excitation light beam that excites the fluorescence wavelengths of the individual fluorescent components under the reference exposure conditions, FIG. 13B is a diagram showing, in time-series, the intensity and the irradiation timing of each excitation light beam that excites the fluorescence wavelengths of the individual fluorescent components under the exposure conditions in Example 7, and FIG. 13C is a diagram showing a matrix equation that is used in the UNMIXING processing performed by the fluorescent-component-density computation unit 13$d_2$ under the exposure conditions shown in FIG. 13B.

With the fluorescence-endoscope apparatus of Example 7, by changing the intensity of the fluorescence wavelength λ2 of the fluorescent component 2 using an ND filter, the exposure conditions are changed through the exposure-conditions setting unit 15 such that, as shown in FIG. 13B, the detection intensity $I_2'$ stored in the frame memory 13$c_2$ becomes weaker by the same amount.

When the density D1 of the fluorescent component 1 to the density D3 of the fluorescent component 3 are calculated using Equation (1), in accordance with the change in the detection intensity that is made upon acquisition of the fluorescence image at the predetermined wavelength λ2 among the wavelength λ1 to wavelength λ3 by the image acquisition portion 12$b$, the fluorescent-component-density computation unit 13$d_2$ multiplies the coefficients a1(λ2) to a3(λ2) at the predetermined wavelength λ2 of the fluorescent component 1 to fluorescent component 3 at the normalized density under the reference exposure conditions by the ratio $(I_2'/I_2)$ of the changed detection intensity $I_2'$ to the detection intensity $I_2$ under the reference exposure conditions when the fluorescence image at the predetermined wavelength λ2 is acquired by the image acquisition portion 12$b$.

The spectral images under the exposure conditions in Example 7 can be expressed as in Equation (1g') below when expressed by the matrix equation using the UNMIXING coefficients.

[Expression 41]

$$\begin{pmatrix} a_1(\lambda 1) & a_2(\lambda 1) & a_3(\lambda 1) \\ a_1(\lambda 2)\times(I_2'/I_2) & a_2(\lambda 2)\times(I_2'/I_2) & a_3(\lambda 2)\times(I_2'/I_2) \\ a_1(\lambda 3) & a_2(\lambda 3) & a_3(\lambda 3) \end{pmatrix} \times \begin{pmatrix} D1 \\ D2 \\ D3 \end{pmatrix} = \begin{pmatrix} I_{all}(\lambda 1) \\ I_{all}(\lambda 2) \\ I_{all}(\lambda 3) \end{pmatrix} \quad (1g')$$

According to this Equation (1g'), the fluorescent-component-density computation unit 13$d_2$ calculates the densities D1 to D3 of the fluorescent components 1 to 3.

According to the fluorescence-endoscope apparatus of Example 7, even if the detection intensity for the spectral image at the specific detection wavelength is changed in such a manner that deterioration of the frame rate is avoided, it is possible to detect, at high brightness, a plurality of fluorophores in a state where the individual detection wavelengths are separated and the brightnesses are balanced.

Example 8

FIGS. 14A to 14C are explanatory diagrams showing the exposure conditions in the fluorescence-endoscope apparatus of Example 8 and computation performed by the fluorescent-component-density computation unit $13d_2$, where FIG. 14A is a diagram showing, in time-series, the gain and the detection timing of the fluorescence images at the fluorescence wavelengths of the individual fluorescent components under the reference exposure conditions, FIG. 14B is a diagram showing, in time-series, the gain and the detection timing of the fluorescence images at the fluorescence wavelengths of the individual fluorescent components under the exposure conditions in Example 8, and FIG. 14C is a diagram showing a matrix equation that is used in the UNMIXING processing performed by the fluorescent-component-density computation unit $13d_2$ under the exposure conditions shown in FIG. 14B.

With the fluorescence-endoscope apparatus of Example 8, as shown in FIG. 14B, by changing the gain $G_2'$ at the fluorescence wavelength $\lambda 2$ of the fluorescent component 2, the exposure conditions are changed through the exposure-conditions setting unit 15 such that the intensity stored in the frame memory $13c_2$ becomes stronger by the same amount.

When the density D1 of the fluorescent component 1 to the density D3 of the fluorescent component 3 are calculated using Equation (1), in accordance with the change in the gain that is made upon acquisition of the fluorescence image at the predetermined wavelength $\lambda 2$ among the wavelength $\lambda 1$ to wavelength $\lambda 3$ by the image acquisition portion $12b$, the fluorescent-component-density computation unit $13d_2$ multiplies the coefficients $a1(\lambda 2)$ to $a3(\lambda 2)$ at the predetermined wavelength $\lambda 2$ of the fluorescent component 1 to fluorescent component 3 at the normalized density under the reference exposure conditions by the ratio $(G2'/G2)$ of the changed gain $G_2'$ to the gain $G_2$ under the reference exposure conditions when the fluorescence image at the predetermined wavelength $\lambda 2$ is acquired by the image acquisition portion $12b$.

The spectral images under the exposure conditions in Example 8 can be expressed as in Equation (1h') below when expressed by the matrix equation using the UNMIXING coefficients:

[Expression 42]

$$\begin{pmatrix} a_1(\lambda 1) & a_2(\lambda 1) & a_3(\lambda 1) \\ a_1(\lambda 2) \times (G_2'/G_2) & a_2(\lambda 2) \times (G_2'/G_2) & a_3(\lambda 2) \times (G_2'/G_2) \\ a_1(\lambda 3) & a_2(\lambda 3) & a_3(\lambda 3) \end{pmatrix} \times \begin{pmatrix} D1 \\ D2 \\ D3 \end{pmatrix} = \begin{pmatrix} I_{all}(\lambda 1) \\ I_{all}(\lambda 2) \\ I_{all}(\lambda 3) \end{pmatrix}. \quad (1h')$$

According to this Equation (1h'), the fluorescent-component-density computation unit $13d_2$ calculates the densities D1 to D3 of the fluorescent components 1 to 3.

According to the fluorescence-endoscope apparatus of Example 8, even if the gain for the spectral image at the specific detection wavelength is changed in such a manner that deterioration of the frame rate is avoided, it is possible to detect, at high brightness, a plurality of fluorophores in a state where the individual detection wavelengths are separated and the brightnesses are balanced.

Although Examples of the present invention have been described above, the fluorescence-endoscope apparatus of the present invention is not limited to these Examples: for example, regarding the change in the combined exposure conditions of the exposure condition items in the individual examples, the fluorescent-component-density computation unit $13d_2$ may multiply the ratio of the values of the combination of the exposure condition items under the reference exposure conditions to the values of the combination of the changed exposure condition items by the UNMIXING coefficients of the fluorescent component 1 to fluorescent component 3 at the normalized density under the reference exposure conditions. Furthermore, in accordance with the change in any of the exposure condition items, the fluorescent-component-density computation unit $13d_2$ may multiply the ratio of the values after the change of the changed exposure condition items to the values of the exposure condition items under the reference exposure conditions by the UNMIXING coefficients under the reference exposure conditions. It is possible to apply the fluorescence-endoscope apparatus of the present invention to the detection of fluorescent components in various combinations, including a plurality of human tissues alone, a plurality of fluorescence agents alone, or residues.

INDUSTRIAL APPLICABILITY

The fluorescence-endoscope apparatus of the present invention is effective in the fields of detecting the fluorescence spectra produced from biological tissue in order to observe the biological tissue.

What is claimed is:

1. A fluorescence-endoscope apparatus that radiates excitation light onto biological tissue containing a plurality of types of fluorescent components, whose maximum-fluorescence wavelengths are different and whose fluorescence wavelengths overlap in at least parts of the wavelength ranges, that acquires a plurality of types of images of fluorescence generated by the biological tissue, and that displays, in a separated manner, the plurality of types of fluorescent components present in the biological tissue using the acquired fluorescence images, comprising:

a light source portion that emits at least one type of excitation light that excites the plurality of types of fluorescent components;

a fluorescence image capturing unit that acquires the images of fluorescence generated by the biological tissue for every n types [where, m≤n] of wavelength $\lambda 1$ to wavelength $\lambda n$;

a fluorescence-spectrum storage unit that records fluorescence spectra of m types [where, 2≤m] of individual fluorescent component 1 to fluorescent component m present in the biological tissue at normalized densities under reference exposure conditions;

a fluorescent-component-density computation unit that obtains densities of the individual fluorescent components present in the biological tissue for all pixels in the fluorescence images by performing computation using the fluorescence spectra of the individual fluorescent component 1 to fluorescent component m at the normalized densities under the reference exposure conditions that are stored in the fluorescence-spectrum storage unit and the fluorescence images for every wavelength λ1 to wavelength λn acquired by the fluorescence image capturing unit;

a fluorescence-image combining portion that forms distribution images of the individual fluorescent components on the basis of the densities of the individual fluorescent components obtained by the fluorescent-component-density computation unit, assigns predetermined colors corresponding to the individual fluorescent components to the formed distribution images of the individual fluorescent components, and combines the distribution images to which the predetermined colors are assigned into one image; and an image display portion that displays the image that has been combined by the fluorescence-image combining portion, wherein, when a1(λ1) to a1(λn) to am(λ1) to am(λn) are defined as coefficients at the wavelength λ1 to wavelength λn of the fluorescent component 1 to fluorescent component m at the individual normalized densities under the reference exposure conditions, which are obtained from the fluorescence spectra, stored in the fluorescence-spectrum storage unit, of the fluorescent component 1 to fluorescent component m at the individual normalized densities under the reference exposure conditions, $I_{all}(\lambda 1)$ to $I_{all}(\lambda n)$ are defined as intensities of the fluorescence images at the wavelength λ1 to wavelength λn acquired by the fluorescence image capturing unit, and D1 to Dm are defined as the densities of the fluorescent components 1 to fluorescent component m, the fluorescent-component-density computation unit calculates, for all pixels, the density D1 of the fluorescent component 1 to the density Dm of the fluorescent component m in each pixel in the fluorescence images using Equation (1) below, and wherein the fluorescent-component-density computation unit:

checks if the reference exposure conditions of an exposure condition item have been changed; and if a value of a predetermined exposure condition item has been changed when the fluorescence image at at least one wavelength λx among the wavelength λ1 to wavelength λn is acquired by the fluorescence image capturing unit, in accordance with the change, when the density D1 of the fluorescent component 1 to the density Dm of the fluorescent component m are calculated using Equation (1), changes the coefficients a1(λx) to am(λx) at the wavelength λx of the fluorescent component 1 to fluorescent component m at the normalized density under the reference exposure conditions using the ratio of the value of the changed predetermined exposure condition item to the value of the predetermined exposure condition item under the reference exposure conditions when the fluorescence image at the wavelength λx is acquired by the fluorescence image capturing unit:

[Expression 1]

$$\begin{pmatrix} D1 \\ \vdots \\ Dm \end{pmatrix} = \begin{pmatrix} a1(\lambda 1) & \cdots & am(\lambda 1) \\ \vdots & \vdots & \vdots \\ a1(\lambda n) & \cdots & am(\lambda n) \end{pmatrix}^{-1} \begin{pmatrix} I_{all}(\lambda 1) \\ \vdots \\ I_{all}(\lambda n) \end{pmatrix} \quad 式(1)$$

Equation (1).

2. A fluorescence-endoscope apparatus according to claim 1, wherein if the exposure time has been changed when the fluorescence image at the predetermined wavelength λx among the wavelength λ1 to wavelength λn is acquired by the fluorescence image capturing unit, in accordance with the change, when the density D1 of the fluorescent component 1 to the density Dm of the fluorescent component m are calculated using Equation (1), the fluorescent-component-density computation unit multiplies the coefficients a1(λx) to am(λx) at the predetermined wavelength λx of the fluorescent component 1 to fluorescent component m at the normalized density under the reference exposure conditions by the ratio of the changed exposure time to the exposure time under the reference exposure conditions when the fluorescence image at the predetermined wavelength λx is acquired by the fluorescence image capturing unit.

3. A fluorescence-endoscope apparatus according to claim 1, wherein if the exposure times have been changed while keeping a frame rate constant when the fluorescence images at the individual wavelengths of the wavelength λ1 to wavelength λn are acquired by the fluorescence image capturing unit, in accordance with the change, when the density D1 of the fluorescent component 1 to the density Dm of the fluorescent component m are calculated using Equation (1), the fluorescent-component-density computation unit multiplies the coefficients a1(λ1) to am(λ1) to a1(λn) to am(λn) at individual wavelengths among the wavelength λ1 to wavelength λn of the fluorescent component 1 to fluorescent component m at the normalized density under the reference exposure conditions by the ratio of the changed exposure time to the exposure time under the reference exposure conditions when the fluorescence images at the individual wavelengths of the wavelength λ1 to wavelength λn are acquired by the fluorescence image capturing unit.

4. A fluorescence-endoscope apparatus according to claim 1, wherein if the intensity of the excitation light that excites the predetermined wavelength λx has been changed when the fluorescence image at the predetermined wavelength λx among the wavelength λ1 to wavelength λn is acquired by the fluorescence image capturing unit, in accordance with the change, when the density D1 of the fluorescent component 1 to the density Dm of the fluorescent component m are calculated using Equation (1), the fluorescent-component-density computation unit multiplies the coefficients a1(λx) to am(λx) at the wavelength λx of the fluorescent component 1 to fluorescent component m at the normalized density under the reference exposure conditions by the ratio of the changed intensity of the excitation light that excites the predetermined wavelength λx to the intensity of the excitation light that excites the predetermined wavelength λx under the reference exposure conditions when the fluorescence image at the predetermined wavelength λx is acquired by the fluorescence image capturing unit.

5. A fluorescence-endoscope apparatus according to claim 1, wherein if the intensities of the excitation light that excite the individual wavelengths have been changed when the fluorescence images at the individual wavelengths of the wavelength λ1 to wavelength λn are acquired by the fluorescence image capturing unit, in accordance with the change, when the density D1 of the fluorescent component 1 to the density Dm of the fluorescent component m are calculated using Equation (1), the fluorescent-component-density computation unit multiplies the coefficients a1(λ1) to am(λ1) to a1(λn) to am(λn) at individual wavelengths among the wavelength λ1 to wavelength λn of the fluorescent component 1 to fluorescent component m at the normalized density under the reference exposure conditions by the ratios of the changed intensities of the excitation light that excite the individual wavelengths to the intensities of the excitation light that excite the individual wavelengths under the reference exposure conditions when the fluorescence images at the individual wavelengths of the wavelength λ1 to wavelength λn are acquired by the fluorescence image capturing unit.

6. A fluorescence-endoscope apparatus according to claim 1, wherein if the excitation time of the excitation light that excites the predetermined wavelength λx has been changed when the fluorescence image at predetermined wavelength λx among the wavelength λ1 to wavelength λn is acquired by the fluorescence image capturing unit, in accordance with the change, when the density D1 of the fluorescent component 1 to the density Dm of the fluorescent component m are calculated using Equation (1), the fluorescent-component-density computation unit multiplies the coefficients a1(λx) to am(λx) at the wavelength λx of the fluorescent component 1 to fluorescent component m at the normalized density under the reference exposure conditions by the ratio of the changed excitation time of the excitation light that excites the predetermined wavelength λx to the excitation time of the excitation light that excites the predetermined wavelength λx under the reference exposure conditions when the fluorescence image at the predetermined wavelength λx is acquired by the fluorescence image capturing unit.

7. A fluorescence-endoscope apparatus according to claim 1, wherein if the intensity and the excitation time of the excitation light that excites the predetermined wavelength λx have been changed when the fluorescence image at predetermined wavelength λx among the wavelength λ1 to wavelength λn is acquired by the fluorescence image capturing unit, in accordance with the change, when the density D1 of the fluorescent component 1 to the density Dm of the fluorescent component m are calculated using Equation (1), the fluorescent-component-density computation unit multiplies the coefficients a1(λx) to am(λx) at the wavelength λx of the fluorescent component 1 to fluorescent component m at the normalized density under the reference exposure conditions by the ratios of the changed intensity and the changed excitation time of the excitation light that excites the predetermined wavelength λx to the intensity and the excitation time of the excitation light that excites the predetermined wavelength λx under the reference exposure conditions when the fluorescence image at the predetermined wavelength λx is acquired by the fluorescence image capturing unit.

8. A fluorescence-endoscope apparatus according to claim 1, wherein if a detection intensity has been changed when the fluorescence image at the predetermined wavelength λx among the wavelength λ1 to wavelength λn is acquired by the fluorescence image capturing unit, in accordance with the change, when the density D1 of the fluorescent component 1 to the density Dm of the fluorescent component m are calculated using Equation (1), the fluorescent-component-density computation unit multiplies the coefficients a1(λx) to am(λx) at the predetermined wavelength λx of the fluorescent component 1 to fluorescent component m at the normalized density under the reference exposure conditions by the ratio of the changed detection intensity to the detection intensity under the reference exposure conditions when the fluorescence image at the predetermined wavelength λx is acquired by the fluorescence image capturing unit.

9. A fluorescence-endoscope apparatus according to claim 1, wherein if a gain has been changed when the fluorescence image at the predetermined wavelength λx among the wavelength λ1 to wavelength λn is acquired by the fluorescence image capturing unit, in accordance with the change, when the density D1 of the fluorescent component 1 to the density Dm of the fluorescent component m are calculated using Equation (1), the fluorescent-component-density computation unit multiplies the coefficients a1(λx) to am(λx) at the predetermined wavelength λx of the fluorescent component 1 to fluorescent component m at the normalized density under the reference exposure conditions by the ratio of the changed gain to the gain under the reference exposure conditions when the fluorescence image at the predetermined wavelength λx is acquired by the fluorescence image capturing unit.

* * * * *